US008163885B2

(12) United States Patent
Svensson et al.

(10) Patent No.: US 8,163,885 B2
(45) Date of Patent: Apr. 24, 2012

(54) HUMANIZED ANTIBODIES AGAINST HUMAN INTERFERON-ALPHA

(75) Inventors: Lars Anders Svensson, Malmö (SE); Soren Padkjaer, Værløse (DK); Birgitte Friedrichsen, Gentofte (DK); Berit Olsen Krogh, Rødovre (DK); Inger Lund Pedersen, Vanløse (DK)

(73) Assignee: Argos Therapeutics, Inc., Durham, NC (US)

( * ) Notice: Subject to any disclaimer, the term of this patent is extended or adjusted under 35 U.S.C. 154(b) by 0 days.

(21) Appl. No.: 12/597,357

(22) PCT Filed: May 6, 2009

(86) PCT No.: PCT/EP2009/055448
§ 371 (c)(1),
(2), (4) Date: Mar. 17, 2010

(87) PCT Pub. No.: WO2009/135861
PCT Pub. Date: Nov. 12, 2009

(65) Prior Publication Data
US 2011/0213125 A1 Sep. 1, 2011

Related U.S. Application Data

(60) Provisional application No. 61/056,193, filed on May 27, 2008.

(30) Foreign Application Priority Data

May 7, 2008 (EP) ..................................... 08103847

(51) Int. Cl.
*C07K 16/00* (2006.01)
*A61K 39/395* (2006.01)
(52) U.S. Cl. ............... 530/388.2; 530/389.2; 424/130.1; 424/133.1
(58) Field of Classification Search .................. None
See application file for complete search history.

(56) References Cited

U.S. PATENT DOCUMENTS

| | | | |
|---|---|---|---|
| 4,362,155 A | 12/1982 | Skurkovich et al. |
| 4,423,147 A | 12/1983 | Secher et al. |
| 4,474,754 A | 10/1984 | Shimizu et al. |
| 4,605,394 A | 8/1986 | Skurkovich et al. |
| 4,824,432 A | 4/1989 | Skurkovich et al. |
| 4,902,618 A | 2/1990 | Berg et al. |
| 4,973,556 A | 11/1990 | Bove et al. |
| 5,055,289 A | 10/1991 | Frincke et al. |
| 5,888,511 A | 3/1999 | Skurkovich et al. |
| 5,919,453 A | 7/1999 | Benoit et al. |
| 6,136,309 A | 10/2000 | Novick et al. |
| 6,333,032 B1 | 12/2001 | Skurkovich et al. |
| 6,458,932 B1 | 10/2002 | Novick et al. |
| 6,458,934 B1 | 10/2002 | Hong et al. |
| 6,475,983 B1 | 11/2002 | Eid et al. |
| 6,660,523 B2 | 12/2003 | Blom et al. |
| 6,713,609 B1 | 3/2004 | Chuntharapai et al. |
| 6,787,634 B2 | 9/2004 | Benoit et al. |
| 7,087,726 B2 | 8/2006 | Chuntharapai et al. |
| 7,179,465 B2 | 2/2007 | Benoit et al. |
| 7,402,305 B2 | 7/2008 | Escary et al. |
| 7,544,357 B2 | 6/2009 | Banchereau et al. |
| 2002/0160974 A1 | 10/2002 | Banchereau et al. |
| 2003/0018174 A1 | 1/2003 | Kim et al. |
| 2003/0021764 A1 | 1/2003 | Maroun et al. |
| 2003/0147889 A1 | 8/2003 | Tovey et al. |
| 2003/0166228 A1 | 9/2003 | Chuntharapai et al. |
| 2004/0067888 A1 | 4/2004 | Tovey et al. |
| 2004/0170626 A1 | 9/2004 | Schuurman et al. |
| 2005/0013799 A1 | 1/2005 | Skurkovich et al. |
| 2005/0013800 A1 | 1/2005 | Skurkovich et al. |
| 2005/0013813 A1 | 1/2005 | Maroun et al. |
| 2007/0014724 A1 | 1/2007 | Witte et al. |
| 2007/0048311 A1 | 3/2007 | Chuntharapai et al. |
| 2008/0160030 A1 | 7/2008 | Banchereau et al. |
| 2009/0155286 A1 | 6/2009 | Gilliet et al. |
| 2009/0214565 A1 | 8/2009 | Banchereau et al. |
| 2009/0263474 A1 | 10/2009 | Banchereau et al. |
| 2009/0324605 A1 | 12/2009 | Witte et al. |

FOREIGN PATENT DOCUMENTS

| | | |
|---|---|---|
| EP | 0563487 A1 | 10/1993 |
| EP | 1351707 A0 | 8/2002 |
| EP | 1851248 A0 | 8/2006 |
| EP | 2057190 A0 | 2/2008 |
| EP | 2236156 A2 | 10/2010 |
| WO | WO 93/04699 A1 | 3/1993 |
| WO | WO9806431 A2 | 2/1998 |
| WO | WO 98/28001 | 7/1998 |
| WO | WO0022093 A2 | 4/2000 |
| WO | WO0024417 A1 | 5/2000 |
| WO | WO0136487 A2 | 5/2001 |
| WO | WO0155215 A1 | 8/2001 |
| WO | WO 02/066649 | 8/2002 |

(Continued)

OTHER PUBLICATIONS

Vajdos et al. (2002), J. Mol. Biol., vol. 320, pp. 415-428.*
Holm et al. (2007), Mol. immunol., vol. 44, pp. 1075-1084.*
Chen et al. (1999), J. Mol. Biol., vol. 293, pp. 865-881.*
Wu et al., (1999), J. Mol. Biol., vol. 294, pp. 151-162.*
Rudikoff et al., (1982), Proc. Natl. Acad. Sci. USA., vol. 79, pp. 1979-1983.*
MacCallum et al., (1996), J. Mol. Biol., vol. 262, pp. 732-745.*
Pascalis et al. , (2002), The Journal of imm., vol. 169, pp. 3076-3084.*
Casset et al., (2003), BBRC, vol. 307, pp. 198-205.*
Ngo et al. (1994), The Protein Folding Problem and tertiary Structure Prediction, pp. 492-495.*
Wells. (1990), Biochemistry, vol. 26, No. 37, pp. 8509-8517.*

(Continued)

*Primary Examiner* — Christine J Saoud
*Assistant Examiner* — Jegatheesan Seharaseyon
(74) *Attorney, Agent, or Firm* — Elaine T. Sale; Leigh W. Thorne

(57) ABSTRACT

The present invention provides humanized anti-human IFN-α monoclonal antibodies useful for therapeutic applications in humans. Preferred antibodies are humanized versions of murine antibodies ACO-1 and ACO-2, as well as variants thereof.

2 Claims, 13 Drawing Sheets

FOREIGN PATENT DOCUMENTS

| WO | WO 02/067760 | 9/2002 |
|---|---|---|
| WO | WO 2005/059106 | 6/2005 |
| WO | WO 2006/037247 | 4/2006 |
| WO | WO 2006/086586 | 8/2006 |
| WO | WO 2008/021976 | 2/2008 |

OTHER PUBLICATIONS

Chuntharapai, Anan et al., Cytokine, 2001, vol. 15, part 5, pp. 250-260.
Lazar, Greg A. et al., Molecular Immunology, 2007, vol. 44, Part 8, pp. 1986-1998.
Wu, H. et al., Journal of Molecular Biology, 1999, vol. 294, Part 1, pp. 151-162.
Kashmiri et al., Methods, 2005, vol. 36, pp. 25-34.
Blanco et al., Science, 2001, vol. 294, pp. 1540-1543.
Santiago-Raber et al., Journal of Experimental Medicine, 2003, vol. 197, Part 6, pp. 777-788.
Adolf et al., "Production of monoclonal antibodies to human IFN-alpha and their use . . . ," J. Cell Physiol. Suppl. (1982), pp. 61-68, vol. 2.
Alexenko et al., "Reconstruction of an epitope capable of binding murine monoclonal antibodies NK2 . . . ," Biochem. Biophys. Res. Commun. (1990), pp. 1061-1067, vol. 29.
Alexenko et al., "Mapping of an epitope of human leukocyte alpha interferon A which is recognized by the . . . antibody NK2," Biomed. Sci. (1991), pp. 403-409, vol. 2.
Alkan and Braun, "Epitope mapping of human recombinant interferon alpha . . . by monoclonal antibodies," Ciba Found. Symp. (1986) pp. 264-278, vol. 119.
Andersson et al., "Application of four anti-human interferon-alpha monoclonal antibodies for immunoassay . . . ," J. Interferon Res. (1991) pp. 53-60, vol. 11.
Andzhaparidze et al., "Preparation of hybridomas producing monoclonal antibodies against human interferon," Acta Virol. (1988) pp. 481-486, vol. 32.
Baechler et al., "Interferon-inducible gene expression . . . in peripheral blood cells of patients with severe lupus," Proc. Nat'l. Acad. Sci. USA (2003) pp. 2610-2615, vol. 100.
Banchereau et al., "Autoimmunity through cytokine-induced dendritic cell activation," Immunity (2004) pp. 539-550, vol. 20.
Barasoain et al., "Antibodies against a peptide representative of a conserved region of human interferon-alpha," J. Immunol. (1989) pp. 507-512, vol. 143.
Bennett et al., "Interferon and granulopoiesis signatures in systemic lupus erythematosus blood," J. Exp. Med. (2003) pp. 711-723, vol. 197.
Berg, "Identification, production, and characterization of murine monoclonal antibody (LO-22) . . . ," J. Interferon Res. (1984) pp. 481-491, vol. 4.
Bjorck, "Dendritic cells exposed to herpes simplex virus in vivo do not produce IFN-alpha after rechallenge . . . ," J. Immunol. (2004) pp. 5396-5404, vol. 172.
Blank et al., "Identification of a linear epitope of interferon-alpha 2b recognized by neutralizing monoclonal antibodies," Eur. J. Biochem. (1999) pp. 11-19, vol. 265.
Blomberg et al., "Expression of the markers BDCA-2 and BDCA-4 and production of interferon-alpha . . . ," Arthritis Rheum. (2003) pp. 2524-2533, vol. 48.
Brand et al., "Antibodies developing against a single recombinant interferon protein may neutralize many other . . . ," J. Interferon Res. (1993) pp. 121-125, vol. 13.
Braun et al., "Type I interferon controls the onset and severity of autoimmune . . . ," J. Autoimmun. (2003) pp. 15-25, vol. 20.
Chang et al., "Molecular and functional analysis of the virus and interferon-inducible human MxA promoter," Arch. Virol. (1991) pp. 1-15, vol. 117.
Crow and Kirou, "Interferon-alpha in systemic lupus erythematosus," Curr. Opin. Rheumatol. (2004) pp. 541-547, vol. 16.
Devendra and Eisenbarth, "Interferon alpha—a potential link in the pathogenesis of viral-induced type 1 diabetes and autoimmunity," Clin. Immunol. (2004) pp. 225-233, vol. 111.
Exley et al., "A comparsion of the neutralizing properties of monoclonal and polyclonal antibodies to human interferon alpha," J. Gen. Virol. (1984) pp. 2277-2280, vol. 65.
Files et al., "A novel sensitive and selective bioassay for human type I interferons," J. Interferon Cytokine Res. (1998) pp. 1019-1024, vol. 18.
Fish et al., "The role of three domains in the biological activity of human interferon-alpha," J. Interferon Res. (1989) pp. 97-114, vol. 9.
Fletcher et al., "Clinical and preclinical studies with ANA773 . . . ," Anadys Pharms., Inc., The . . . Stratton Basic Research Single Topic Conference, Atlanta, GA (Sep. 2009).
Foster et al., "IFN-alpha subtypes differentially affect human T cell motility." J. Immunol. (2004) pp. 1663-1670, vol. 173.
Goeddel et al., "The structure of eight distinct cloned human leukocyte interferon cDNAs," Nature (1981) pp. 20-26, vol. 290.
Gottleib et al., "Anti-CD4 monoclonal antibody treatment of moderate to severe psoriasis vulgaris . . . ," J. American Acad. Dermatol. (2000) pp. 595-604, vol. 43.
Gringeri et al., "Active anti-interferon alpha-immunization . . . ," J. AIDS Hum. Retrovirol. (1999) pp. 358-370, vol. 20.
Gringeri et al., "Absence of clinical, virological, and immunological signs of progression in HIV-1-infected patients . . . ," J. AIDS Hum. Retrovirol. (1996) pp. 55-57, vol. 13.
Huang et al., "Islet expression of interferon-alpha precedes diabetes in both the BB rat and . . . ," Immunity (1994) pp. 469-478, vol. 1.
Huang et al., "Interferon epxression in the pancreases of patients with Type I diabetes," Diabetes (1995) pp. 658-664, vol. 44.
Isenberg and Leckle, "Biological treatments for systemic lupus erythematosus," Scand. J. Rheumatol. (2002) pp. 187-191, vol. 31.
Kandefer-Szerszen and Lundgren, "Three separate epitopes on human interferon-alpha variants . . . ," Arch. Immunol. Ther. Exp. (Warsz.) (1992) pp. 241-246, vol. 40.
Kawade and Watanabe, "The nature of neutralization reaction between effector protein and monoclonal antibody . . . ," Immunology (1985) pp. 489-495, vol. 56.
Kirou et al., "Coordinate expression of interferon-alpha-induced genes in systemic lupus erythematosus," Arthritis & Rheumatism (2004) pp. 3958-3967, vol. 50.
Kontsek et al., "Enhancement of neutralizing efficacy by combining three monoclonal antibodies to human interferon-alpha," Immunol. (1991) pp. 8-11, vol. 73.
Maennel et al., "A rat monoclonal antibody against mouse alpha and beta interferon of all molecular weight species," Nature (1982) pp. 664-665, vol. 296.
Mathian et al., "IFN-alpha induces lethal lupus in young, pre-autoimmune . . . mice . . . ," J. Immunol. (2004) pp. 2499-2506, vol. 174.
McMullen et al., "Antipeptide antibodies against conserved regions of humans interferons-alpha . . . ," Biochem. Int'l. (1990) pp. 261-269, vol. 21.
Meager, "Natural autoantibodies to interferon," J. Interferon Cytokine Res. (1997) pp. S51-S53, vol. 17 Suppl. 1.
Meager et al., "Develoopment of interferon-specific monoclonal antibody for in vitro interferon assays," Dev. Biol. Stand, (1986) pp. 237-248, vol. 64.
Morser et al., "Production and screening of cell hybrids producing a monoclonal antibody to human interferon-alpha," J. Gen. Virol. (1981) pp. 257-265, vol. 53.
Ngo et al., "Computational complexity, protein structure predicition . . . ," In The Protein Folding Problem and Tertiary Structure Prediction (1994), pp. 491-495.
Noll et al., "Production . . . of four monoclonal antibodies specific for human interferon alpha-a and -alpha-2," Biomed. Biochim. Acta (1989) pp. 165-176, vol. 48.
Nolte et al., "Epitopes recognized by neutralizing therapy-induced human anti-interferon-alpha antibodies . . . ," Eur. J. Immunol. (1996) pp. 2155-2159, vol. 26.
Novick et al., "Monoclonal antibodies to human alpha-interferon and their use for affinity chromatography," J. Immunol. (1982) pp. 2244-2247, vol. 129.
On-line data sheet for Anti-Interferon Alpha Antibodies from Research Diagnostics, Rev. Mar. 8, 2001, http://www.researchd.com/cytokines/ifnachart.htm (printed Feb. 10, 2004).

Overall and Herzog, "Functional analysis of interferon-alpha subtypes using monoclonal antibodies . . . ," Mol. Immunol. (1992) pp. 391-399, vol. 29.

Pascual et al., "The central role of dendritic cells and interferon-alpha in SLE," Curr. Opin. Rheumatol. (2003) pp. 548-556, vol. 15.

Preble et al., "Systemic lupus erythematosus: presence in human serum of an unusual acid-labile leukocyte interferon," Science (1982) pp. 429-431, vol. 216.

Quesada and Gutterman, "Psoriasis and alpha-interferon," Lancet (1986) pp. 1466-1468, vol. 1.

Raanani et al., "Immune-mediated complication during interferon therapy in hematological patients," Acta Haematol. (2002) pp. 133-144, vol. 107.

Rabinovitch, "An update on cytokines in the pathogenesis of insulin-dependent diabetes mellitus," Diabetes/ Metabolism Reviews (1998) pp. 129-151, vol. 14.

Reyes and Klimpel, "Interferon alpha/beta synthesis during acute graft-versus-host disease," Transplantation (1987) pp. 412-416, vol. 43.

Roennblom et al., "Role of natural interferon-alpha producing cells (plasmacytoid dendritic cells) in autoimmunity," Autoimmunity (2003) pp. 463-472, vol. 36.

Roennblom and Alm, "An etiopathologic role for the type I IFN system in SLE," Trends Immunol. (2001) pp. 427-431, vol. 22.

Roennblom and Alm, "A pivotal role for the natural interferon alpha-producing cells (plasmacytoid dendritic cells) in . . . lupus," J. Exp. Med. (2001) pp. F59-F63, vol. 194.

Sattayasai et al., "Universal antibodies to human interferon-alpha subtypes . . . ," J. Interferon Res. (1991) pp. 41-48, vol. 11.

Sattayasai et al., "Subtype-specificity of antipeptide antibodies raised against unique sequences of human interferons-alpha," Mol. Immunol. (1991) pp. 975-983, vol. 28.

Schattner et al., "Review: interferons and autoimmunity," Am J. Med. Sci. (1988) pp. 532-544, vol. 295.

Schmid et al., "The Type I Interferon System is Locally Activated in Psoriatic Lesions," J. Interferon Res. (1994) pp. 229-234, vol. 14.

Shearer et al., "Monoclonal antibodies that distinguish between subspecies of human interferon-alpha . . . ," J. Immunol. (1984) pp. 3096-3101, vol. 133.

Skurkovich et al., "Anticytokine therapy—new approach to the treatment of autoimmune and cytokine-disturbance diseases," Med. Hypotheses (2002) pp. 770-780, vol. 59.

Skurkovich et al., "The use of antibodies to cytokines . . . is an effective method for the treatment of rheumatic diseases . . . ," Cytokine (1997) p. 899, vol. 9.

Skurkovich et al., "Lymphocytes' cytotoxicity towards cells of human lymphoblastoid lines in patients . . . ," Annals of Allergy (1977) pp. 344-350, vol. 39.

Staehelin et al., "Production of hybridomas secreting monoclonal antibodies to the human leukocyte interferons," Proc. Nat'l. Acad. Sci. USA (1981) pp. 1848-1852, vol. 78.

Stewart et al., "Neutralizing interferon alpha as a therapeutic approach to autoimmune diseases," Cytokine Growth Factor Rev. (2003) pp. 139-154, vol. 14.

Taylor-Papadimitriou et al., "Epitopes of human interferon-alpha defined by the reaction of monoclonal antibodies . . . ," J. Immunol. (1987) pp. 3375-3381, vol. 139.

Tsukui et al., "A monoclonal antibody with broad reactivity to human interferon-alpha subtypes . . . ," Microbiol. Immunol. (1986) pp. 1129-1139, vol. 30.

Vancova et al., "The carboxyterminal domains of human IFN-alpha(2) and IFN-alpha(8) are antigenically homologous," J. Interferon Cytokine Res. (2000) pp. 455-461, vol. 20.

Viscomi et al., "Antigenic characterization of recombinant, lymphoblastoid, and leukocyte IFN-alpha . . . ," J. Interferon Cytokine Res. (1999) pp. 319-326, vol. 19.

Weber et al., "Single amino acid changes that render human IFN-alpha(2) biologically active on mouse cells," EMBO J. (1987) pp. 591-598, vol. 6.

Wells et al., "Activity of mutational effects of proteins," Biochemistry (1990) pp. 8509-8517, vol. 26.

Casset et al., "A peptide mimetic of an anti-CD4 monoclonal antibody by rational design," Biochem. Biophys. Res. Comm. (2003) pp. 198-205, vol. 307.

Chen et al., "Selection and anaoysis of an optimized anti-VEGF antibody: crystal structure . . . ," J. Mol. Biol. (1999) pp. 865-881, vol. 293.

DePascalis et al., "Grafting of 'abbreviated' complementarity-determining regions containing specificity-determining residues . . . ," J. Immunol. (2002) pp. 3076-3084, vol. 169.

Holm et al., "Functional mapping and single chain construction of the anti-cytokeratin 8 monoclonal antibody TS1," Mol. Immunol. (2007) pp. 1075-1084, vol. 44.

MacCallum et al., "Antibody-antigen interactions; contact analysis and binding site topography," J. Mol. Biol. (1996) pp. 732-745, vol. 262.

Rudikoff et al., "Single amino acid substitution altering antigen-binding specificity," Proc. Nat'l. Acad. Sci. USA (1982) pp. 1979-1983, vol. 79.

Vajdos et al., "Comprehensive functional maps of the antigen-binding site of an anti-ErbB2 antibody . . . ," J. Mol. Biol. (2002) pp. 415-428, vol. 320.

Office Action mailed Nov. 5, 2010, in copending U.S. Appl. No. 11/883,961.

Office Action mailed Aug. 19, 2010 in copending U.S. Appl. No. 12/367,030.

Notice of Allowance mailed Oct. 6, 2010 for copending U.S. Appl. No. 12/367,030.

Bissonnette et al., "A randomized, double-blind, placebo-controlled, pase I study of MEDI-545, an anti-interferon-alfa monoclonal antibody, in subjects with chronic psoriasis," J. Am. Acad. Dermatol., 2010, pp. 427-436, vol. 62.

Boyman et al., "Spontaneous development of psoriasis in a new animal model shows an essential role for resident T cells and tumor necrosis factor-[alpha ]," J. Exp. Med., 2004, pp. 731-736, vol. 199.

Chaudhari et al., "Efficacy and safety of infliximab monotherapy for plaque-type psoriasis: a randomised trial," Lancet, 2001, pp. 1842-1847, vol. 357.

Colamonici and Domanski, "Identification of a novel subunit of the type I interferon receptor localized to human chromosome 21," J. Biol. Chem., 1993, pp. 10895-10899, vol. 268.

Criste et al., "Pharmacokinetics and Immunogenicity of sifalimumab, an anti-interferon-A monoclonal antibody, administered subcutaneously in systemic lupus erythematosus," Abstract THU0434 presented at EULAR 2011 Conference May 2011.

Crow, "Interferon alpha: a new target for therapy in systemic lupus erythematosus?," Arthritis Rheum., 2003, pp. 2396-2401, vol. 48.

Dzionek et al , "BDCA-2, a novel plasmacytoid dendritic cell-specific type II C-type lectin, mediates antigen capture and is a potent inhibitor of interferon [alpha]/[beta] induction," J. Exp. Med., 2001, pp. 1823-1834, vol. 194.

Gringeri et al., "A randomized, placebo-controlled, blind anti-AIDS clinical trial: safety and immunogenicity of a specific anti-INF[alpha ] immunization," J. AIDS, 1994, pp. 978-988, vol. 7.

Lipscomb and Masten, "Dendritic cells: immune regulators in health and disease," Physiol. Rev., 2002, pp. 97-130, vol. 82.

McKenna et al., "Plasmacytoid dendritic cells: linking innate and adaptive immunity," J. Virol., 2005, pp. 17-27, vol. 79.

Mease et al., "Etanercept in the treatment of psoriatic arthritis and psoriasis: a randomized trial," Lancet, 2000, pp. 385-390, vol. 356.

Merrill et al., "Results of a randomized, placebo-controlled, phase 2A study of sifalimumab, an anti-interferon-alpha monoclonal antibody, administered subcutaneously in subject with systemic lupus erythematosus," Abstract THU0411 presented at EULAR 2011 Conference May 2011.

Murphy, "PDC-derived interferon-alpha is a master cytokine in psoriasis development," Nature Clin. Practice Rheum., 2005, p. 9, vol. 1.

Nestle and Gilliet, "Defining upstream elements of psoriasis pathogenesis: an emerging role for interferon [alpha]," J. Invest. Dermatol., pp. xiv-xv, vol. 125.

Petri et al., "Sifalimumab, a fully human anti-interferon-alpha monoclonal antibody, in subjects with systemic lupus erythematosus (SLE): results of a phase 1B . . . study," Abstract OPO169 presented at EULAR 2011 Conference May 2011.

Schellekens et al., "Oromucosal interferon therapy: relationship between antiviral activity and viral load," J. Interferon and Cytokine Res., 2001, pp. 575-581, vol. 21.

Van Der Fits et al., "In psoriasis lesional skin the Type I interferon signaling pathway is activated, whereas interferon-alpha sensitivity is unaltered," J. Invest. Dermatol., 2004, pp. 51-60, vol. 122.

Wollenberg et al., "Plasmacytoid dendritic cells: a new cutaneous dendritic cell subset with distinct role in inflammatory skin diseases," J. Invest. Dermatol., 2002, pp. 1096-1102, vol. 119.

Yao et al., "Type I interferon: potential therapeutic target for psoriasis?," PLOS One, 2008, pp. 1-14, vol. 3 (publicaton e2737).

Office Action mailed May 10, 2011, for copending U.S. Appl. No. 11/883,961, filed Aug. 8, 2007.

* cited by examiner

A

Heavy Chain

```
         1               2               3               4               5               6
12 345678901234567890123456789012345ABC 7890123456 78901ABCDEF7890
QVQLQQPGAELVKPGASVKLSCKASGYTFTNYWMH--WVKQRPGQGLEWIGEINP--SHGRTIYN  ACO-1_VH
QVQLVQSGAEVKKPGASVKVSCKASGYTFTRYYMH--WVRQAPGQGLEWMGIINP--SGGSTSYA  VH1_46
QVQLVQSGAEVKKPGASVKVSCKASGYTFTNYWMH--WVRQAPGQGLEWMGEISP--SHGRTIYA  hzACO-1_VH 7           8                9           10                11
1234567890AB 12345678901234567890123 4567890ABCDEF12 4567890  <- Kabat
ENFKSKATLTVDKSSITAFMQLSSLTSEDSAVYFCARGGLSPA       WFAYWGQGTLVTVSA  ACO-1_VH
QKFQGRVTMTRDTSTSTVYMELSSLRSEDTAVYYCAR/            /YFDYWGQGTLVTVSS  VH1_46/JH4
QKFQGRVTMTRDTSTSTYMELSSLRSEDTAVYYCARGGLSPA        WFAYWGQGTLVTVSS  hzACO-1_VH
```

B

Light Chain

```
         1               2                 3              4              5              6
12 345678901234567890123 4567ABCDEF89012345 6789012345 6789012345678 90
QIVLTQSPAIMSASPGEKVTLTCSAGSS-----VDSSYLYWYQQKPGSSPKLWIYSTSNLASGVPA  ACO-1_VL
EIVLTQSPATLSLSPGERATLSCRASQ      SVSSYLAWYQQKPGQAPRLLIYSTSNLASGV    VKIII_L6/JK2
EIVLTQSPATLSLSPGERATLSCSAGSS-----VDSSYLYWYQQKPGQAPRLLIYSTSNLASGIPA hzACO-1_VL 7              8              9          10
1234567890 12345678901234567 890ABCDEF 7890123456789  <- The Kabat Scheme
SFSGSGSGTSYSLTISSMEAEDAASYFCHQWSSYP  FTFGSGTKLEIKR  ACO-1_VL
RFSGSGSGTDFTLTISSLEPEDFAVYYCQQSHSP    YTFGQGTKLEIK   VKIII_L6/JK2
RFSGSGSGTDFTLTISSLEPEDFAVYYCHQWSSYP  FTFGQGTKLEIKR  hzACO-1_VL
```

Heavy Chain
```
         1         2         3          4         5         6
123456789012345678901234567890123 45AB 6789012345678 9012ABC4567890
QVQLQQPGAELVKPGASVKLSCKASGYTFTSYWMH  WVKQRPGQGLEWIGEINP SNGRTEYN  ACO-1 VH
QVQLQQPGAELVKPGASVKLSCKASGYSFTSYWMH  WVKQRPGQGLEWIGEINP SNGRTEYN  ACO-2 VH
QVQLQQPGAELVKPGASVKLSCKASGYTFTSYWMH  WVKQRPGQGLEWIGEINP SNGKTEYN  J558.33 (germ-
line)

7         8          9        10              11
12345678901234567890123ABC45678901234567890ABCDEFGHIJK1234567890  <- Kabat
EKFKSKATLTVDKSSSTAYMQLSSLTSEDSAVYYCARGGLGFAWF        AYWGQGTLVTVSA  ACO-1 VH
EKFKSKATLTVDKSSSTVYMQLSSLTSEDSAVYYCARGGLGFAWF        AYWGQGTLVTVSV  ACO-2 VH
EKFKSKATLTVDKSSSTAYMQLSSLTSEDSAVYYC/   /AWF          AYWGQGTLVTVS
J558.33/DF/JH3_1
```

B

Light Chain
```
         1         2         3          4         5         6
1234567890123456789012 3456 7ABCDEF 8901234567890123456789012345678 90
QIVLTQSPAIMSASPGEKVTLTCSASS       VSSSYLYWYQQKPGSSPKLWIYSTSNLASGVPA  ACO-1 VL
QIVLTQSPAIMSASPGEKVTMTCSASS       VSSSYLYWYQQKPGSSPKLWIYSTSNLASGVPA  ACO-2 VL
QIVLTQSPAIMSASPGEKVTLTCSASS       VSSSYLYWYQQKPGSSPKLWIYSTSNLASGVPA  ae4 (germline)

7         8         9        10
123456789012345678901234567890 12345AB 6789012345678  <- The Kabat Scheme
RFSGSGSGTSYSLTISSMEAEDAASYYCHQWSSYP   FTFGSGTKLEIKR   ACO-1 VL
RFSGSGSGTSYSLTISSMEAEDAASYYCHQWSSYP   FTFGSGTKLEIKR   ACO-2 VL
RFSGSGSGTSYSLTISSMEAEDAASYYCHQWSSYP//  FTFGSGTKLEIKR  ae4/ JK4_1 (germline)
```

Black: germline sequence
Grey: somatic hyper mutations

Heavy Chain

```
             1          2          3           4          5          6
    1234567890123456789012345678901234 5ABC6789012345678 9012ABC34567890
    QVQLQQPGAELVKPGASVKLSCKASGYTFTYWMH WVKQRPGQGLEWIGEINP SHGRTYN         ACO-1 VH
    QVQLQQPGAELVKPEASVKLSCKASGYTFTNWMH WVKQRPGQGLEWIGEINP SHGRTYN         ACO-2 VH
    QVQLVQSGAEVKKPEASVKVSCKASGYTFTNWMH WVRQAPGQGLEWMGEINP SHGRTIYA        hzACO-1 VH 7          8           9          10                       11
    1234567890123456789012ABC34567890123456 7890ABCDEFGHIJK1234567890   <-- Kabat
    ENFKSKATLTVDKSSAPWQLSSLTSEDSAVYFCARDGLGPAWF              AYWGQGTLVTVSA ACO-1 VH
    ENFKSKATLTVDKSSTVYMQLSSLTSEDSAVYYCARDGLGPAWF             AYWGQGTLVTVSV ACO-2 VH
    QKFQGRVTMTRDTSTSTVYMELSSLRSEDTAVYYCARDGLGPAWF            AYWGQGTLVTVSS hzACO-1 VH
```

B

Light Chain

```
             1          2           3            4          5          6
    12345678901234567890123 4567ABCDEF8901234567890123456789 012345 67890
    QIVLTQSPAIMSASPGEKVTLTCSAGSS     VDSSYLYWYQQKPGSSPKLWIYSTSNLASGVPA    ACO-1 VL
    QIVLTQSPAIMSASPGEKVTLTCSAGSS     VDSSYLYWYQQKPGSSPKLWIYSTSNLASGVPA    ACO-2 VL
    EIVLTQSPATLSLSPGERATLSCSAGSS     VDSSYLYWYQQKPGQAPRLLIYSTSNLASGIPA    hzACO-1 VL 7            8          9           10
    12345678901234567890123456789 012345ABC6789012345678 9   <-- The Kabat Scheme
    RFSGSGSGTSYSLTISSMEAEDAASYFCHQWSSYP FTFGSGTKLEIKR       ACO-1 VL
    RFSGSGSGTSYSLTISSMEAEDAASYFCHQWSSYP FTFGSGTKLEIKR       ACO-2 VL
    RFSGSGSGTDFTLTISSLEPEDFAVYYCHQWSSYP FTFGQGTKLEIKR       hzACO-1 VL
```

▓ : residues mutated to ACO2 residues in hz-ACO1

Fig. 3

A
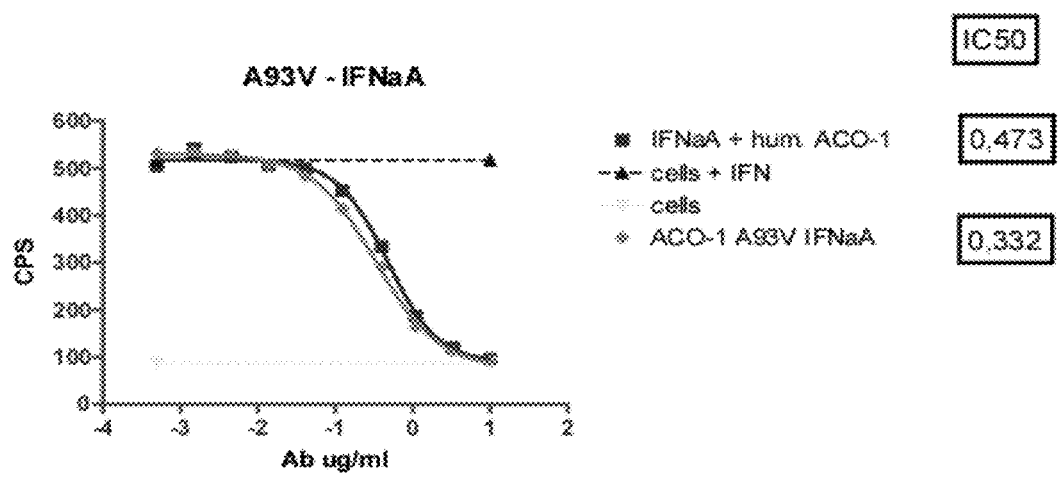
B
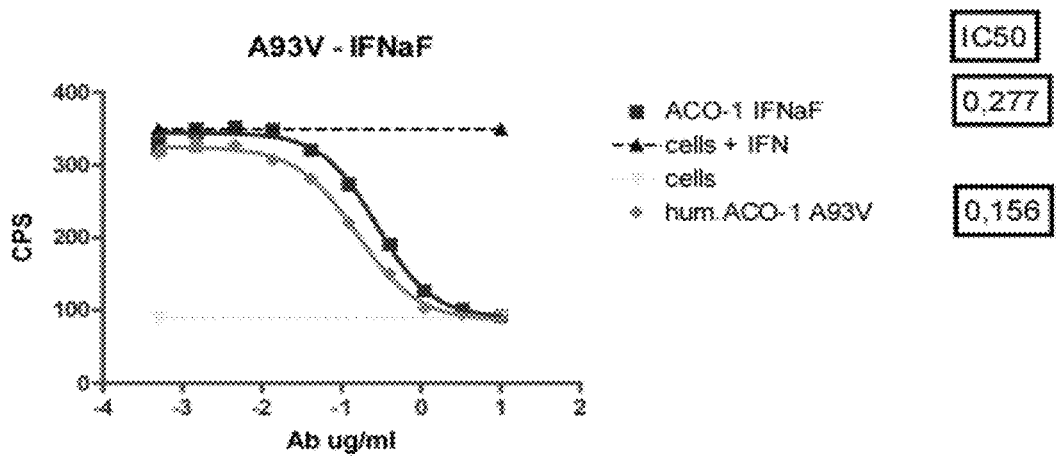
Fig. 6

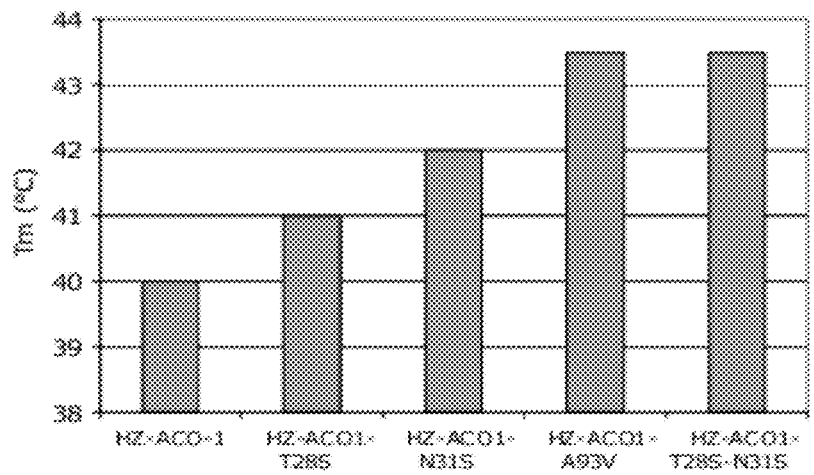
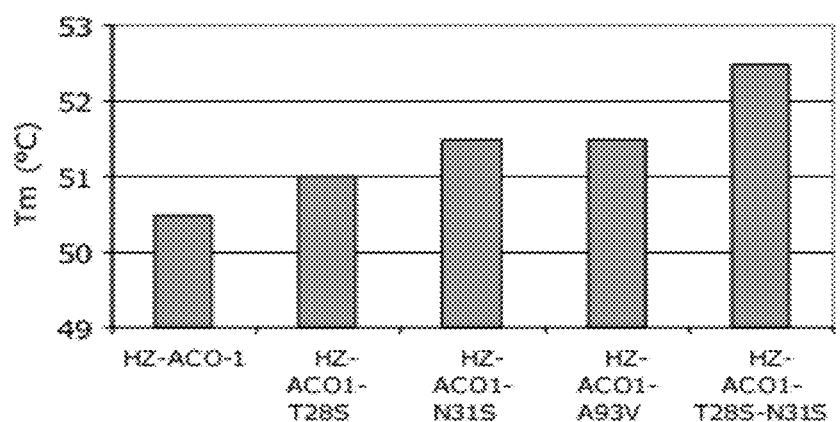
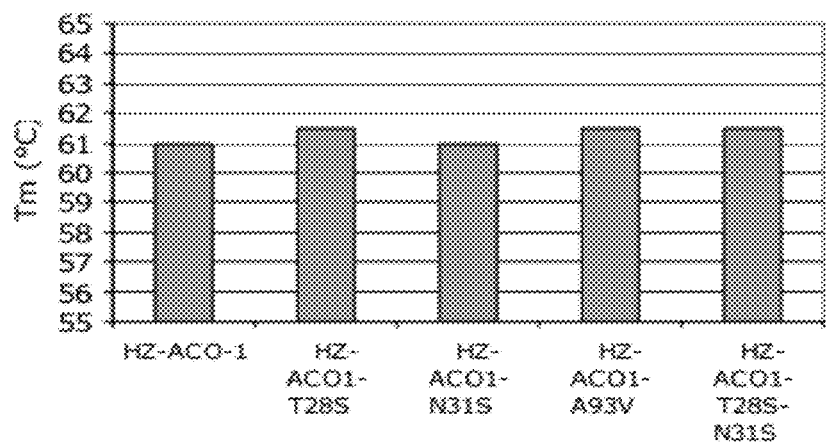
Fig. 7

```
            1                                                   50
IFN-a2   (1) CDLPQTHSLGSRRTLMLLAQMRRISLFSCLKDRHDFGFPQEEFGN-QFQK
  IFNAR1     ~~~~~~~~~~~~~~~~~~~~~~~~~~~~~~~~~~~~~~~~~~~~~~~~~
  IFNAR2     ~~~~~~~~~~~~~~~~~~~~~~~~~▓-■-■-▓~~~~~~~~~~~~~~
  hzACO-1    
IFN-a8   (1) CDLPQTHSLGNRRALILLAQMRRISPFSCLKDRHDFEFPQEEFDDKQFQK 51                                                 100
IFN-a2  (50) AETIPVLHEMIQQIFNLFSTKDSSAAWDETLLDKFYTELYQQLNDLEACV
  IFNAR1     ~~~~~~~~~■-■-■~■~~~~~~~~~~■~~~~▓-▓~~~~~~~~~~~~
  IFNAR2     ~~~~~~~~~~~~~~~~~~~~~~~~~~~~~~~~~~~~~~~~~~~~~~~~~
  hzACO-1         *      *                              *
IFN-a8  (51) AQAISVLHEMIQQTFNLFSTKDSSAALDETLLDEFYIELQQQLNDLESCV 101                                                150
IFN-a2 (100) IQGVGVTETPLMKEDSILAVRKYFQRITLYLKEKKYSPCAWEVVRAEIMR
  IFNAR1     ~~~~~~~~~~~~~~~~~~~~~~~~~~~~~~~~~~~~~~~~~~~~~~~~~
  IFNAR2     ~~~~~~~~~~~~~~~~~~~~~~~~~~~~~~~~~~~~~~~~~■■~■
  hzACO-1              *    * **    *
IFN-a8 (101) MQEVGVIESPLMYEDSILAVRKYFQRITLYLTEKKYSSCAWEVVRAEIMR 151      166
IFN-a2 (150) SFSLSTNLQES-----
  IFNAR1     ~~~~~~~~~~~
  IFNAR2     --■-----------
  hzACO-1
IFN-a8 (151) SFSLSINLQKRLKSKE
```

Figure 9

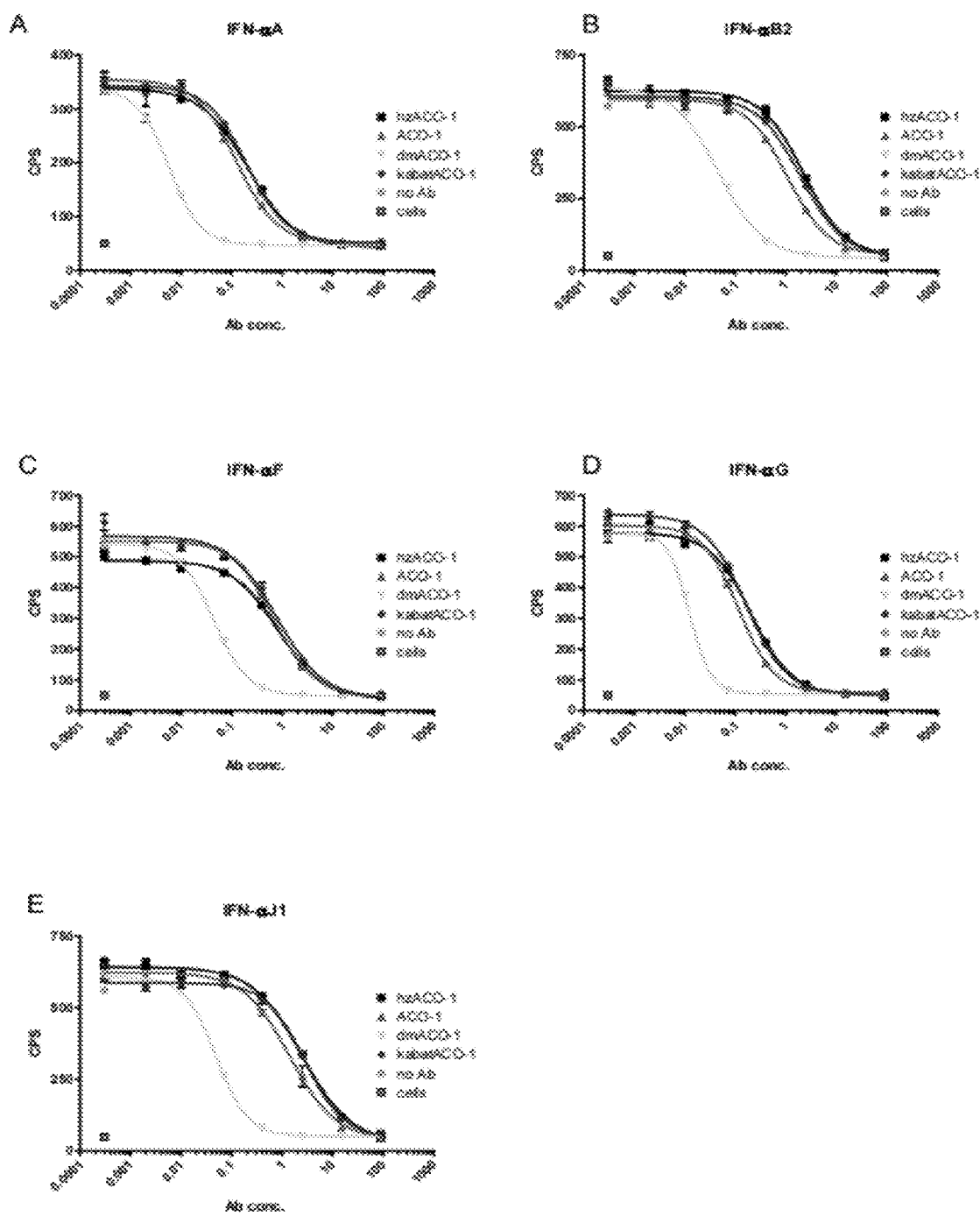
Figur 10

SEQUENCE LISTING

```
<160> NUMBER OF SEQ ID NOS: 32

<210> SEQ ID NO 1
<211> LENGTH: 119
<212> TYPE: PRT
<213> ORGANISM: mus musculus

<400> SEQUENCE: 1

Gln Val Gln Leu Gln Gln Pro Gly Ala Glu Leu Val Lys Pro Gly Ala
1               5                   10                  15
```

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Glu Ile Asn Pro Ser His Gly Arg Thr Ile Tyr Asn Glu Asn Phe
50                  55                  60

Lys Ser Lys Ala Thr Leu Thr Val Asp Lys Ser Ser Ile Thr Ala Phe
65                  70                  75                  80

Met Gln Leu Ser Ser Leu Thr Ser Glu Asp Ser Ala Val Tyr Phe Cys
                85                  90                  95

Ala Arg Gly Gly Leu Gly Pro Ala Trp Phe Ala Tyr Trp Gly Gln Gly
                100                 105                 110

Thr Leu Val Thr Val Ser Ala
            115

<210> SEQ ID NO 2
<211> LENGTH: 113
<212> TYPE: PRT
<213> ORGANISM: Homo Sapiens

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Tyr Trp Gly Gln Gly Thr Leu Val Thr Val Ser
                100                 105                 110

Ser

<210> SEQ ID NO 3
<211> LENGTH: 119
<212> TYPE: PRT
<213> ORGANISM: artificial
<220> FEATURE:
<223> OTHER INFORMATION: Humanized murine sequence

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ser His Gly Arg Thr Ile Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

```
Ala Arg Gly Gly Leu Gly Pro Ala Trp Phe Ala Tyr Trp Gly Gln Gly
            100                 105                 110

Thr Leu Val Thr Val Ser Ser
            115

<210> SEQ ID NO 4
<211> LENGTH: 109
<212> TYPE: PRT
<213> ORGANISM: Mus Musculus

<400> SEQUENCE: 4

Gln Ile Val Leu Thr Gln Ser Pro Ala Ile Met Ser Ala Ser Pro Gly
1               5                   10                  15

Glu Lys Val Thr Leu Thr Cys Ser Ala Gly Ser Ser Val Asp Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Phe Thr Phe Gly Ser Gly Thr Lys Leu Glu Ile Lys Arg
            100                 105

<210> SEQ ID NO 5
<211> LENGTH: 107
<212> TYPE: PRT
<213> ORGANISM: Homo Sapiens

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Thr Phe Gly Gln Gly Thr Lys Leu Glu Ile Lys
            100                 105

<210> SEQ ID NO 6
<211> LENGTH: 109
<212> TYPE: PRT
<213> ORGANISM: artificial
<220> FEATURE:
<223> OTHER INFORMATION: Humanized sequence

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Ser Ala Gly Ser Ser Val Asp Ser Ser
            20                  25                  30
```

```
Tyr Leu Tyr Trp Tyr Gln Gln Lys Pro Gly Gln Ala Pro Arg Leu Leu
            35                  40                  45

Ile Tyr Ser Thr Ser Asn Leu Ala Ser Gly Ile Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys His Gln Trp Ser Ser Tyr Pro
                 85                  90                  95

Phe Thr Phe Gly Gln Gly Thr Lys Leu Glu Ile Lys Arg
            100                 105

<210> SEQ ID NO 7
<211> LENGTH: 119
<212> TYPE: PRT
<213> ORGANISM: Mus musculus

<400> SEQUENCE: 7

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Ser Phe Thr Ser Tyr
             20                  25                  30

Trp Met His Trp Val Lys Gln Arg Pro Gly Gln Gly Leu Glu Trp Ile
            35                  40                  45

Gly Glu Ile Asn Pro Ser His Gly Arg Thr Ser Tyr Asn Glu Asn Phe
 50                  55                  60

Lys Ser Lys Ala Thr Leu Thr Val Asp Lys Ser Ser Asn Ile Val Tyr
 65                  70                  75                  80

Met Gln Leu Ser Ser Leu Thr Ser Glu Asp Ser Ala Val Tyr Tyr Cys
                 85                  90                  95

Val Arg Gly Gly Leu Gly Pro Ala Trp Phe Ala Tyr Trp Gly Gln Gly
            100                 105                 110

Thr Leu Val Thr Val Ser Val
            115

<210> SEQ ID NO 8
<211> LENGTH: 113
<212> TYPE: PRT
<213> ORGANISM: homo sapiens

<400> SEQUENCE: 8

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ala Trp Phe Ala Tyr Trp Gly Gln Gly Thr Leu Val Thr Val
            100                 105                 110

Ser
```

<210> SEQ ID NO 9
<211> LENGTH: 109
<212> TYPE: PRT
<213> ORGANISM: mus musculus

<400> SEQUENCE: 9

Gln Ile Val Leu Thr Gln Ser Pro Ala Ile Met Ser Ala Ser Pro Gly
 1               5                  10                  15

Glu Lys Val Thr Leu Thr Cys Ser Ala Gly Ser Ser Val Gly Ser Ser
             20                  25                  30

Tyr Phe Tyr Trp Tyr Gln Gln Lys Pro Gly Ser Ser Pro Lys Leu Trp
         35                  40                  45

Ile Tyr Gly Thr Ser Asn Leu Ala Ser Gly Val Pro Ala Arg Phe Ser
     50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Ser Ser Tyr Pro
                 85                  90                  95

Phe Thr Phe Gly Ser Gly Thr Lys Leu Glu Ile Lys Arg
            100                 105

<210> SEQ ID NO 10
<211> LENGTH: 109
<212> TYPE: PRT
<213> ORGANISM: homo sapiens

<400> SEQUENCE: 10

Gln Ile Val Leu Thr Gln Ser Pro Ala Ile Met Ser Ala Ser Pro Gly
 1               5                  10                  15

Glu Lys Val Thr Leu Thr Cys Ser Ala Ser Ser Ser Val Ser Ser Ser
             20                  25                  30

Tyr Leu Tyr Trp Tyr Gln Gln Lys Pro Gly Ser Ser Pro Lys Leu Trp
         35                  40                  45

Ile Tyr Ser Thr Ser Asn Leu Ala Ser Gly Val Pro Ala Arg Phe Ser
     50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Ser Ser Tyr Pro
                 85                  90                  95

Phe Thr Phe Gly Ser Gly Thr Lys Leu Glu Ile Lys Arg
            100                 105

<210> SEQ ID NO 11
<211> LENGTH: 19
<212> TYPE: DNA
<213> ORGANISM: artificial
<220> FEATURE:
<223> OTHER INFORMATION: Primer

<400> SEQUENCE: 11
ctgggccagg tgctggagg                                              19

<210> SEQ ID NO 12
<211> LENGTH: 25
<212> TYPE: DNA
<213> ORGANISM: artificial
<220> FEATURE:
<223> OTHER INFORMATION: Primer

<400> SEQUENCE: 12
ctaacactca ttcctgttga agctc                                        25

```
<210> SEQ ID NO 13
<211> LENGTH: 414
<212> TYPE: DNA
<213> ORGANISM: mus musculus

<400> SEQUENCE: 13
atgggatgga gctatatcat gctcttttg gtagcaacag ctacagatgt ccactcccag      60
gtccaactgc agcagcctgg ggctgaactg gtgaagcctg ggcttcagt gaagctgtcc     120 tgtaaggctt ctggctacac cttcaccaac tactggatgc actgggtgaa gcagaggcct    180
ggacaaggcc ttgagtggat tggagagatt aatcctagcc acggtcgtac tatctacaat    240
gaaaacttca gagcaaggc cacactgact gtagacaaat cctccatcac agccttcatg     300
caactcagca gcctgacatc tgaggactct gcggtctatt tctgtgcaag agggggactg    360
ggacccgcct ggtttgctta ctggggccaa gggactctgg tcactgtctc tgca          414

<210> SEQ ID NO 14
<211> LENGTH: 393
<212> TYPE: DNA
<213> ORGANISM: mus musculus

<400> SEQUENCE: 14 atggatttc aagtgcagat tttcagcttc ctgctaatca gtgtctcagt cataatgtcc      60
agaggacaaa ttgttctcac ccagtctcca gcaatcatgt ctgcttctcc tggggagaag    120
gtcaccttga cctgcagtgc cggctcaagt gtagattcca gctatttgta ctggtaccag    180
cagaagccag atcctccccc caaactctgg atttatagca catccaacct ggcttctgga    240
gtccctgctc gcttcagtgg cagtgggtct gggacctctt actctctcac aatcagcagc    300
atggaggctg aagatgctgc ctcttatttc tgccatcagt ggagtagtta cccattcacg    360
ttcggctcgg ggacaaaatt ggaaataaaa cgg                                 393

<210> SEQ ID NO 15
<211> LENGTH: 5
<212> TYPE: PRT
<213> ORGANISM: mus musculus

<400> SEQUENCE: 15

Asn Tyr Trp Met His
1               5

<210> SEQ ID NO 16
<211> LENGTH: 17
<212> TYPE: PRT
<213> ORGANISM: mus musculus

<400> SEQUENCE: 16

Glu Ile Asn Pro Ser His Gly Arg Thr Ile Tyr Asn Glu Asn Phe Lys
1               5                   10                  15

Ser

<210> SEQ ID NO 17
<211> LENGTH: 10
<212> TYPE: PRT
<213> ORGANISM: mus musculus

<400> SEQUENCE: 17

Gly Gly Leu Gly Pro Ala Trp Phe Ala Tyr
1               5                   10
```

```
<210> SEQ ID NO 18
<211> LENGTH: 12
<212> TYPE: PRT
<213> ORGANISM: mus musculus

<400> SEQUENCE: 18

Ser Ala Gly Ser Ser Val Asp Ser Ser Tyr Leu Tyr
1               5                   10

<210> SEQ ID NO 19
<211> LENGTH: 7
<212> TYPE: PRT
<213> ORGANISM: mus musculus

<400> SEQUENCE: 19

Ser Thr Ser Asn Leu Ala Ser
1               5

<210> SEQ ID NO 20
<211> LENGTH: 9
<212> TYPE: PRT
<213> ORGANISM: mus musculus

<400> SEQUENCE: 20

His Gln Trp Ser Ser Tyr Pro Phe Thr
1               5

<210> SEQ ID NO 21
<211> LENGTH: 17
<212> TYPE: PRT
<213> ORGANISM: artificial
<220> FEATURE:
<223> OTHER INFORMATION: Humanized murine sequence

<400> SEQUENCE: 21

Glu Ile Asn Pro Ser His Gly Arg Thr Ile Tyr Ala Gln Lys Phe Gln
1               5                   10                  15

Gly

<210> SEQ ID NO 22
<211> LENGTH: 5
<212> TYPE: PRT
<213> ORGANISM: mus musculus

<400> SEQUENCE: 22

Ser Tyr Trp Met His
1               5

<210> SEQ ID NO 23
<211> LENGTH: 17
<212> TYPE: PRT
<213> ORGANISM: mus musculus

<400> SEQUENCE: 23

Glu Ile Asn Pro Ser His Gly Arg Thr Ser Tyr Asn Glu Asn Phe Lys
1               5                   10                  15

Ser

<210> SEQ ID NO 24
<211> LENGTH: 12
<212> TYPE: PRT
<213> ORGANISM: mus musculus

<400> SEQUENCE: 24
```

Ser Ala Gly Ser Ser Val Gly Ser Ser Tyr Phe Tyr
1               5                   10

<210> SEQ ID NO 25
<211> LENGTH: 7
<212> TYPE: PRT
<213> ORGANISM: mus musculus

<400> SEQUENCE: 25

Gly Thr Ser Asn Leu Ala Ser
1               5

<210> SEQ ID NO 26
<211> LENGTH: 35
<212> TYPE: DNA
<213> ORGANISM: artificial
<220> FEATURE:
<223> OTHER INFORMATION: Primer

<400> SEQUENCE: 26
ctagctagct catttacccg gagaccggga gatgg                              35

<210> SEQ ID NO 27
<211> LENGTH: 31
<212> TYPE: DNA
<213> ORGANISM: artificial
<220> FEATURE:
<223> OTHER INFORMATION: Primer

<400> SEQUENCE: 27
gctctaacac tcattcctgt tgaagctctt g                                  31

<210> SEQ ID NO 28
<211> LENGTH: 414
<212> TYPE: DNA
<213> ORGANISM: Mus musculus

<400> SEQUENCE: 28
atgggatgga gctatatcat cctcttttg gtagcagcag ctacagatgt ccactcccag    60
gtccaactgc agcagcctgg ggctgaactg gtgaagcctg ggcttcagt gaagctgtcc    120 tgcaaggcct ctggctacag cttcaccagc tactggatgc actgggtgaa gcagaggcct   180
ggacaaggcc ttgagtggat tggagagatt aatcctagcc acggtcgtac tagctacaat   240
gagaacttca gagcaaggc cacactgact gtagacaaat cctccaacat agtctacatg    300
caactcagca gcctgacatc tgaggactct gcggtctatt actgtgtaag aggggggactg   360 ggacccgcct ggtttgctta ctggggccaa gggactctgg tcactgtctc tgta          414

<210> SEQ ID NO 29
<211> LENGTH: 393
<212> TYPE: DNA
<213> ORGANISM: Mus musculus

<400> SEQUENCE: 29
atggattttc aagtgcagat tttcagcttc ctgctaatca gtgtctcagt cataatgtcc    60
agaggacaaa ttgttctcac ccagtctcca gcaatcatgt ctgcatctcc tggggagaag   120
gtcaccttga cctgcagtgc cggctcaagt gtaggttcca gctacttta ctggtaccag     180 cagaagccag atcctccccc caaactctgg atttatggca catccaacct ggcttctgga   240
gtccctgctc gcttcagtgg cagtgggtct gggacctctt actctctcac aatcagcagc   300
atggaggctg aagatgctgc ctcttatttc tgccatcagt ggagtagtta tccattcacg   360
ttcggctcgg ggacaaaatt ggaaataaaa cgg        393

<210> SEQ ID NO 30
<211> LENGTH: 166
<212> TYPE: PRT
<213> ORGANISM: homo sapiens

<400> SEQUENCE: 30

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 31
<211> LENGTH: 220
<212> TYPE: PRT
<213> ORGANISM: artificial
<220> FEATURE:
<223> OTHER INFORMATION: Humanized sequence

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ser His Gly Arg Thr Ile Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Gly Pro Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys
            210                 215                 220

<210> SEQ ID NO 32
<211> LENGTH: 215
<212> TYPE: PRT
<213> ORGANISM: artificial
<220> FEATURE:
<223> OTHER INFORMATION: Humanized sequence

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Ser Ala Gly Ser Ser Val Asp Ser Ser
                20                  25                  30

Tyr Leu Tyr Trp Tyr Gln Gln Lys Pro Gly Gln Ala Pro Arg Leu Leu
            35                  40                  45

Ile Tyr Ser Thr Ser Asn Leu Ala Ser Gly Ile Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Ser Tyr Pro
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

HUMANIZED ANTIBODIES AGAINST HUMAN INTERFERON-ALPHA

CROSS-REFERENCE TO RELATED APPLICATIONS

This application is a 35 U.S.C. §371 national stage application of International Patent Application PCT/EP2009/055448 (NOT YET PUBLISHED), filed Jun. 4, 2009, which claimed priority of European Patent Application EP 08103847.3, filed May 7, 2008; this application further claims priority under 35 U.S.C. §119 of U.S. Provisional Application 61/056,193, filed May 27, 2008.

FIELD OF THE INVENTION

The present invention relates to humanized antibodies against human interferon alpha (IFN-α) and their use in treating or preventing various diseases and disorders in human patients.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Oct. 23, 2009. The Sequence Listing is made up of 21 kilobytes, and the information contained in the attached "SEQUENCE LISTING" is identical to the information in the specification as originally filed. No new matter is added.

BACKGROUND OF THE INVENTION

Based on a variety of different observations, interferon alpha (IFN-α) is a cytokine believed to be involved in a number of autoimmune diseases. Although systemic lupus erythomatosus (SLE) patients often do not have measurable serum levels of IFN-α, they appear to have a clear IFN-α gene signature. In addition, induction of dendritic cell (DC) maturation by treatment of DCs with SLE patient serum can be inhibited by an anti-IFN-α antibody. It has also been shown that knockout of the IFN-α/β receptor in New Zeeland Black (NZB) mice having an SLE phenotype results in a near normal phenotype (Santiago-Raber et al., J Exp Med. 2003; 197(6):777-88).

Antibodies against IFN-α have therefore been suggested as tools to neutralize the activity of this cytokine for the treatment of such autoimmune diseases, alone or in combination. Specific murine antibodies (ACO-1 to ACO-6) that recognize a wide range of different IFN-α subtypes were generated and characterized as described in the international patent application published as WO20060086586. However, murine antibodies are not suitable for use in humans because of their immunogenicity, and it is therefore desirable to generate humanized antibodies where the murine CDRs are grafted onto a human scaffold antibody. However humanized antibodies often suffer from functional deficiencies as compared to the murine parent, such as, e.g., a lower affinity and/or stability and/or undesirable immunogenicity. Such deficiencies in humanized antibodies can in some cases be compensated for by making one or a few back point mutations. It is usually desirable to perform no or only a very few back point mutations since the presence of too many back mutations tend to result in undesirable low stability and/or an undesirable degree of immunogenicity. The provision of a safe and stable humanized anti-IFN-α antibody having desirable biological properties such as e.g. retaining affinity and potency of the humanized anti-IFN-α antibody to a large number of IFN-α subtypes is thus desirable.

There is thus a need in the art for humanized anti-IFN-α antibodies having desirable features with respect to features such e.g. stability, specificity, safety, immunogenicity, etc. Furthermore, there is a need in the art for efficient methods for producing such antibodies.

SUMMARY OF THE INVENTION

In a first aspect, the present invention relates to a humanized antibody that specifically binds human interferon-α (IFN-α), or an antigen-binding fragment thereof, which humanized antibody is a humanized version of murine antibody ACO-1 or ACO-2, or of a combination thereof, comprising fewer donor amino acid residues than the murine complementary determining regions (CDRs) according to Kabat.

In another aspect, the present invention furthermore relates to a humanized antibody that specifically binds IFN-α, or an antigen-binding fragment thereof, wherein said antibody is capable of binding IFN-α subtypes A, 2, B2, C, F, G, H2, I, J1, K, 4a, 4b and WA, but not subtypes 1 or D, and wherein said antibody comprises fewer donor amino acid residues than the non-human CDRs according to Kabat.

The present invention furthermore relates to methods for obtaining such antibodies as well as use of such antibodies for therapeutic purposes and compositions comprising such antibodies.

The antibodies according to the present invention can be suitable for treatment of various inflammatory diseases.

DESCRIPTION OF THE DRAWINGS

FIG. 1 shows analysis of murine ACO-1 VH (A) and VL (B) sequences for humanization (hz=humanized), where the mask is shown in shaded text, Kabat CDRs are shown in bold, differences between the mouse sequence and the human germline sequence are shown in underlined text, potential somatic hypermutated residues are shown in bold underlined text, and potential back-mutation residues in shaded underlined text. ACO-1 VH=SEQ ID NO:1; human germline VH1_46/JH4=SEQ ID NO:2; hzACO-1 VH=SEQ ID NO:3; ACO-1 VL=SEQ ID NO:4; human germline VKIII_L6/JK2=SEQ ID NO:5; hzACO-1 VL=SEQ ID NO:6.

FIG. 2 shows an alignment between ACO-1 and ACO-2 VH (A) and VL (B) sequences, as well as the corresponding mouse germline sequences. ACO-2 VH=SEQ ID NO:7; mouse germline J558.33/D_/JH3_1=SEQ ID NO:8; ACO-2 VL=SEQ ID NO:9; mouse germline ae4/JK4_1=SEQ ID NO:10.

FIG. 3 shows the location of ACO-2 residues selected for introduction into hzACO-1.

FIG. 6 shows an RG assay comparison of hzACO-1 with a hzACO-1 variants having the single ACO-2-derived mutation A93V, using IFN-αA (A) or IFN-αF (B). Data calculations were made as described for FIG. 5.

FIG. 7 shows transition temperatures for hzACO-1 and variants at pH 3.5 (A), 4.5 (B), and 5.5 (C), without additives.

FIG. 9 shows the IFN-α8 binding epitopes for IFNAR1 and IFNAR2 (Quadt-Akabayov S. R. et al. Protein Sci. 15, 2656-2668, 2006 and Roisman L. C et al. J. Mol. Biol. 353, 271-281, 2005), as indicated by colored boxes below the IFN-α8 sequence. Residues indicated by boxes colored gray are partly conserved among all IFN-α subtypes while residues indicated by black colored boxes are fully conserved. The hzACO-1 binding epitope, using a 4 Å distance cut-off, on IFN-α8 is indicated by "*" above the amino acid sequence of IFN-α8.

FIG. 10 shows comparison of the mouse ACO-1 mAb to hzACO-1 as well as two variants hereof in the RG assay. One variant is a humanized ACO-1 harboring the entire CDRH2 (designated hzACO-1-kabat CDRH2) whereas the hzACO-1 was constructed with a shorter CDRH2 as described in example 2. in addition the figure shows another mutated hzACO-1 which has been optimized for interaction with IFN-αs (hzACO-1 Y32E, T30R) through rational design. These four recombinant mAb variants were compared with respect to inhibition of five different representative IFN-α subtypes, as indicated.

DESCRIPTION OF THE INVENTION

Figure 4:
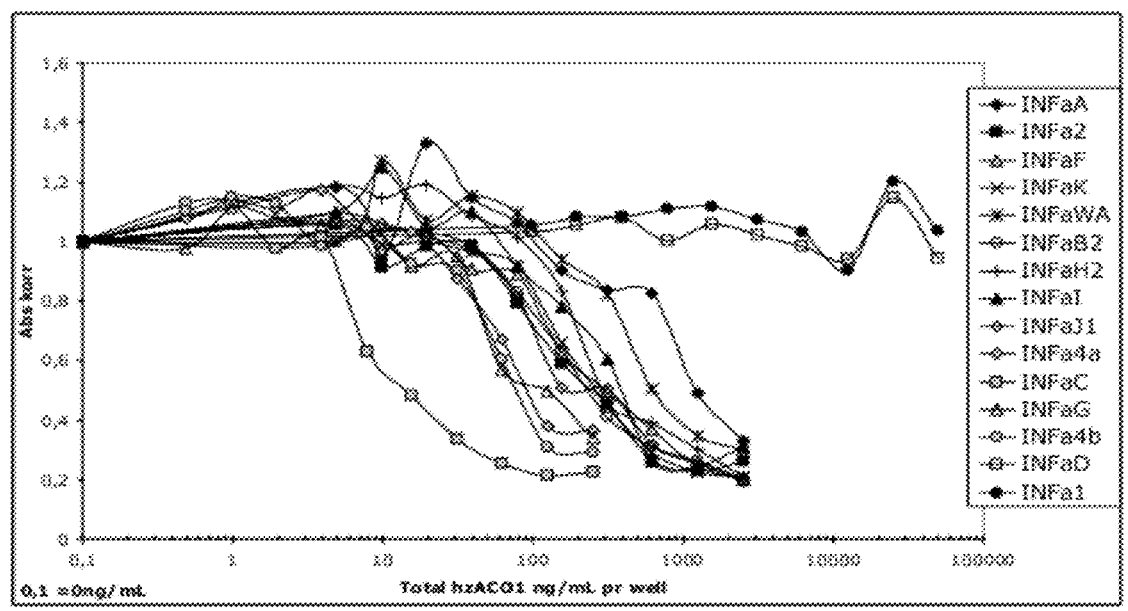
FIG. 4 shows hzACO-1 inhibition of the protective effect of all interferon subtypes tested except for IFN-αD and IFN-α1 in a CPE assay.

The present invention is based, in part, on anti-IFN-α antibodies with properties suitable for treating human patients suffering from an IFN-α-related condition or disease, such as, e.g., a lupus disease or disorder such as, e.g., SLE; graft versus host disease; type 1 diabetes, AIDS, autoimmune thyroiditis, psoriasis, juvenile dermatomyositis, and Sjögren's syndrome. The antibodies are typically based on humanized versions of the murine ACO-1 and/or ACO-2 antibodies.

ACO-1 and ACO-2 were identified as capable of blocking the bioactivity of thirteen recombinant IFN-α subtypes as well as two complex mixtures of IFN-produced upon viral infection (see WO2006086586). ACO-1 and ACO-2 also consistently blocked the bioactivity of serum from SLE patients that exhibited IFN-α signatures by microarray analysis. ACO-1 and ACO-2 did not significantly neutralize the bioactivity of IFN-α protein subtypes D and 1, but did neutralize the IFN-α bioactivity of SLE serum. Though not limited to theory, it is therefore possible that subtypes D and 1 are not significantly involved in the etiology of SLE.

As described in the Examples, structural modelling of the variable regions revealed that it was possible to humanize ACO-1 and ACO-2 using fewer donor (murine) residues than the Kabat CDRs, thus further reducing the risk for an adverse immune response in a human patient. The analysis also identified advantageous sites for back-mutations. It was further discovered that, possibly due to the high sequence similarity between the ACO-1 and ACO-2 variable regions (differing only at 13 sites), certain amino acid residues in the humanized ACO-1 (hzACO-1) sequence could be replaced by ACO-2 residues at the corresponding position. Within CDR regions, mutations can normally be made without rendering the antibody sequence less human. This humanization procedure resulted in improved functional properties such as affinity, stability, expression level and IFN-α-inhibitory activity of the humanized antibody.

In a humanized ACO-1 antibody, exemplary mutations in the hzACO-1 VH (SEQ ID NO:3) include V5Q, T28S, M69L, R71V, T73K, S76I, S76N, T77I, V78A, Y79F and A93V, as well as any combination thereof, using Kabat numbering. Exemplary mutations in the hzACO-1 VL (SEQ ID NO:6) include E1Q, D29G, L33F, L47W, 55OG, I58V, and F71Y, as well as any combination thereof. In one embodiment, the hzACO-1 VH region comprises a mutation selected from T28S, N31S, and A93V. In another embodiment, the hzACO-1 VH region comprises a mutation selected from T28S, N31S, and A93V, and any combination thereof, such as, e.g., T28S and N31S, T28S and A93V, and N31S and A93V. In another embodiment, the hzACO-1 VH region comprises a mutation selected from T28S, N31S, and A93V, or a combination thereof, such as, e.g., T28S and N31S, T28S and A93V, or N31S and A93V; and at least one additional mutation.

DEFINITIONS

To facilitate the understanding of this invention, a number of terms are defined below.

"ACO-1 and ACO-2 antibodies" are characterized and described in WO20060086586. ACO-1 is deposited with ATCC accession no. PTA-6557 (WO2006086586) and ACO-2 is deposited as ATCC accession No. PTA-7778 (WO2008021976). The antibodies according to the present invention are humanized variants of ACO-1 and ACO-2. However, the humanized versions of ACO-1 and ACO-2 according to the present invention do not comprise the full length murine Kabat sequences. In a preferred embodiment, at least one of the CDR sequences comprise a truncation of about 3-10 amino acids, preferably 3-8, more preferably 4-7 amino acids. The antibody preferably comprises a truncation in the CDR H2, said CDR H2 preferably being truncated by 3-10, preferably 3-8, more preferably 4-7, and most preferably by 6 amino acids. And it furthermore follows that occasional point mutations may be introduced in one or more CDR sequences as well as within the human scaffold antibody. The term "ACO-1 and ACO-2 antibodies" may however furthermore embrace any IFN-α antibody capable of binding IFN-αsubtypes A, 2, B2, C, F, G, H2, I, J1, K, 4a, 4b and WA, but not subtypes 1 or D. It should however be understood that ACO-1 and ACO-2 as such may be perceived as only one antibody since the differences in their CDR sequences are only a few amino acids. It is plausible that that ACO-1 and ACO-2 thus represent two stages of in vivo somatic hyper-mutation of the same antibody. An ACO-1/ACO-2 antibody according to the present invention is thus a humanized antibody comprising CDR sequences having at least 90% identity with the CDR sequences of ACO-1 and ACO-2, more preferably at least 92%, and most preferably at least 95%.

The terms: "CDR truncation", "forward mutation", and "shortening of CDRs" may be used interchangeably throughout the document. In connection with the present invention such terms generally refer to the fact that CDR-truncation may be perceived as a number of forward mutations in a row—meaning that a shortened murine CDR fragment can be grafted onto the human framework. While it may not be surprising that grafting of shorter CDRs tend to result in antibodies with reduced degree of immunogenicity, it is actually surprising that other advantageous features of the humanized antibody may be retained such as e.g. stability, specificity, etc. "Back mutations" always refer to mutations in the framework (i.e. not in the CDRs)—and back mutations are typically introduction of one or more "murine" amino acid residue at selected sites e.g. in order to stabilise the antibody structure.

The term "interferon alpha" (IFN-α), as used herein, refers to a family of proteins that include some of the main effectors of innate immunity. There are at least 15 known subtypes of human IFN-α. The names of the IFN-α protein subtypes and corresponding encoding genes are listed below in Table 1.

TABLE 1

IFN-α protein subtypes and genes

| IFN-α protein subtype | Corresponding IFN-α gene |
|---|---|
| A | 2a |
| 2 | 2b |
| B2 | 8 |
| C | 10 |
| D (Val$^{114}$) | 1 |
| F | 21 |
| G | 5 |
| H2 | 14 |
| I | 17 |
| J1 | 7 |
| K | 6 |
| 4a | 4a |
| 4b | 4b |
| WA | 16 |
| 1 (Ala$^{114}$) | 1 |

See Pestka et al. (1997) "Interferon Standardization and Designations" J Interferon Cytokine Res 17: Supplement 1, S9-S14. IFN-αB2 is sometimes also referred to as IFN-αB, and is not to be confused with IFN-β. Natural IFN-α from leukocytes (leukocyte IFN-), as well as recombinant human IFN-α protein subtypes are available from PBL Biomedical Labs, Piscataway, N.J. (interferonsource.com). Natural IFN-α is a complex mixture of IFN-α subtypes. Methods for detecting and quantifying these interferons, such as ELISA and RIA, are known in the art.

The term "antibody" herein is used in the broadest sense and specifically includes full-length monoclonal antibodies, polyclonal antibodies, and, unless otherwise stated or contradicted by context, antigen-binding fragments, antibody variants, and multispecific molecules thereof, so long as they exhibit the desired biological activity. Generally, a full-length antibody is a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarily determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

An "antigen-binding fragment" of an antibody is a molecule that comprises a portion of a full-length antibody which is capable of detectably binding to the antigen. Antigen-binding fragments include multivalent molecules comprising one, two, three, or more antigen-binding portions of an antibody, and single-chain constructs wherein the VL and VH regions, or selected portions thereof, are joined by synthetic linkers or by recombinant methods to form a functional, antigen-binding molecule.

The terms "antibody derivative" and "immunoconjugate" are used interchangeably herein to denote molecules comprising a full-length antibody or an antigen-binding fragment thereof, wherein one or more amino acids are chemically modified, e.g., by alkylation, PEGylation, acylation, ester formation or amide formation or the like, e.g., for linking the antibody to a second molecule. Exemplary modifications include PEGylation, cysteine-PEGylation, biotinylation, radiolabelling, and conjugation with a second agent, such as a detectable or cytotoxic agent.

A "multispecific molecule" comprises an antibody, or an antigen-binding fragment thereof, which is associated with or linked to at least one other functional molecule (e.g. another peptide or protein such as another antibody or ligand for a receptor) to generate a molecule that binds to at least two different binding sites or target molecules. Exemplary multispecific molecules include bi-specific antibodies and antibodies linked to soluble receptor fragments or ligands.

A "humanized" antibody is a human/non-human chimeric antibody that contains a minimal sequence (CDR regions) derived from non-human immunoglobulin. Humanized antibodies are thus human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, FR residues of the human immunoglobulin are replaced by corresponding non-human residues. Furthermore, humanized anti-bodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin.

The term "hypervariable region" when used herein refers to the amino acid residues of an antibody that are responsible for antigen binding. The hypervariable region generally comprises amino acid residues from a "complementarity-determining region" or "CDR" (residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Framework region" or "FR" residues are those VH or VL residues other than the CDRs as herein defined.

"Corresponding" amino acid positions in two substantially identical amino acid sequences are those aligned by any of the protein analysis software referred to herein, typically using default parameters.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

The terms, "selectively neutralizes" and "selectively neutralizing", as used herein, refer to an isolated and purified antibody (such as, but not limited to a monoclonal antibody), or an antigen-binding fragment thereof, that neutralizes selectively at least about 40%, at least about 50%, or at least about 60% of a bioactivity of one or more IFN-α protein subtypes, but does not significantly neutralize at least one bioactivity of another IFN-α protein subtype, wherein the bioactivity can be, e.g., activation of the MxA promoter and/or antiviral activity.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The phrase "IFN-α-related condition or disease" as used herein, refers to an abnormal condition, disease, or pre-clinical disease state that has been linked with elevated levels of IFN-α in a patient's serum. Examples of such include, but are not limited to, lupus diseases or disorders such as SLE, graft versus host disease (GVHD), type 1 diabetes, AIDS (caused by human immunodeficiency virus (HIV)), autoimmune thyroiditis, and psoriasis. Methods for determining the level of IFNα are known in the art.

Humanized Anti-IFN-α Antibodies

The antibodies of the invention are humanized version of the anti-IFN-α mouse antibodies ACO-1 or ACO-2, variants thereof, and/or antigen-binding fragments thereof, characterized by particular functional and/or structural features or properties. Recombinant antibodies can be produced in suitable host cell lines by standard techniques and be characterized by various assays to evaluate their functional activities, as described below. In fact, it turns out that IFN-alpha antibodies according to the present invention may be produced with a significantly improved yield compared to IFN-alpha antibodies that were humanized in a traditional way.

According to the so-called "best-fit" method, the sequence of the variable domain of a rodent antibody is screened against a library of such known human variable-domain sequences or libraries of human germline sequences. The human sequence that is closest to that of the rodent can then be accepted as the human framework region for the humanized antibody (Sims et al., J. Immunol. 1993; 151:2296 et seq.; Chothia et al, Chothia and Lesk, J. Mol. Biol 1987; 196:901-917). Another method uses a particular framework region derived from the consensus sequence of all human antibodies of a particular subgroup of light or heavy chains. The same framework may be used for several different humanized antibodies.

Preferred framework sequences for use in the antibodies of the invention are those that are structurally similar to the framework sequences used by ACO-1 or ACO-2. Thus, in one embodiment, the invention provides a humanized ACO-1 or ACO-2 antibody comprising VH framework residues derived from a human VH1_46 gene and a human JH4 gene, and VL framework residues derived from a human VKIII_L6 gene and a human JK2 gene, and specifically binds human IFN-α.

Example 1 below describes the design of an exemplary humanized ACO-1 antibody, hzACO-1, comprising such framework sequences.

Functional Properties

The humanized antibodies of the invention bind specifically to IFN-α subtypes A, 2, B2, C, F, G, H2, I, J1, K, 4a, 4b, and WA (Table 2). In one embodiment, a humanized ACO-1 or ACO-2 antibody of the invention binds to an IFN-α protein subtype such as IFN-αA with high affinity, for example with a KD of about $10^{-7}$ M or less, a KD of about $10^{-8}$ M or less, a KD of about $5 \times 10^{-9}$ M or less, or a KD of about $2 \times 10^{-9}$ M or less. In one embodiment, the humanized antibody is a hzACO-1 variant which binds to IFN-αA, IFN-αF, and/or another IFN-α protein subtypes with an affinity comparable to or higher than that of hzACO-1.

TABLE 2

Kinetic parameters of hzACO-1 for a range of human IFN-α subtypes

| Sample | ka (1/Ms) | kd (1/s) | KD (M) |
|---|---|---|---|
| hIFN-αA | 2.97E+05 | 3.94E−04 | 1.33E−09 |
| hIFN-α1 | No binding | — | — |
| hIFN-α2 | 3.58E+05 | 3.51E−04 | 9.81E−10 |
| hIFN-α4b | 3.74E+05 | 6.22E−04 | 1.67E−09 |
| hIFN-αG | 4.63E+05 | 4.26E−04 | 9.20E−10 |
| hIFN-αH2 | 3.78E+05 | 1.21E−03 | 3.21E−09 |

TABLE 2-continued

Kinetic parameters of hzACO-1 for
a range of human IFN-α subtypes

| Sample | ka (1/Ms) | kd (1/s) | KD (M) |
|---|---|---|---|
| hIFN-αI | 7.23E+05 | 2.03E-03 | 2.81E-09 |
| hIFN-αJ1 | 6.81E+05 | 3.27E-03 | 4.81E-09 |
| hIFN-αWA | 7.09E+05 | 2.91E-03 | 4.10E-09 |
| hIFN-α4a | 3.33E+04 | 1.15E-04 | 3.45E-09 |
| hIFN-αC | 7.19E+05 | 7.53E-04 | 1.05E-09 |
| hIFN-αK | 5.74E+05 | 8.27E-04 | 1.44E-09 |

For example, the ratio between the KD of the hzACO-1 variant and the KD of hzACO-1 to a IFN-αA protein subtype can be about 1.0, about 0.8, about 0.7, or about 0.6. In another embodiment, the humanized antibody is a hzACO-1 variant which binds to IFN-αA, IFN-αF, and/or another IFN-α protein subtype with an affinity comparable to or higher than that of recombinantly produced ACO-1. In another embodiment, the humanized antibody is a hzACO-1 variant which binds to IFN-αA, IFN-αF, and/or another IFN-α protein subtypes with an affinity comparable to or higher than that of hybridoma-produced ACO-1.

Furthermore, the humanized antibodies of the invention are capable of selectively neutralizing a bioactivity of one or more IFN-α protein subtypes. For example, a humanized ACO-1 or ACO-2 variant can be capable of selectively neutralizing at least about 40%, at least about 50%, or at least about 60% of a bioactivity of IFN-α protein subtypes A, 2, B2, C, F, G, H2, I, J1, K, 4a, 4b, or WA, or any combination thereof, as compared to a control. In a particular embodiment, the humanized antibody does not significantly neutralize the bioactivity of IFN-α subtypes D and/or 1. Exemplary bioactivities include, but are not limited to, activation of the M×A promoter, antiviral activity, or both. The ability of a humanized antibody to neutralize such IFN-αbioactivity can be evaluated using, e.g., the reporter gene (RG) an cytopathic inhibition (CPE) assays described herein. In one embodiment, the humanized antibody is a hzACO-1 variant which has an 1050 comparable to or lower than the 1050 of hzACO-1 in an RG assay. In a specific embodiment, the hzACO-1 variant has a lower 1050 than hzACO-1 in an RG assay.

In one embodiment, the humanized antibodies of the invention compete with and/or bind to the same epitope on an IFN-α protein subtype as ACO-1 and/or ACO-2. Such antibodies can be identified based on their ability to cross-compete with ACO-1 and/or ACO-2 in standard IFN-α binding assays as described herein. The ability of a test humanized antibody to inhibit the binding of ACO-1 or ACO-2 to one or more IFN-α protein subtypes demonstrates that the test antibody can compete with ACO-1 or ACO-2 for binding to IFN-α and thus can bind to the same epitope on the IFN-α protein subtype as ACO-1 and/or ACO-2 (WO02066649 and WO2005059106). In a particular embodiment, the humanized antibody binds to a different human IFN-α epitope than any of the murine monoclonal antibodies 9F3, and MMHA-1, -2, -3, -6, -8, -9, -11, -13, and -17 (PBL Biomedical Laboratories, NJ, USA) and/or human monoclonal antibodies 13H5, 13H7, and 7H9, and/or cross-competes more with ACO-1 or ACO-2 than with one or more of the listed murine and human monoclonal antibodies.

In one embodiment, hzACO-1, hzACO-2, hzACO-1 variants or hzACO-2 variants provided by the invention have an immunogenicity comparable to or lower than that of a humanized ACO-1 or ACO-2 antibody comprising murine CDRs according to Kabat (Kabat ACO-1). Immunogenicity of a humanized antibody can be evaluated by, e.g., one or more of the methods described in Wadwha et al., Dev Biol (Basel). 2005; 122:155-70), which is hereby incorporated by reference in its entirety.

In further aspect, the humanized antibodies of the invention are stable in a formulation suitable for administration to a human patient. In one embodiment, the humanized ACO-1 or ACO-2 antibody according to the invention is at least as stable as the IFN-alpha antibodies humanized in a traditional way comprising the full length murine Kabat sequences. Stability of an antibody can be evaluated using known methods in the art, including the thermaflour analyses described in Example 11.

Preferred humanized antibodies of the invention exhibit at least one, more preferably two, three, four, five or more, of the following properties: (a) bind specifically to IFN-α subtypes A, 2, B2, C, F, G, H2, I, J1, K, 4a, 4b, and WA; (b) selectively neutralize one or more bioactivities of IFN-α protein subtypes A, 2, B2, C, F, G, H2, I, J1, K, 4a, 4b, or WA; any combination thereof, or all thereof; (c) do not significantly neutralize a bioactivity of IFN-α1 or D; (d) compete with and/or bind to the same epitope on an IFN-α protein subtype as ACO-1 and/or ACO-2; (e) compete more with ACO-1 or ACO-2 than with any of 9F3, 13H5, 13H7, and 7H9; (f) are less likely to elicit an immune response than a hzACO-1 or hzACO-2 antibody comprising murine CDRs according to Kabat; (g) are stable in pharmaceutical formulations; and (h) binds to at least one of IFN-α protein subtypes A, 2, B2, C, F, G, H2, I, J1, K, 4a, 4b, or WA with a KD of $10^{-8}$ M or less.

Structural Properties

Preferred antibodies of the invention are humanized versions of the murine monoclonal antibodies ACO-1 and ACO-2. Such antibodies can be produced, isolated, and structurally and functionally characterized as described in the Examples. Full-length, variable region, and Kabat CDR sequences of ACO-1, hzACO-1 and ACO-2 are set forth in Table 3 and described in FIGS. 1-3.

TABLE 3

| Sequence numbering for primers, protein and antibodies | | | |
|---|---|---|---|
| Antibody portion | Sequence composition | Sequence | SEQ ID NO: |
| ACO-1 VH | Protein | | 1 |
| VH1_46/JH4 | Protein | | 2 |
| hzACO-1 VH | Protein | | 3 |
| ACO-1 VL | Protein | | 4 |
| VKIII_L6/JK2 | Protein | | 5 |
| hzACO-1 VL | Protein | | 6 |
| ACO-2 VH | Protein | | 7 |
| J558.33/D_/JH3_1 | Protein | | 8 |
| ACO-2 VL | Protein | | 9 |
| ae4/JK4_1 | Protein | | 10 |
| PCR Primer ACO-1 cloning | DNA | | 11 |
| PCR Primer ACO-1 cloning | DNA | | 12 |
| ACO-1 VH | DNA | | 13 |
| ACO-1 VL | DNA | | 14 |
| ACO-1 CDR_H1 | Protein | NYWMH | 15 |
| ACO-1 CDR_H2 | Protein | EINPSHGRTIYNENFKS | 16 |
| ACO-1 CDR_H3 | Protein | GGLGPAWFAY | 17 |
| ACO-1 CDR_L1 | Protein | SAGSSVDSSYLY | 18 |
| ACO-1 CDR_L2 | Protein | STSNLAS | 19 |
| ACO-1 CDR_L3 | Protein | HQWSSYPFT | 20 |
| hzACO-1 CDR_H2 | Protein | EINPSHGRTIY*AQKFQG* | 21 |
| ACO-2 CDR_H1 | Protein | SYWMH | 22 |
| ACO-2 CDR_H2 | Protein | EINPSHGRTSYNENFKS | 23 |
| ACO-2 CDR_L1 | Protein | SAGSSVGSSYFY | 24 |

TABLE 3-continued Sequence numbering for primers, protein and antibodies

| Antibody portion | Sequence composition | Sequence | SEQ ID NO: |
|---|---|---|---|
| ACO-2 CDR_L2 | Protein | GTSNLAS | 25 |
| PCR Primer ACO-2 cloning | DNA | | 26 |
| PCR Primer ACO-2 cloning | DNA | | 27 |
| ACO-2 VH | DNA | | 28 |
| ACO-2 VL | DNA | | 29 |
| hIFN-α8 | Protein | | 30 |
| hzACO-1 Fab HC | Protein | | 31 |
| hzACO-1 LC | Protein | | 32 |

The sequences of hzACO-1 CDR H1, H3, L1, L2, and L3 are identical to the corresponding ACO-1 sequences. ACO-2 CDR H3 and L3 are identical to the corresponding ACO-1 CDR sequences. The amino acids shown in italics in the hzACO-1 CDR_H2 sequence correspond to the human framework sequence—in traditionally humanized antibodies the full length Kabat sequence correspond to the ACO-1 CDR_H2 sequence, where all amino acids are derived from the murine antibody.

In one aspect, the invention provides humanized versions of murine ACO-1 and ACO-2 antibodies with fewer donor residues than the Kabat CDRs, i.e., fewer murine residues than a humanized ACO-1 or ACO-2 antibody produced by grafting of the kabat CDRs.

In one embodiment, the humanized antibody specifically binds human IFN-α and is a humanized version of murine antibody ACO-1 or ACO-2, or of a combination thereof, comprising fewer donor amino acid residues than the murine complementary determining regions (CDRs) according to Kabat. The CDR H2 sequence may, for example, comprise fewer donor amino acid residues than those corresponding to Kabat residues 50-65, 50-64, 50-63, 50-62, 50-61, or 50-60. The CDR H2 donor residues may comprise Kabat residues 50-59. Additionally or alternatively, the CDR H2 donor amino acid residues may consist of Kabat residues 50-59. Kabat residues 50-59 correspond to residues 1-11 of SEQ ID NOS:16, 21, and 23. In one embodiment, the remaining VH CDRs may comprise or consist of the Kabat CDRs (see FIGS. 1-3), i.e., a CDR H1 sequence comprising donor amino acid residues corresponding to Kabat residues 31-35, and a CDR H3 sequence comprising donor amino acid residues corresponding to Kabat residues 95-102.

In one embodiment, the humanized ACO-1 or ACO-2 antibody may comprise a CDR L1 comprising donor amino acid residues corresponding to Kabat residues 24-34 of the variable region of the ACO-1 light chain (VL), a CDR L2 comprising donor amino acid residues corresponding to Kabat residues 50-56 of the ACO-1 VL region, and a CDR L3 comprising donor amino acid residues corresponding to Kabat residues 89-97 of the ACO-1 VL region (SEQ ID NO:4) or ACO-2 VL region (SEQ ID NO:9). Additionally or alternatively, the antibody may comprise CDR L1 donor amino acid residues consisting of Kabat residues 24-34, CDR L2 donor residues consisting of Kabat residues 50-56, and CDR L3 donor amino acid residues consisting of Kabat residues 89-97. The corresponding amino acid sequences are shown in Table 3.

In one aspect, the invention provides specific humanized ACO-1 antibodies. The humanized ACO-1 antibody specifically binds human IFN-α, and comprises VH CDR sequences substantially identical to the sequences of Kabat residues 31-35, 50-65, and 95-102 of SEQ ID NO:3, with an optional N31S mutation. The antibody may, e.g., comprise a CDR H1 sequence comprising SEQ ID NO:15; a CDR H2 sequence comprising SEQ ID NO:21; and a CDR H3 sequence comprising SEQ ID NO:17. Additionally or alternatively, the antibody may comprise a CDR H1 sequence consisting of SEQ ID NO:15; a CDR H2 sequence consisting of SEQ ID NO:21; and a CDR H3 sequence consisting of SEQ ID NO:17. In one embodiment, the humanized ACO-1 comprises VH framework residues derived from a human VH1_46 gene and/or a human JH4 gene, preferably both. In a specific embodiment, the humanized antibody comprises a VH sequence corresponding to SEQ ID NO:3.

The humanized ACO-1 antibody may further comprise VL CDR sequences substantially identical to the sequences of Kabat residues 24-34, 50-56, and 89-97 of SEQ ID NO:6. The antibody may, e.g., comprise a CDR_L1 sequence comprising SEQ ID NO:18; a CDR_L2 sequence comprising SEQ ID NO:19; and a CDR_L3 sequence comprising SEQ ID NO:20. Additionally or alternatively, the may comprise a CDR_L1 sequence consisting of SEQ ID NO:18; a CDR_L2 sequence consisting of SEQ ID NO:19; and a CDR_L3 sequence consisting of SEQ ID NO:20. In one embodiment, the humanized ACO-1 antibody comprises VL framework residues derived from a human VKIII_L6 gene and/or a human JK2 gene, preferably both. In a specific embodiment, the humanized antibody comprises a VL sequence corresponding to SEQ ID NO:6.

In one aspect, the invention provides an antibody comprising the CDR sequences of ACO-2. The antibody can specifically bind human IFN-α and comprises VH CDR sequences substantially identical to the sequences of Kabat residues 31-35, 50-59, and 95-102 of SEQ ID NO:7. In one embodiment, the antibody comprises a CDR_H1 sequence comprising SEQ ID NO:22; a CDR_H2 sequence comprising SEQ ID NO:23; and a CDR_H3 sequence comprising SEQ ID NO:17. In an additional or alternative embodiment, the antibody comprises a CDR_H1 sequence consisting of SEQ ID NO:22; a CDR_H2 sequence consisting of SEQ ID NO:23; and a CDR_H3 sequence consisting of SEQ ID NO:17. The antibody may further comprise VL CDR sequences substantially identical to the sequences of residues Kabat residues 24-34, 50-56, and 89-97 of SEQ ID NO:9. In one embodiment, the antibody comprises a CDR_L1 sequence comprising SEQ ID NO:24; a CDR_L2 sequence comprising SEQ ID NO:25; and a CDR_L3 sequence comprising SEQ ID NO:20. Additionally or alternatively, the antibody comprises a CDR_L1 sequence consisting of SEQ ID NO:24; a CDR_L2 sequence consisting of SEQ ID NO:25; and a CDR_L3 sequence consisting of SEQ ID NO:20. The antibody may, in one aspect, be a humanized ACO-2 antibody.

A humanized ACO-1 or ACO-2 antibody may further comprise at least a portion of a human Fc-region (unless the antibody is an antigen-binding fragment not comprising any Fc-portion). Typically, the size of the Fc-region is selected to achieve the desired pharmacokinetic properties of the antibody; the larger Fc-portion, the slower clearance. In one embodiment, the humanized antibody is a full-length antibody, preferably comprising an IgG4 isotype Fc-region. In a particular embodiment, the IgG4 Fc-region comprises an S241P mutation, with numbering according to Kabat; corresponding to residue 228 per the EU numbering system (Edelman G. M. et AL., Proc. Natl. Acad. USA 63, 78-85 (1969)).

Given that both ACO-1 and ACO-2 can bind to IFN-α and are similar, the humanized VH and VL sequences can be "mixed and matched" to create other anti-IFN-α binding molecules of the invention. IFN-α binding of such "mixed and matched" antibodies can be tested using the binding assays described herein (e.g. flow cytometry, Biacore® analysis, ELISAs) and/or using one or more functional assays as described herein. Preferably, when VH and VL chains are mixed and matched, a VH sequence from a particular VH/VL pairing is replaced with a structurally similar VH sequence. Likewise, a VL sequence from a particular VH/VL pairing is preferably replaced with a structurally similar VL sequence.

Accordingly, in one aspect, the invention provides an humanized monoclonal antibody, or antigen binding portion thereof, comprising: (a) a VH region comprising ACO-1 or ACO-2 VH CDRs and (b) a VL region comprising ACO-1 or ACO-2 VL CDRs; wherein the antibody specifically binds IFN-α. Preferred heavy and light chain combinations include: (a) a VH region comprising SEQ ID NOS:15-17, optionally omitting some or all of the 5 C-terminal amino acids of SEQ ID NO:16, and (b) a light chain variable region comprising SEQ ID NOS:18-20; (a) a VH region comprising SEQ ID NOS:15-17, optionally omitting some or all of the 5 C-terminal amino acids of SEQ ID NO:16, and (b) a light chain variable region comprising SEQ ID NOS:24, 25, and 20; (a) a VH region comprising SEQ ID NOS:22, 23, and 17, optionally omitting some or all of the 5 C-terminal amino acids of SEQ ID NO:23, and (b) a light chain variable region comprising SEQ ID NOS:18-20; and (a) a VH region comprising SEQ ID NOS:22, 23, and 17, optionally omitting some or all of the 5 C-terminal amino acids of SEQ ID NO:23, and (b) a light chain variable region comprising SEQ ID NOS:24, 25, and 20. Other preferred heavy and light chain combinations include (a) a VH region comprising the sequence of SEQ ID NO:3 and (b) a VL region comprising the amino acid sequence of SEQ ID NO:4; (a) a VH comprising SEQ ID NOS:15, 21, and 17, and (b) a VL comprising SEQ ID NOS: 18-20; and (a) a VH comprising SEQ ID NOS:15, 21, and 17, and (b) a VL comprising SEQ ID NOS:24, 25, and 20.

In another aspect, the invention provides antibodies that comprise the heavy chain and light chain CDR1s, CDR2s and/or CDR3s of ACO-1 or ACO-2, or combinations thereof. Given that each of these antibodies can bind to IFN-α and that antigen-binding specificity is provided primarily by the CDR1, 2 and 3 regions, the CDR H1, H2 and H3 sequences and CDR L1, L2 and L3 sequences can be "mixed and matched" (i.e., CDRs from different antibodies can be mixed and matched, although each antibody can contain a CDR H1, H2 and H3 and a CDR L1, L2 and L3) to create other anti-IFN-α binding molecules of the invention. IFN-α-binding of such "mixed and matched" antibodies can be tested using the binding assays described below and in the Examples (e.g., flow cytometry, Biacore® analysis, or ELISAs). Preferably, when. VH CDR sequences are mixed and matched, the CDR H1, H2 and/or H3 sequence from a particular VH sequence is replaced with a structurally similar CDR sequence(s). Likewise, when VL CDR sequences are mixed and matched, the CDR L1, L2 and/or L3 sequence from a particular VL sequence preferably is replaced with a structurally similar CDR sequence(s). For example, the CDRs of ACO-1 and ACO-2 share substantial structural similarity and therefore are amenable to mixing and matching.

Accordingly, in another aspect, the invention provides a humanized monoclonal antibody, or antigen binding portion thereof comprising: (a) a CDR H1 comprising an amino acid sequence selected from the group consisting of SEQ ID NOS: 15 and 22; (b) a CDR H2 comprising an amino acid sequence selected from the group consisting of at least residues 1-12 of SEQ ID NOS:16 and 23, (c) a CDR H3 comprising SEQ ID NO:17; (d) a CDR L1 comprising an amino acid sequence selected from the group consisting of SEQ ID NOS:18 and 24; (e) a CDR L2 comprising an amino acid sequence selected from the group consisting of SEQ ID NOS:19 and 25; and (f) a CDR L3 comprising SEQ ID NO:20; wherein the antibody specifically binds IFN-α.

In a preferred embodiment, the antibody comprises: (a) a CDR H1 comprising SEQ ID NO:15; (b) a CDR H2 comprising at least residues 1-12 of SEQ ID NO:16; (c) a CDR H3 comprising SEQ ID NO:17; (d) a CDR L1 comprising SEQ ID NO:18; (e) a CDR L2 comprising SEQ ID NO:19; and (f) a CDR L3 comprising SEQ ID NO:20.

In another preferred embodiment, the antibody comprises: (a) a CDR H1 comprising SEQ ID NO: 22; (b) a CDR H2 comprising at least residues 1-12 of SEQ ID NO:23; (c) a CDR H3 comprising SEQ ID NO:17; (d) a CDR L1 comprising SEQ ID NO:24; (e) a CDR L2 comprising SEQ ID NO:25; and (f) a CDR L3 comprising SEQ ID NO:20.

In a preferred embodiment, the antibody comprises: (a) a CDR H1 comprising SEQ ID NO:15; (b) a CDR H2 comprising SEQ ID NO:21; (c) a CDR H3 comprising SEQ ID NO:17; (d) a CDR L1 comprising SEQ ID NO:18; (e) a CDR L2 comprising SEQ ID NO:19; and (f) a CDR L3 comprising SEQ ID NO:20.

In a preferred embodiment, the antibody comprises: (a) a CDR H1 comprising SEQ ID NO:22; (b) a CDR H2 comprising at least residues 1-12 of SEQ ID NO:16; (c) a CDR H3 comprising SEQ ID NO:17; (d) a CDR L1 comprising SEQ ID NO:18; (e) a CDR L2 comprising SEQ ID NO:19; and (f) a CDR L3 comprising SEQ ID NO:20.

In a preferred embodiment, the antibody comprises: (a) a CDR H1 comprising SEQ ID NO:15; (b) a CDR H2 comprising at least residues 1-12 of SEQ ID NO:16; (c) a CDR H3 comprising SEQ ID NO:17; (d) a CDR L1 comprising SEQ ID NO:24; (e) a CDR L2 comprising SEQ ID NO:19; and (f) a CDR L3 comprising SEQ ID NO:20.

In a preferred embodiment, the antibody comprises: (a) a CDR H1 comprising SEQ ID NO:15; (b) a CDR H2 comprising at least residues 1-12 of SEQ ID NO:16; (c) a CDR H3 comprising SEQ ID NO:17; (d) a CDR L1 comprising SEQ ID NO:18; (e) a CDR L2 comprising SEQ ID NO:25; and (f) a CDR L3 comprising SEQ ID NO:20.

Humanized Anti-IFN-α Antibody Variants

Though an antibody variant or derivative typically has at least one altered property as compared to the parent antibody, antibody variants or derivatives can retain one, some, most, or all of the functional properties of the patent anti-IFN-α antibody, including, but not limited to: (a) bind specifically to IFN-α subtypes A, 2, B2, C, F, G, H2, I, J1, K, 4a, 4b, and WA; (b) selectively neutralize one or more bioactivities of IFN-α protein subtypes A, 2, B2, C, F, G, H2, I, J1, K, 4a, 4b, or WA; any combination thereof, or all thereof; (c) do not significantly neutralize a bioactivity of IFN-α1 or D; (d) compete with and/or bind to the same epitope on an IFN-α protein subtype as ACO-1 and/or ACO-2; (e) compete more with ACO-1 or ACO-2 than with any of 9F3, 13H5, 13H7, and 7H9; (f) are less likely to elicit an immune response than a hzACO-1 or hzACO-2 antibody comprising murine CDRs according to Kabat; (g) are stable in pharmaceutical formulations; and (h) binds to at least one of IFN-α protein subtypes A, 2, B2, C, F, G, H2, I, J1, K, 4a, 4b, or WA with a KD of $10^{-8}$ M or less. Any combination of the above-described functional features, and/or the functional features as described in the Examples, may be exhibited by an antibody of the invention.

In certain embodiments, a humanized antibody of the invention comprises a VH region comprising CDR H1-H3 sequences and a VL region comprising CDR L1-L3 sequences, wherein one or more of these CDR sequences comprise specified amino acid sequences based on the preferred antibodies described herein; ACO-1 and ACO-2, or conservative modifications thereof, and wherein the antibodies have retained or improved the desired functional properties of the anti-IFN-α antibodies of the invention. Accordingly, the invention provides an isolated monoclonal antibody, or antigen-binding fragment thereof, comprising a heavy chain variable region comprising CDR H1, CDR H2, and CDR H3 sequences and a light chain variable region comprising CDR H1, CDR H2, and CDR H3 sequences, wherein: (a) a CDR H1 comprising an amino acid sequence selected from the group consisting of SEQ ID NOS:15 and 22, and conservative modifications thereof; (b) a CDR H2 comprising an amino acid sequence selected from the group consisting of at least residues 1-12 of SEQ ID NOS:16 and 23, and conservative modifications thereof, (c) a CDR H3 comprising SEQ ID NO:17, and conservative modifications thereof; (d) a CDR L1 comprising an amino acid sequence selected from the group consisting of SEQ ID NOS:18 and 24, and conservative modifications thereof; (e) a CDR L2 comprising an amino acid sequence selected from the group consisting of SEQ ID NOS:19 and 25, and conservative modifications thereof; and (f) a CDR L3 comprising SEQ ID NO:20, and conservative modifications thereof; wherein the antibody specifically binds IFN-α.

Thus, one or more amino acid residues within the CDR or FR regions of an antibody of the invention can be replaced with other amino acid residues from the same side chain family and the altered antibody can be tested for retained function (i.e., the functions set forth in (c), (d) and (e) above) using the functional assays described herein.

The functional properties of the antibody variants can be assessed using standard assays available in the art and/or described herein. For example, the ability of the antibody to bind IFN-α can be determined using standard binding and biological effects (e.g., reporter gene) assays, such as those set forth in the Examples (e.g., Biacore® analysis, or ELISAs).

Variable Region Modifications

In one aspect, the invention provides a humanized ACO-1 or ACO-2 antibody with mutations in the CDR or framework regions.

Specific exemplary mutations in humanized ACO-1 and their identification are described in Examples 2 and 3 (see, also FIGS. 1 and 3). These include both back-mutations; introducing ACO-1 residues into humanized ACO-1, as well as mutations where ACO-2-derived residues are introduced into humanized ACO-1. Exemplary back-mutations in the hzACO-1 VH (SEQ ID NO:3) include V5Q, M69L, R71V, T73K, S76I, and V78A, as well as any combination thereof, using Kabat numbering. Exemplary back-mutations in the hzACO-1 VL (SEQ ID NO:6) include E1Q, L47W, I58V, and F71Y, as well as any combination thereof. Exemplary ACO-2-derived mutations in the hzACO-1 VH (SEQ ID NO:3) include T28S, N31S, I58S, S76N, T77I, and A93V, as well as any combination thereof. Exemplary ACO-2 derived mutations in the hzACO-1 VL (SEQ ID NO:6) include D29G, L33F, and S50G, as well as any combination thereof.

Further, various hzACO-1 VH and VL variant sequences can be "mixed and matched" with variant sequences or parent sequences to create a library of hzACO-1 variants of the invention. IFN-α-binding of such "mixed and matched" antibodies can be tested using the binding assays described herein (e.g., Biacore® analysis, ELISAs) and/or using one or more functional assays as described herein In one embodiment, the invention provides a humanized antibody that specifically binds human IFN-α and contains a variable domain having, incorporated into a human antibody variable domain, amino acids from a donor non-human antibody that binds human IFN-α, comprising a donor antibody amino acid residue at one or more sites selected from 5, 28, 31, 58, 69, 71, 73, 76, 78, 79, and 93 in the heavy chain variable domain?

In one embodiment, the invention provides a humanized antibody that specifically binds human IFN-α and contains a variable domain having, incorporated into a human antibody variable domain, amino acids from a donor non-human antibody that binds human IFN-α, comprising a donor antibody amino acid residue at one or more sites selected from 1, 29, 33, 47, 50, 58, and 71 in the light chain variable domain.

In one embodiment, the invention provides a humanized ACO-1 antibody that specifically binds human IFN-α and contains a variable domain having, incorporated into a human antibody variable domain, CDR sequences from ACO-1 that bind human IFN-α, and further comprising ACO-2 amino acid residues at one or more sites selected from 28, 31, 58, 76, 77, 78, 79, and 93 in the heavy chain variable domain. In a specific embodiment, the ACO-2 amino acid residues are at one or more sites selected from 28, 31, and 93.

In one embodiment, the invention provides a humanized ACO-1 antibody that specifically binds human IFN-α and contains a variable domain having, incorporated into a human antibody variable domain, CDR sequences from ACO-1 that bind human IFN-α, and further comprising ACO-2 amino acid residues at one or more sites selected from 29, 33, and 50 in the light chain variable domain.

In one embodiment, the invention provides a hzACO-1 variant that specifically binds human IFN-α, and comprises VH CDR sequences substantially identical to the sequences of Kabat residues 31-35, 50-65, and 95-102 of SEQ ID NO:3, with an N31S mutation. The antibody may, e.g., comprise a CDR H1 sequence comprising SEQ ID NO:15 with an N31S mutation; a CDR H2 sequence comprising SEQ ID NO:21; and a CDR H3 sequence comprising SEQ ID NO:17. Additionally or alternatively, the antibody may comprise a CDR H1 sequence consisting of SEQ ID NO:15 with an N31S mutation; a CDR H2 sequence consisting of SEQ ID NO:21; and a CDR H3 sequence consisting of SEQ ID NO:17. In one embodiment, the humanized ACO-1 comprises VH framework residues derived from a human VH1_46 gene and/or a human JH4 gene, preferably both. In a specific embodiment, the humanized antibody comprises a VH sequence corresponding to SEQ ID NO:3, with an N to S mutation at Kabat position 31. As shown in the Examples, an N31S mutation in hzACO-1 increased the binding affinity to IFN-αA to levels comparable to that of ACO-1, and increased the stability at pH3.5 and 4.5. Moreover, since residue 31 is in a "donor" CDR residue, the mutation does not introduce a further murine residue into the hzACO-1 sequence, thus not increasing the risk for an immune response against the antibody when administered to a human. Other CDR mutations with the same advantage include D29G and S50G in the hzACO-1 VL.

In one embodiment, the invention provides a hzACO-1 variant that specifically binds human IFN-α, and comprises VH CDR sequences substantially identical to the sequences of Kabat residues 31-35, 50-65, and 95-102 of SEQ ID NO:3, with a T28S mutation. The antibody may, e.g., comprise a CDR H1 sequence comprising SEQ ID NO:15; a CDR H2 sequence comprising SEQ ID NO:21; and a CDR H3 sequence comprising SEQ ID NO:17. Additionally or alternatively, the antibody may comprise a CDR H1 sequence consisting of SEQ ID NO:15; a CDR H2 sequence consisting of SEQ ID NO:21; and a CDR H3 sequence consisting of SEQ ID NO:17. In one embodiment, the humanized ACO-1 comprises VH framework residues derived from a human VH1_46 gene, further comprising a T28S mutation. In a specific embodiment, the humanized antibody comprises a VH sequence corresponding to SEQ ID NO:3, with an T to S mutation at Kabat position 28. As shown in the Examples, a T28S mutation in hzACO-1 increased the binding affinity to IFN-αA to levels comparable to that of ACO-1, and increased stability at pH3.5 and 4.5.

In one embodiment, the invention provides a hzACO-1 variant that specifically binds human IFN-α, and comprises VH CDR sequences substantially identical to the sequences of Kabat residues 31-35, 50-65, and 95-102 of SEQ ID NO:3, with an A93V mutation. The antibody may, e.g., comprise a CDR H1 sequence comprising SEQ ID NO:15; a CDR H2 sequence comprising SEQ ID NO:21; and a CDR H3 sequence comprising SEQ ID NO:17. Additionally or alternatively, the antibody may comprise a CDR H1 sequence consisting of SEQ ID NO:15; a CDR H2 sequence consisting of SEQ ID NO:21; and a CDR H3 sequence consisting of SEQ ID NO:17. In one embodiment, the humanized ACO-1 comprises VH framework residues derived from a human VH1_46 gene and a human JH4 gene, further comprising an A93V mutation. In a specific embodiment, the humanized antibody comprises a VH sequence corresponding to SEQ ID NO:3, with an A to V mutation at Kabat position 93. As shown in the Examples, an A93V mutation in hzACO-1 increased the binding affinity to IFN-αA to levels comparable to that of ACO-1, increased the potency for inhibition of IFN-effects as measured in the RG assay, and increased stability at pH3.5 and 4.5.

In one embodiment, the invention provides a hzACO-1 variant that specifically binds human IFN-α, and comprises VH CDR sequences substantially identical to the sequences of Kabat residues 31-35, 50-65, and 95-102 of SEQ ID NO:3, further comprising a mutation in one of the VH CDR sequences, wherein the mutation is not in Kabat residue 58. The antibody may, e.g., comprise VH CDRs consisting of Kabat residues 31-35, 50-65, and 95-102 of SEQ ID NO:3, further comprising a mutation in one of the VH CDR sequences, wherein Kabat residue 58 is I. In one embodiment, the humanized ACO-1 comprises VH framework residues derived from a human VH1_46 gene and a human JH4 gene. As shown in the Examples, an I58S mutation in hzACO-1 substantially decreased the binding affinity to IFN-αA and decreased the potency for inhibition of IFN-effects as measured in the RG assay.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Fc Modifications

In addition or as an alternative to modifications made within the framework or CDR regions, antibodies of the invention may be engineered to include modifications within the Fc region, typically to alter one or more functional properties of the antibody, such as serum half-life, complement fixation, Fc receptor binding, protein stability and/or antigen-dependent cellular cytotoxicity, or lack thereof. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The residues in the Fc region are numbered according to Kabat.

If desired, the class of an antibody may be "switched" by known techniques. Such techniques include, e.g., the use of direct recombinant techniques (see e.g., U.S. Pat. No. 4,816,397) and cell-cell fusion techniques (see e.g., U.S. Pat. No. 5,916,771). For example, an antibody that was originally produced as an IgM molecule may be class switched to an IgG antibody. Class switching techniques also may be used to convert one IgG subclass to another, e.g., from IgG1 to IgG2. Thus, the effector function of the antibodies of the invention may be changed by isotype switching to, e.g., an IgG1, IgG2, IgG3, IgG4, IgD, IgA, IgE, or IgM antibody for various therapeutic uses. Exemplary cDNA sequences for constant regions are available via, e.g., GenBank, each of which incorporated by reference in its entirety, are as follows:

Human IgG1 constant heavy chain region: GenBank accession No.: J00228;

Human IgG2 constant heavy chain region: GenBank accession No.: J00230;

Human IgG3 constant heavy chain region: GenBank accession No.: X04646;

Human IgG4 constant heavy chain region: GenBank accession No.: K01316; and

Human kappa light chain constant region: GenBank accession No.: J00241.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al. In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In yet other embodiments, the Fc region is altered by replacing at least one amino acid residue with a different amino acid residue to alter the effecter function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both to Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 and 239 are altered to thereby alter the ability of the antibody to fix complement. This approach is described further in PCT Publication WO 94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcRIII. Additionally, the following combination mutants were shown to improve FcγRIII binding: T256A/S298A, S298A/E333A, S298A/K224A and S298A/E333A/K334A.

The constant region may further be modified to stabilize the antibody, e.g., to reduce the risk of a bivalent antibody separating into two monovalent VH-VL fragments. For example, in an IgG4 constant region, residue S241 may be mutated to a proline (P) residue to allow complete disulphide bridge formation at the hinge (see, e.g., Angal et al., Mol Immunol. 1993; 30:105-8).

Glycosylation Modifications

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence.

Antigen-Binding Fragments

The anti-IFN-α antibodies of the invention may be prepared as full-length antibodies or antigen-binding fragments thereof. Examples of antigen-binding fragments include Fab, Fab', F(ab)2, F(ab')2, F(ab)3, Fv (typically the VL and VH domains of a single arm of an antibody), single-chain Fv (scFv; see e.g., Bird et al., Science 1988; 242:423-426; and Huston et al. PNAS 1988; 85:5879-5883), dsFv, Fd (typically the VH and CH1 domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al., Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23:1126-1136; WO2005040219, and published U.S. Patent Applications 20050238646 and 20020161201.

Antibody fragments can be obtained using conventional recombinant or protein engineering techniques, and the fragments can be screened for antigen-binding or other function in the same manner as are intact antibodies.

Various techniques have been developed for the production of antibody fragments. Traditionally, these fragments were derived via proteolytic digestion of full-length antibodies (see, e.g., Morimoto et al., Journal of Biochemical and Biophysical Methods, 24:107-117 (1992); and Brennan et al., Science, 229:81 (1985)). However, these fragments can now be produced directly by recombinant host cells. Alternatively, Fab'-SH fragments can be directly recovered from E. coli and chemically coupled to form F(ab')2 fragments (Carter et al., Bio/Technology, 10:163-167 (1992)). According to another approach, F(ab')2 fragments can be isolated directly from recombinant host cell culture. In other embodiments, the antibody of choice is a single-chain Fv fragment (scFv). See WO 1993/16185; U.S. Pat. No. 5,571,894; and U.S. Pat. No. 5,587,458. The antibody fragment may also be a "linear antibody", e.g., as described in U.S. Pat. No. 5,641,870, for example. Such linear antibody fragments may be monospecific or bispecific.

Multispecific Molecules

In another aspect, the present invention features multispecific molecules comprising an anti-IFN-α antibody, or an antigen-fragment thereof, of the invention. Such multispecific molecules include bispecific molecules comprising at least one first binding specificity for IFN-α and a second binding specificity for a second target epitope.

One type of bispecific molecules are bispecific antibodies. Bispecific antibodies are antibodies that have binding specificities for at least two different epitopes. Methods for making bispecific antibodies are known in the art, and traditional production of full-length bispecific anti-bodies is usually based on the coexpression of two immunoglobulin heavy-chain-light-chain pairs, where the two chains have different specificities (Millstein et al., Nature, 305: 537-539 (1983)). Bispecific antibodies can be prepared as full-length antibodies or antibody fragments (e.g. F(ab')2 bispecific antibodies) or any other antigen-binding fragments described herein.

Other multispecific molecules include those produced from the fusion of a IFN-α-binding antibody moiety to one or more other non-antibody proteins. Such multispecific proteins and how to construct them have been described in the art. See, e.g., Dreier et al. (Bioconjug. Chem. 9(4): 482-489 (1998)); U.S. Pat. No. 6,046,310; U.S. Patent Publication No. 20030103984; European Patent Application 1 413 316; US Patent Publication No. 20040038339; von Strandmann et al., Blood (2006; 107:1955-1962), and WO 2004056873.

Multispecific molecules with more than two valencies are also contemplated. For example, trispecific antibodies can be prepared. Tutt et al., J. Immunol, 147: 60 (1991).

The multispecific molecules of the present invention can be prepared by conjugating the constituent binding specificities using methods known in the art. For example, each binding specificity of the multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) J. Exp. Med. 160: 1686; Liu, M A et al., (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described or reviewed in, for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; U.S. Pat. No. 5,482,858; U.S. Patent application publication 20030078385, Kontermann et al., (2005) Acta Pharmacological Sinica 26(1):1-9; Kostelny et al., (1992) J. Immunol. 148(5):1547-1553; Hollinger et al., (1993) PNAS (USA) 90:6444-6448; and Gruber et al. (1994) J. Immunol. 152: 5368.

Antibody Derivatives

Antibody derivatives (or immunoconjugates) within the scope of this invention include anti-IFN-α antibodies conjugated or covalently bound to a second agent.

For example, in one aspect, the invention provides immunoconjugates comprising an antibody conjugated or covalently bonded to a cytotoxic agent, which cytotoxic agent can be selected from therapeutic radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, camptothecans, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, abrin, 5-fluorouridine, ribonuclease (RNase), DNase I, Staphylococcal enterotoxin-A, pokeweed antiviral protein, gelonin, diphtherin toxin, *Pseudomonas* exotoxin, and *Pseudomonas* endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

In another embodiment, the antibody is derivatized with a radioactive isotope, such as a therapeutic radionuclide or a radionuclide suitable for detection purposes. Any of a number of suitable radioactive isotopes can be used, including, but not limited to, I-131, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

The antibody conjugates of the invention can be used to modify a given biological response, where the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The second agent can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56: 244; Wong, Chemistry of Protein Conjugation and Cross-linking (CRC Press 1991); Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chemistry 8:3; Reisfeld et al. (1989) Antihody, Immunicon. Radiopharm. 2:217; the entire disclosures of each of which are herein incorporated by reference). See, also, e.g. Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985), and Thorpe et al., "The Preparation And Cytotoxic Properties Of Antibody-Toxin Conjugates", Immunol. Rev., 62:119-58 (1982).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

In other embodiments, the second agent is a detectable moiety, which can be any molecule that can be quantitatively or qualitatively observed or measured. Examples of detectable markers useful in the conjugated antibodies of this invention are radioisotopes, fluorescent dyes, or a member of a complementary binding pair, such as a member of any one of: and antigen/antibody (other than an antibody to IFN-α), lectin/carbohydrate; avidin/biotin; receptor/ligand; or molecularly imprinted polymer/print molecule systems.

The second agent may also or alternatively be a polymer, intended to, e.g., increase the circulating half-life of the antibody. Exemplary polymers and methods to attach such polymers to peptides are illustrated in, e.g., U.S. Pat. Nos. 4,766,106; 4,179,337; 4,495,285; and 4,609,546. Additional illustrative polymers include polyoxyethylated polyols and polyethylene glycol (PEG) moieties. As used herein, the term "polyethylene glycol" is intended to encompass any of the forms of PEG that have been used to derivative other proteins, such as mono (C1-C10) alkoxy- or aryloxy-polyethylene glycol or polyethylene glycol-maleimide. For example, a full-length antibody or antibody fragment can be conjugated to one or more PEG molecules with a molecular weight of between about 1,000 and about 40,000, such as between about 2000 and about 20,000, e.g., about 3,000-12,000. To pegylate an antibody or fragment thereof, the antibody or fragment typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Antibody Characterization

After production or purification, or as part of a screening or selection procedure, the functional characteristics of an anti-IFN-α antibody of the invention can be investigated.

The following are brief descriptions of exemplary assays for antibody characterization. Some are further described in other sections and/or described in the Examples.

Binding Assays

The present invention provides for antibodies, and antigen-binding fragments and immunoconjugates thereof, that bind IFN-α. Any of a wide variety of assays can be used to assess binding of an antibody to IFN-α. Protocols based upon ELISAs, radioimmunoassays, Western blotting, BIACORE, and competition assays, inter alia, are suitable for use and are well known in the art.

For example, simple binding assays can be used, in which a test antibody is incubated in the presence of a target protein or epitope (e.g., an IFN-α protein subtype selected from A, 2, B2, C, F, G, H2, I, J1, K, 4a, 4b, WA, 1 and D, a portion thereof, or a combination of any thereof), unbound antibodies are washed off, and the presence of bound antibodies is assessed using, e.g., RIA, ELISA, etc. Such methods are well known to those of skill in the art. Any amount of binding above the amount seen with a control, non-specific antibody indicates that the antibody binds specifically to the target.

In such assays, the ability of the test antibody to bind to human IFN-α can be compared with the ability of a (negative) control protein, e.g. an antibody raised against a structurally unrelated antigen, or a non-Ig peptide or protein, to bind to the same target. Antibodies or fragments that bind to IFN-α using any suitable assay with 25%, 50%, 100%, 200%, 1000%, or higher increased affinity capacity ? relative to the control protein, are said to "specifically bind to" or "specifically interact with" the target, and are preferred for use in the therapeutic methods described below. The ability of a test antibody to affect the binding of a (positive) control antibody against IFN-α, e.g. a humanized ACO-1 or ACO-2 antibody, may also be assessed.

In one aspect, the invention provides for humanized anti-IFN-α antibodies sharing biological characteristics and/or substantial VH and/or VL sequence identity with humanized ACO-1 or ACO-2 antibodies. One exemplary biological characteristic is the binding to the ACO-1 or ACO-2 epitope, i.e., the respective regions in the extracellular domain of certain IFN-α protein subtypes to which the ACO-1 and ACO-2 antibodies bind. To screen for antibodies that bind to the ACO-1 or ACO-2 epitope, a routine cross-blocking assay, such as that described in Antibodies, A Laboratory Manual, Cold Spring Harbor Laboratory, Ed Harlow and David Lane (1988), can be performed.

In an exemplary cross-blocking or competition assay, ACO-1 or ACO-2 (control) antibody and a test antibody are admixed (or pre-adsorbed) and applied to a sample containing IFN-α. In certain embodiments, one would pre-mix the control antibodies with varying amounts of the test antibody (e.g., 1:10 or 1:100) for a period of time prior to applying to the IFN-α-containing sample. In other embodiments, the control and varying amounts of test antibody can simply be admixed during exposure to the antigen/target sample. As long as one can distinguish bound from free antibodies (e.g., by using separation or washing techniques to eliminate unbound antibodies) and the control antibody from test antibody (e.g., by using species- or isotype-specific secondary antibodies, by specifically labeling the control antibody with a detectable label, or by using physical methods such as mass spectrometry to distinguish between different compounds) one will be able to determine if the test antibody reduces the binding of the control antibody to the antigen, indicating that the test antibody recognizes substantially the same epitope as the control. In this assay, the binding of the (labeled) control antibody in the presence of a completely irrelevant antibody is the control high value. The control low value is be obtained by incubating the labeled (positive) control antibody with unlabeled control antibody, where competition would occur and reduce binding of the labeled antibody.

In a test assay, a significant reduction in labeled antibody reactivity in the presence of a test antibody is indicative of a test antibody that recognizes the same epitope, i.e., one that "cross-reacts" with the labeled control antibody. Any test antibody or compound that reduces the binding of the labeled control to the antigen/target by at least 50% or more preferably 70%, at any ratio of control:test antibody or compound between about 1:10 and about 1:100 is considered to be an antibody or compound that binds to substantially the same epitope or determinant as the control. Preferably, such test antibody or compound will reduce the binding of the control to the antigen/target by at least 90%. Nevertheless, any compound or antibody that reduces the binding of a control antibody or compound to any measurable extent can be used in the present invention.

Biological Activity

Differentiation of Monocytes. The generation of activated T and B lymphocytes requires the recruitment and maturation of antigen presenting cells ("APCs"). These APCs include B cells, monocytes/macrophages and dendritic cells. The serum of SLE patients contains IFN-α which can activate DCs and the activated activity can blocked with humanized antibody preparations according to the invention. Methods to detect and quantitate this activity are described in the scientific and patent literature (see, e.g., paragraphs 0136 through 0150 of patent publication number US20040067232A1, relevant portions of which are hereby incorporated herein by reference).

Activation of the MxA promoter. The ability of IFN-α to activate the MxA promoter, and the ability of the anti-IFN-α monoclonal antibodies of the invention to block this activation can be measured using reporter gene (RG) assays where the MxA promoter is fused to a reporter gene, such as chioramphenicol acetyltransferase (CAT) or luciferase (luc), preferably luciferase. Assays for CAT and luciferase are known to those of skill in the art. Preferably, the activity of the MxA promoter is measured in A549 cells stably transformed with an MxA promoter/reporter gene fusion construct. A549 cells are a lung carcinoma cell line available through the ATCC (product number CC1-185). The MxA (a.k.a. MxI) promoter can be human, mouse or rat. The sequence and structure of the human MxA promoter is disclosed in Genbank Accession number X55639, Chang et al. (1991) Arch Virol. 117:1-15; and Ronni et al. (1998) J Interferon Cytokine Res. 18:773-781. Human MxA promoter/luciferase fusion constructs and luciferase assays are disclosed in patent publication US20040209800 and Rosmorduc et al. (1999) J of Gen Virol 80:1253-1262. Human MxA promoter/CAT fusion constructs and CAT assays are disclosed in Fernandez et al. (2003) J Gen Virol 84:2073-2082 and Fray et al. (2001) J Immunol Methods 249:235-244. The mouse MxA (MxI) promoter is disclosed in Genbank accession number M21104; Hug et al. (1988) Mol Cell Biol 8:3065-3079; and Lleonart et al. (1990) Biotechnology 8:1263-1267. A mouse MxA promoter/luciferase fusion construct and a luciferase assay are disclosed in Canosi et al. (1996) J Immunol Methods 199:69-67.

Cytopathic effect inhibition (CPE) assays. CPE assays are based on the antiviral activity of interferon. In general, a suitable cell line is infected with a virus in the presence of interferon, and the inhibitory activity of interferon is quantified on viral propagation or replicative processes. The readout of the assay may be based on reduction of virus yield, reduction of viral cytopathic effect, reduction of viral protein or RNA synthesis, reduction of viral plaque formation. The cytopathic assay may be used to determine the neutralizing effect of antibodies on the activity of interferon. Exemplary CPE assays are described in Meager, A. 1987. Quantification of interferons by anti-viral assays and their standardization. In: Clemens, M. J., Morris, A. G., Gearing, A. J. H. (Eds), Lymphokines and interferons: A Practical Approach. IRL, Press, Oxford, p. 129 and Grossberg and Sedmak, 1984. Assays of interferons In: Billiau, A. (Ed) Interferon, vol. 1: General and Applied Aspects. Elsevier, Amsterdam, p. 189, and in Example 6, paragraphs 157-164, and FIG. 1 of PCT publication WO2006086586.

Pharmaceutical Formulations

Another object of the present invention is to provide a pharmaceutical formulation comprising a [the protein] compound which is present in a concentration from 10-500 mg/ml, such as e.g. 20-300 mg/ml, preferably 30-100 mg/ml, and most preferably 50-100 mg/ml, and wherein said formulation has a pH from 2.0 to 10.0. The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

Diagnostic Applications

The IFN-α-antibodies of the invention also have non-therapeutic applications. For example, anti-IFN-α antibodies may also be useful in diagnostic assays for IFN-α protein, e.g. detecting its expression in specific cells, tissues, or serum. For example, anti-IFN-α antibodies could be used in assays selecting patients for anti-IFN-α treatment. For such purposes, the anti-IFN-α antibodies could be used for analyzing for the presence of IFN-α in serum or tissue specimens. For diagnostic applications, the antibody typically will be labeled with a detectable moiety.

Therapeutic Applications

Methods of treating a patient using a humanized anti-IFN-α antibody as described herein are also provided for by the present invention. In one embodiment, the invention provides for the use of a humanized antibody as described herein in the preparation of a pharmaceutical composition for administration to a human patient. Typically, the patient suffers from, or is at risk for, an autoimmune or inflammatory disease or disorder associated with abnormal expression of at least one IFN-α subtype selected from the group consisting of subtypes A, 2, B2, C, F, G, H2, I, J1, K, 4a, 4b, and WA.

Exemplary conditions or disorders to be treated with the antibodies of the invention, include, but are not limited to lupus (e.g., systemic lupus erythematosis (SLE)), rheumatoid arthritis, juvenile chronic arthritis, osteoarthritis, spondyloarthropathies, systemic sclerosis (scleroderma), idiopathic inflammatory myopathies (dermatomyositis, polymyositis), Sjogren's syndrome, vasculitis, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis, Crohn's disease), celiac disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, and transplantation associated diseases including graft rejection and graft-versushost-disease. In a specific embodiment, the disease, condition or disorder is selected from lupus, Sjogren's syndrome, psoriasis, diabetes mellitus, rheumatoid arthritis, and juvenile dermatomyotosis. In another specific embodiment, the disease, condition, or disorder is SLE. For example, in one aspect, the anti-IFN-α antibody is used in combination with one or more other anti-inflammatory agents, including, but not limited to, analgesic agents, immunosuppressive agents, corticosteroids, and anti-TNFα agents or other anti-cytokine or anti-cytokine receptor agents, and anti-angiogenic agents. Specific examples include metothrexate, TSG-6, Rituxan®, and CTLA4-Fc fusion proteins. Further examples of combination therapies are provided below.

Articles of Manufacture

In another embodiment of the invention, an article of manufacture containing materials useful for the treatment of the disorders described above is provided. For example, the article of manufacture can comprise a container containing a humanized anti-IFN-α antibody as described herein together with instructions directing a user to treat a disorder such as an autoimmune or inflammatory disease or disorder in a human with the antibody in an effective amount. The article of manufacture typically comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example, the container may be an intravenous solution bag or a vial having a stopper pierceable by a hypodermic injection needle). At least one active agent in the composition is the humanized anti-IFN-α antibody herein, or an antigen-binding fragment or antibody derivative (e.g., an immunoconjugate) comprising such an antibody. The label or package insert indicates that the composition is used for treating the condition of choice, such as, e.g., SLE.

Moreover, the article of manufacture may comprise (a) a first container with a composition contained therein, wherein the composition comprises the human or humanized antibody herein, and (b) a second container with a composition contained therein, wherein the composition comprises a therapeutic agent other than the human or humanized antibody. The article of manufacture in this embodiment of the invention may further comprise a package insert indicating that the first and second compositions can be used in combination to treat an autoimmune or inflammatory disease or disorder. Such therapeutic agents may be any of the adjunct therapies described in the preceding section. Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In a first aspect, the present invention thus relates to a humanized antibody, or an antigen-binding fragment thereof, that specifically binds human interferon-α (IFN-α), which humanized antibody is a humanized version of murine antibody ACO-1 or ACO-2, or of a combination thereof, comprising fewer donor amino acid residues than the murine complementary determining regions (CDRs) according to Kabat.

In a second aspect, the present invention thus relates to a humanized antibody that specifically binds IFN-α, or an antigen-binding fragment thereof, wherein said antibody is capable of binding IFN-α subtypes A, 2, B2, C, F, G, H2, I, J1, K, 4a, 4b and WA, but not subtypes 1 or D, and wherein said antibody comprises fewer donor amino acid residues than the non-human CDRs according to Kabat.

According to one embodiment, the CDR H2 donor residues comprise Kabat residues 50-59. In another embodiment, said antibody competes with and/or binds to the same epitope on an IFN-α subtype as ACO-1 and/or ACO-2 antibody.

According to a preferred embodiment, the antibody is an IgG4 subtype. In a preferred embodiment, the antibody comprises a CDR H2 sequence according to SEQ ID NO: 21.

In a third aspect, the present invention relates to a method for producing an antibody according to the invention, wherein said method comprises incubating a host cell encoding said antibody under appropriate conditions and subsequently isolating said antibody. The invention furthermore relates to antibodies obtained by or obtainable by such methods.

In a third aspect, the present invention relates to a composition comprising an antibody according to the invention. The invention furthermore relates to a process for the preparation of a composition according to the invention, wherein said method comprises mixing antibody or a fragment thereof with excipients. The invention furthermore relates to compositions obtained by or obtainable by such methods.

In a fifth aspect, the present invention relates to a method of preventing, managing, treating or ameliorating an IFN-α related IFNlammatory disease or disorder, said method comprising administering to a subject in need thereof a prophylactically or therapeutically effective amount of an antibody according to the invention.

Finally, the present invention relates to use of an antibody according to the invention for preparation of a medicament suitable for treatment of an inflammatory disease.

EXAMPLES

Further details of the invention are illustrated by the following non-limiting Examples.

Example 1

Sequencing of Murine ACO-1 and ACO-2 Antibodies

This example describes sequencing and recombinant expression of the murine anti-bodies ACO-1 and ACO-2, described in WO20060086586, as well as BLAST searches on the ACO-2 VH and VL sequences.

Antibody Cloning and Sequencing

Total RNA was extracted from hybridomas (ACO-1.5.2 and ACO-2.2.1) using the RNeasy® kit (#634914) from Qiagen®. cDNA was synthesized from 1 µg total RNA using SMART™-RACE cDNA amplification kit from Clontech®. The reaction was run at 42° C. for 1.5 h and the samples were diluted in 75 µl tricine-EDTA. PCR amplification of the target was carried out in 50 µl reactions using 5 µl of cDNA as template. The forward primer for both heavy and light chain was universal primer mix (UPM) that was included in the SMART™ RACE kit. The reverse primer sequence for ACO-1 heavy chain (HC) was designed as follows:

```
5'-CTGGGCCAGGTGCTGGAGG          (SEQ ID NO: 11)
and, for

ACO-1 light chain (LC)
5'-CTAACACTCATTCCTGTTGAAGCTC.   (SEQ ID NO: 12)
```

The reverse primer sequence for ACO-2 heavy chain (HC) was designed as follows:

```
                                          (SEQ ID NO: 26)
5'-CTAGCTAGCTCATTTACCCGGAGACCGGGAGATGG
and, for ACO-2 light chain (LC):
                                          (SEQ ID NO: 27)
5'-GCTCTAACACTCATTCCTGTTGAAGCTCTTG.
```

The PCR reactions were carried out using Advantage® HF PCR kit from Clontech® and the PCR program was run with a single denaturing step at 94° C./2 min followed by 24 cycles as given: 94° C./30 sec.; 55° C./30 sec.; 72° C./1.5 min. The final extension step was 72° C./10 min. The PCR products were identified on a 1% agarose gel containing ethidiumbromide. The PCR products were purified from the gel using GFX™ Purification kit from GE Healthcare followed by cloning into Zero Blunt® TOPO® PCR Cloning Kit (#K2875-40) and transformed into TOP10 *E. coli* cells from Invitrogen®.

DNA was extracted from *E. coli* colonies using the miniprep kit (#27106) from Qiagen®. Plasmids were sequenced at MWG Biotech™, Matinsried, Germany using the sequencing primers M13 rev (−29) and M13 uni (−21). HC and LC were verified from the identified sequences by using Vector NTI®. All procedures based on kits were performed according to manufacturer directions.

From the ACO-1.5.2 hybridoma cells a single kappa LC and a single IGg2a HC were cloned, having the following nucleic acid and amino acid sequences.

```
ACO-1 VH sequence
(SEQ ID NO: 13 (signal peptide included)):
atgggatggagctatatcatgctcttttggtagcaacagctacagatg tccactcccaggtccaactgcagcagcctggggctgaactggtgaagcc tggggcttcagtgaagctgtcctgtaaggcttctggctacaccttcacc aactactggatgcactgggtgaagcagaggcctggacaaggccttgagt ggattggagagattaatcctagccacggtcgtactatctacaatgaaaa cttcaagagcaaggccacactgactgtagacaaatcctccatcacagcc ttcatgcaactcagcagcctgacatctgaggactctgcggtctatttct gtgcaagaggggactgggacccgcctggtttgcttactggggccaagg gactctggtcactgtctctgca ACO-1 VL sequence
(SEQ ID NO: 14 (signal peptide included)):
atggattttcaagtgcagattttcagcttcctgctaatcagtgtctcag tcataatgtccagaggacaaattgttctcacccagtctccagcaatcat gtctgcttctcctggggagaaggtcaccttgacctgcagtgccggctca agtgtagattccagctatttgtactggtaccagcagaagccaggatcct cccccaaactctggatttatagcacatccaacctggcttctggagtccc tgctcgcttcagtggcagtgggtctgggacctcttactctctcacaatc agcagcatggaggctgaagatgctgcctcttatttctgccatcagtgga gtagttacccattcacgttcggctcggggacaaaattggaaataaaacgg ACO-1 VH (SEQ ID NO: 1 (signal peptide excluded))
QVQLQQPGAELVKPGASVKLSCKASGYTFTNYWMHWVKQRPGQGLEWIG

EINPSHGRTIYNENFKSKATLTVDKSSITAFMQLSSLTSEDSAVYFCAR

GGLGPAWFAYWGQGTLVTVSA
```

```
ACO-1 VL (SEQ ID NO: 4 (signal peptide excluded))
QIVLTQSPAIMSASPGEKVTLTCSAGSSVDSSYLYWYQQKPGSSPKLWI

YSTSNLASGVPARFSGSGSGTSYSLTISSMEAEDAASYFCHQWSSYPFT

FGSGTKLEIKR
```

From the ACO-2.2.1 hybridoma cells a single kappa type ACO-2 light chain and a single IGg2b ACO-2 heavy chain were cloned, with the following nucleic acid and amino acid sequences.

```
ACO-2 VH sequence
(SEQ ID 28 (signal peptide included))
atgggatggagctatatcatcctcttttggtagcagcagctacagatg tccactcccaggtccaactgcagcagcctggggctgaactggtgaagcc tggggcttcagtgaagctgtcctgcaaggcctctggctacagcttcacc agctactggatgcactgggtgaagcagaggcctggacaaggccttgagt ggattggagagattaatcctagccacggtcgtactagctacaatgagaa cttcaagagcaaggccacactgactgtagacaaatcctccaacatagtc tacatgcaactcagcagcctgacatctgaggactctgcggtctattact gtgtaagaggggactgggacccgcctggtttgcttactggggccaagg gactctggtcactgtctctgta ACO-2 VL sequence
(SEQ ID NO: 29 (signal peptide included))
atggattttcaagtgcagattttcagcttcctgctaatcagtgtctcag tcataatgtccagaggacaaattgttctcacccagtctccagcaatcat gtctgcatctcctggggagaaggtcaccttgacctgcagtgccggctca agtgtaggttccagctacttttactggtaccagcagaagccaggatcct cccccaaactctggatttatggcacatccaacctggcttctggagtccc tgctcgcttcagtggcagtgggtctgggacctcttactctctcacaatc agcagcatggaggctgaagatgctgcctcttatttctgccatcagtgga gtagttatccattcacgttcggctcggggacaaaattggaaataaaacgg ACO-2 VH sequence
(SEQ ID NO: 7 (signal peptide excluded)):
QVQLQQPGAELVKPGASVKLSCKASGYSFTSYWMHWVKQRPGQGLEWIG

EINPSHGRTSYNENFKSKATLTVDKSSNIVYMQLSSLTSEDSAVYYCVR

GGLGPAWFAYWGQGTLVTVSV

ACO-2 VL sequence
(SEQ ID NO: 9 (signal peptide excluded)):
QIVLTQSPAIMSASPGEKVTLTCSAGSSVGSSYFYWYQQKPGSSPKLWI

YGTSNLASGVPARFSGSGSGTSYSLTISSMEAEDAASYFCHQWSSYPFT

FGSGTKLEIKR
```

The ACO-2 CDR sequences according to the Kabat definitions were found to be as follows.

| | | |
|---|---|---|
| CDR-H1: | SYWMH | (SEQ ID NO: 22) |
| CDR-H2: | EINPSHGRTSYNENFKS | (SEQ ID NO: 23) |
| CDR-H3: | GGLGPAWFAY | (SEQ ID NO: 17) |
| CDR-L1: | SAGSSVGSSYFY | (SEQ ID NO: 24) |
| CDR-L2: | GTSNLAS | (SEQ ID NO: 25) |
| CDR-L3: | HQWSSYPFT | (SEQ ID NO: 20) |

Example 2

Design of Humanized ACO-1 and Identification of Potential Back-Mutation Residues Identification and Characterization of Mouse ACO-1 CDRs The ACO-1 CDR sequences according to the Kabat definitions were found to be as follows.

| | | |
|---|---|---|
| CDR-H1: | NYWMH | (SEQ ID NO: 15) |
| CDR-H2: | EINPSHGRTIYNENFKS | (SEQ ID NO: 16) |
| CDR-H3: | GGLGPAWFAY | (SEQ ID NO: 17) |
| CDR-L1: | SAGSSVDSSYLY | (SEQ ID NO: 18) |
| CDR-L2: | STSNLAS | (SEQ ID NO: 19) |
| CDR-L3: | HQWSSYPFT | (SEQ ID NO: 20) |

Identification of Human Germline

A 3D protein structure model was built using MOE (Molecular Operating Environment; available at www.chemcomp.com) with a structural template from the Protein Database Bank (PDB): 1Z3G. The PDB is described in Berman et al. (Nucl Acids Res 2000; 28:235-242), and is available at www.rcsb.org/pdb. Based on an analysis of antibody-antigen complexes in the PDB database, the most probable residues in the paratope were found to be residues 23-35, 49-58, 93-102 of the ACO-1 VH, and 24-34, 49-56, 89-97 of the ACO-1 VL. Using MOE, residues interacting (hydrophobic, hydrogen binding, charge interaction) with the paratope were identified and the combined set of residues (paratope+interacting residues) were taken as the so-called mask of ACO-1 shown in FIG. 1.

Searching the germline V databases with the ACO-1 VH and ACO-1 VL returned the following potential framework templates (E-value given in parenthesis):

VH: VH1_46 (3e-038) VH1_f (6e-037), VH1_02 (6e-037), VH1_03 (1e-036), VH1_24 (2e-034),

VL: VKIII_L6 (9e-035), VKIII_A11 (4e-034), VKIII_A27 (8e-034), VKIII_L25 (1e-033), VKI_L8 (1e-033).

Searching the germline databases with the mask returned the following potential framework templates (E-value given in parenthesis):

VH: VH1_46 (3e-011) VH1_02 (6e-011), VH1_f (1e-010), VH5_a (4e-010), VH1_03 (4e-010),

VL: VKIII_A11 (5e-009), VKIII_L6 (7e-009), VKIII_A27 (9e-009), VKIII_L25 (3e-008), VKI_L9 (6e-008).

After manual inspections of the alignments and the hits, VH1_46 and VKIII_L6 were selected as the human scaffolds. Other templates could be chosen to alter or optimize, e.g., the physical-chemical properties of the humanized antibody. JH4 and JK2 were selected as germline J-segments (SEQ ID NO:2 and 5, respectively).

Design of Optimal Humanized ACO-1

Humanization was performed with the following rules:

Residues outside the mask were taken as human.
Residues inside the mask and inside the Kabat CDR were taken as murine.
Residues inside the mask and outside the Kabat CDR with mouse/germline consensus were taken as the consensus sequence.
Residues inside the mask and outside the Kabat CDR with mouse/germline were taken as the germline sequence, but the murine difference were subject to potential back mutations.

The CDRs of the optimal hzACO-1 antibody obtained were (according to the Kabat definitions):

| | | |
|---|---|---|
| CDR_H1 | NYWMH | (SEQ ID NO: 15) |
| CDR_H2 | EINPSHGRTIYAQKFQG | (SEQ ID NO: 21) |
| CDR_H3 | GGLGPAWFAY | (SEQ ID NO: 17) |
| CDR_L1 | SAGSSVDSSYLY | (SEQ ID NO: 18) |
| CDR_L2 | STSNLAS | (SEQ ID NO: 19) |
| CDR_L3 | HQWSSYPFT | (SEQ ID NO: 20) |

Using the above humanization method, designing a mask of residues predicted to constitute the paratope based on a 3D model of hzACO-1 and IFN-αA, in contrast to simple CDR grafting, a hzACO-1 antibody with fewer murine residues was obtained, since the peptide comprising the 5 C-terminal amino acids of the optimized hzACO-1 CDR H2 sequence (highlighted in bold above) was identical to the corresponding human framework sequence, while the corresponding peptide in the ACO-1 CDR H2 sequence according to the Kabat definitions was of murine origin. Additionally, the CDR H1 sequence for a humanized ACO-1 antibody identified in the present analysis was shorter than the one described in WO2006/086586. The optimized hzACO-1 antibody, or an antibody or antigen-binding fragment comprising at least a portion of the hzACO-1 VH sequence, can thus provide for a reduced risk for a human-anti-mouse-antibody (HAMA)-response in a human patient.

In addition, the replacement of the sequence AQK instead of NEN in position 60-62 in heavy chain has the advantage of avoiding two asparagine residues which may be prone to deamidation.

Identification of Potential Backmutations.

The analysis of ACO-1 VH and VL sequences is illustrated in FIG. 1. In FIG. 1, the resulting humanized ACO-1 (hzACO-1) VH (SEQ ID NO:3) and VL (SEQ ID NO:6) sequences are shown with potential back-mutation residues as human, i.e., without any back-mutations. The following back-mutation variants in the framework regions were identified for obtaining one or more optimized hzACO-1 antibodies, which are often required in order to retain the affinity of the original mouse antibody:

hzACO-1 VH: wild-type (i.e., no back-mutation), V5Q, M69L, R71V, T73K, S76I, V78A and any combination any thereof;

hzACO-1 VL: wild-type, E1Q, L47W, I58V, F71Y and any combination of any thereof;

in various heavy-light chain combinations.

Example 3

Design of ACO-2-Based Variants of hzACO-1 for Affinity Maturation of hzACO-1

As shown in FIG. 2, amino acid sequence alignments of the ACO-1 and ACO-2 VH and VL sequences revealed a high sequence identity between the respective light and heavy chains. Without being limited to theory, it is possible that the antibodies derived from the same precursor cell as they had the same V-D-J rearrangement and contained 3 identical mutations compared to the germline sequence. In addition, the antibodies differed at 13 amino acid residues, possibly due to subsequent somatic hyper-mutations.

Out of the 13 non-identical amino acid residues in the ACO-1 and ACO-2 VH and VL domains, 9 residues were selected for mutational analysis in order to improve the affinity of the humanized ACO-1 antibody (FIG. 3). Single additions of ACO-2 derived hypermutations could potentially identify deleterious and beneficial amino acid residues and by allowing the introduction of only the beneficial amino acids improve the affinity beyond the original mouse ACO-1 and ACO-2 antibodies. The targeted residues were chosen based on their position within one of the light or heavy chain CDRs (according to the Kabat definition) or based on their location within regions outlined as potential antigen-interacting regions based on antigen-antibody 3D-modelling.

The following variants were identified for obtaining one or more optimized hzACO-1 antibodies:

hzACO-1 VH: wild-type, T28S, N31S, I58S, S76N, T77I and A93V, and any combination of at least two mutations selected from T28S, N31S, I58S, S76N, T77I and A93V;

hzACO-1 VL: wild-type, D29G, L33F, S50G and any combination of at least two mutations selected from D29G, L33F, and S50G, in various heavy-light chain combinations.

Residues were mutated separately from ACO-1 sequence to ACO-2 sequence within the hzACO-1 light and heavy chain constructs, in order to evaluate the individual contribution of each residue to antigen binding. A series of combination mutants was also generated.

Example 4

Cloning of ACO-1, ACO-2, hzACO-1 and Site-Directed Mutagenesis

ACO-1, ACO-2, and hzACO-1

The VH and VL sequences were transferred to CMV promoter-based expression vectors (pTT vectors) suitable for transient expression in the HEK293-EBNA (HEK293-6E) expression system described by Durocher et al. (Nucleic Acids Res. 2002; 30(2):E9). In addition to the CMV-promoter, the vectors contain a pMB1 origin, an EBV origin and the AmpR gene. The VH of ACO-1 and ACO-2 were cloned into the CMV-based vector containing the constant region for mouse IgG2a and IgG2b, respectively. The full length LC was transferred to the empty CMV-based vector for both ACO-1 and ACO-2. The DNA sequences for the variable regions of hzACO-1 were ordered from Geneart, Regensburg, Germany. The delivered sequence for the hzACO-1 VH was transferred to the expression vector containing the constant region for human IgG4(S241P) (containing a S241P mutation in the hinge region). The delivered hzACO-1 VL sequence was transferred to the vector containing the constant region for a human kappa light chain.

Generation of Back-Mutation Variants of hzACO-1

The 10 potential back-mutations identified in Example 2 were introduced separately to hzACO-1 HC and LC constructs in order to gauge the individual contribution of each residue to antigen binding. A few combinations were included as well. A variant of hzACO-1 with an extended CDR H2 (hzACO-1-Kabat CDRH2), equivalent to the Kabat definition of the murine CDR H2 (SEQ ID NO:16) was also generated by site-directed mutagenesis.

Site-directed mutagenesis was performed on the hzACO-1 LC and HC expression vectors. To generate single mutants the QuickChange® Site-Directed Mutagenesis kit from Stratagene (cat.#200518) was used according to the manufactures protocol. Introduction of desired mutations was verified by sequencing plasmid DNA preparations (MWG Biotech, Matinsried, Germany) for each mutant.

The mutated LC constructs were combined with the hzACO-1 HC for expression, and mutated HC constructs were combined with the hzACO-1 LC for antibody expression.

Light Chain Variants with Back-Mutations:

hzACO-1-E1Q
hzACO-1-L47W
hzACO-1-I58V
hzACO-1-F71Y
hzACO-1-L47W,I58V

Heavy Chain Variants with Back-Mutations:

hzACO-1-V5Q
hzACO-1-M69L
hzACO-1-R71V
hzACO-1-T73K
hzACO-1-S76I
hzACO-1-V78A
hzACO-1-R71V,T73K
hzACO-1-M69L, R71V, T73K, S76I, V78A
hzACO-1-Kabat CDRH2

Generation of ACO-2-Based Variants of hzACO-1

Site-directed mutagenesis introducing ACO-2 specific residues into the hzACO-1 antibody in order to improve affinity, as described in example 3, was performed on the hzACO-1 LC and HC expression vectors. To generate single mutants the QuickChange® Site-Directed Mutagenesis kit from Stratagene (cat.#200518) was used according to the manufactures protocol. Combination mutants were generated using both the QuickChange® Site-Directed Mutagenesis and QuickChange® Multi Site-Directed Mutagenesis kits according to the manufactures protocols (cat.#200513).

Introduction of desired mutations was verified by sequencing plasmid DNA preparations (MWG Biotech, Matinsried, Germany) for each mutant.

The mutated light chain constructs were combined with the hzACO-1 heavy chain for expression and mutated heavy chain constructs were combined with the hzACO-1 light chain constructs for antibody expression.

Light Chain Variants with ACO-2-Derived Mutations:

hzACO-1-D29G
hzACO-1-L33F
hzACO-1-S50G
hzACO-1-D29G,L33F,S50G

Heavy Chain Variants with ACO-2-Derived Mutations:

hzACO-1-T28S
hzACO-1-N31S
hzACO-1-I58S
hzACO-1-S76N
hzACO-1-T77I
hzACO-1-A93V
hzACO-1-N31S,I58S
hzACO-1-T28S,N31S,I58S,A93V
hzACO-1-S76N,T77I
hzACO-1-T28S,N31S,I58S,S76N,T77I,A93V
hzACO-1-T28S,A93V
hzACO-1-N31S,A93V
hzACO-1-T28S,N31S,A93V
hzACO-1-T28S,N31S

Example 5

Expression of Recombinant ACO Derived Antibodies

The ACO-1, ACO-2, hzACO-1, and hzACO-1 variants were expressed in transiently transfected HEK293 cells following a generic antibody expression protocol. The following describes the transfection protocol for suspension adapted HEK293 cells.

Cell maintenance: Suspension adapted HEK293 cells were grown in GIBCO® Free-Style™ 293 Expression medium (Invitrogen cat. #: 12338-026) supplemented with 25 µg/ml Geneticin® (Invitrogen cat. #: 10131-019), 0.1% v/v Pluronic® F-68 (Invitrogen cat. #: 12347-019) surfactant & 1% v/v Penicillin-Streptomycin (Optional) (Invitrogen cat. #15140-122). Cells were maintained in Erlenmeyer shaker flasks at cell densities between $0.2$–$2\times10^6$ cells/ml in an incubator shaker at 37° C., 8% $CO_2$ and 125 rpm.

DNA Transfection: The cell density of cultures used for transfection was $0.8$–$1.5\times10^6$ cells/ml. 0.5 µg light chain vector DNA+0.5 µg heavy chain vector DNA were used per ml cell culture. 293Fectin™ (Invitrogen cat. #: 12347-019) was used as transfection reagent at a concentration of 1 µl reagent per µg transfected DNA. The 293Fectin™ was diluted in 30×vol. Opti-MEM® (Invitrogen cat. #: 51985-034), mixed and left at room temperature (23-25° C.) for 5 min. The DNA was diluted in 30 µl Opti-MEM® per µg total DNA, mixed and left at room temperature (23-25° C.) for 5 min. The DNA and transfection reagent dilutions were mixed 1:1 and left at room temperature (23-25° C.) for 25 min. The DNA-293Fectin™ mix was added directly to the cell culture. The transfection cell culture was transferred to an incubator shaker at 37° C., 8% $CO_2$ and 125 rpm. After 4-7 days, cell culture supernatants were harvested by centrifugation followed by filtration through a 0.22 µm PES filter (Corning cat. #: 431098). The antibodies were analyzed as supernatants or purified using standard protein A purification techniques.

Expression Level Comparison of hzACO-1 and hzACO-1-Kabat CDRH2

Transient expression levels in HEK293-6E cells were compared for hzACO-1 and hzACO-1-Kabat CDRH2 to determine if the distal CDR H2 residues had any effect on the ability of the cells to expressed either of the two antibody variants.

HEK293-6E cells were transfected as described above with pTT-based expression vectors for hzACO-1 light chain and hzACO-1 or hzACO-1-Kabat CDRH2 heavy chains. The transfections was performed in triplicates. For each antibody variant, three cultures (25 ml) were transfected using a DNA-293Fectin master mix to minimize the influence from pipetting inaccuracy. The transfected cultures were incubated in a shaker incubator for 4 days as described above. At day 4, samples were extracted from the cultures for cell viability and cell density measurements and the remaining cell culture supernatants were harvested by centrifugation. Quantitation analysis of antibody production was performed by Biolayer Interferometry directly on clarified cell culture supernatants using the ForteBio® Octet® system and protein A biosensors. Cell culture densities and viabilities were measured using a Cedex HiRes™ automated cell culture analyzer. Results are show in Table 4 below.

The results in Table 4. unexpectedly show a significant difference in the transient expression levels for hzACO-1 (humanized IFN-alpha antibody according to the present invention) compared with hzACO-1-Kabat CDRH2 (humanized IFN-alpha antibody humanized using traditional procedures and hence full length Kabat sequences). No difference in cell viability or density was observed for the cell cultures transfected with either of the two hzACO-1 variants. The expression level for the hzACO-1 was approximately 2-fold higher compared to the expression level for hzACO-1-Kabat CDRH2 antibody variant By grafting a shorter version of CDR H2 compared to the Kabat-defined CDRH2, expression levels of the antibody were surprisingly significantly increased.

Without being bound by theory, it may hypothesized that the human germline-derived residues in the hzACO-1 as compared to the hzACO-1-Kabat CDRH2 antibody variant, carrying the extended CDR H2 (SEQ ID:16) affect HC folding and potentially LC-HC interaction, results in an improved protein stability and thus expression yield.

Such an improved level of protein expression resulting from an improved protein stability observed in the transient expression levels will be reflected in stable CHO-based production cell lines. Therefore, by grafting the short version of CDRH2 (SEQ ID:21) generation of a high-producing stable production cell line is thus possible.

Expression Level Comparison of IgG4, 1 and 2 Variants of hzACO-1

Transient expression levels in HEK293-6E cells were compared for the lead IgG4(S241P) variant of hzACO-1 and hzACO-1 (IgG1) and hzACO-1 (IgG2) to determine if heavy chain subclass switching had any effect on antibody expression levels.

The experiment was performed similarly to the expression assay described above, but with the following changes: The experiment was performed in duplicates in 5 ml cultures. The cultures were incubated in filter capped 50 ml falcon tubes in a shaker incubator at 37° C., 8% $CO_2$ and 250 rpm.

Unpredictably, the average expression levels for hzACO-1 (IgG1) and hzACO-1 (IgG2) were approximately 65% of the expression level for hzACO-1 (IgG4). Based on the observed reduction in protein expression (~35%) we conclude that the combination of hzACO-1 variable domains and IgG4 constant domain is superior to combinations with other chain subclasses and the development of this molecule greatly facilitate generation of a high-producing stable production cell line.

Example 6

Crystal Structure of IFN-α8 in Complex with hzACO-1-Fab

Figure 8:
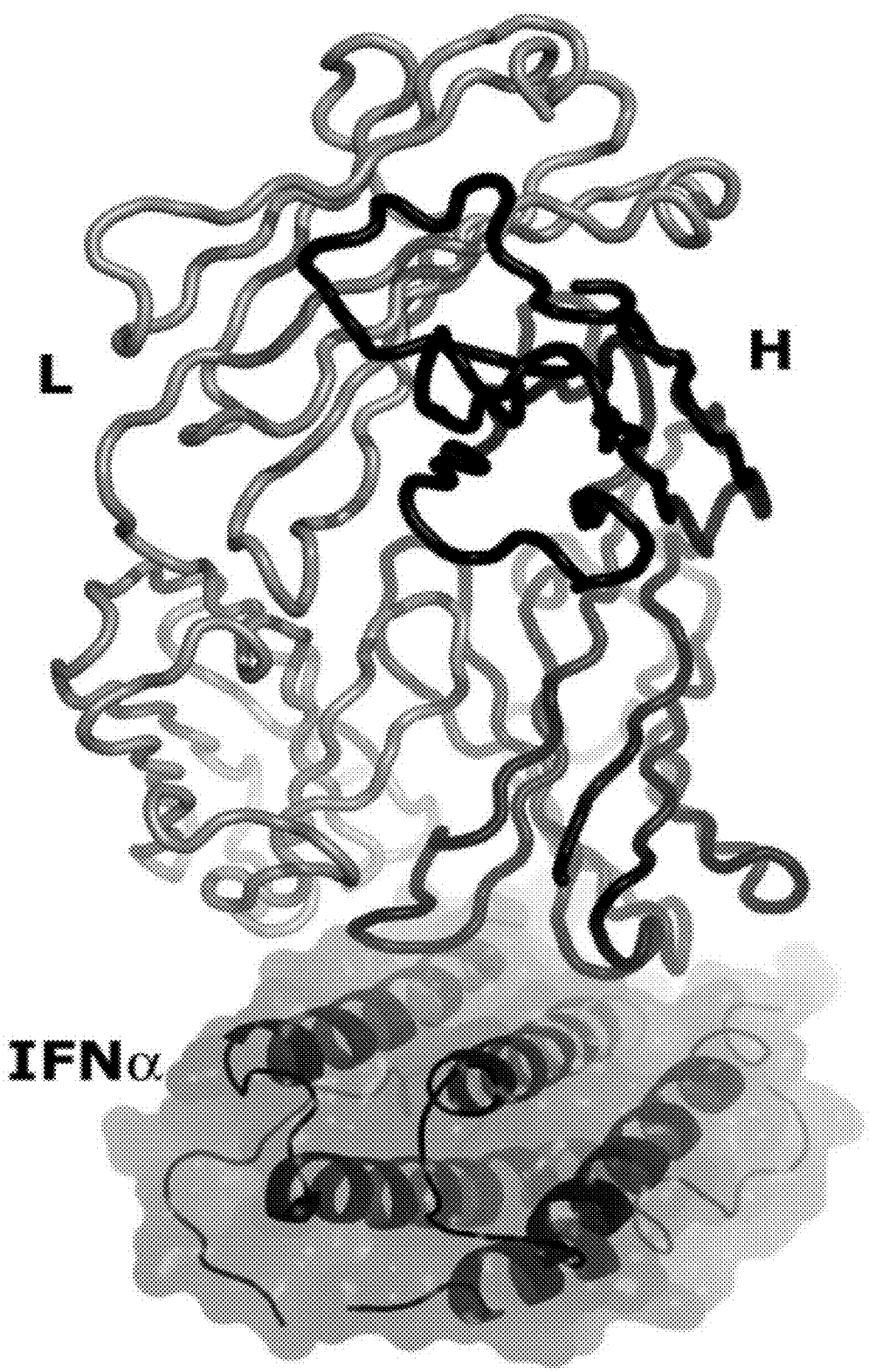
FIG. 8 shows the structure of hzACO-1 Fab fragment chains (H, L) bound to IFN-α8, determined by X-ray crystallography.

The crystal structure of IFN-α8 in complex with the Fab fragment of hzACO-1 was determined and refined to 3.3 Å resolution using X-ray crystallography (FIG. 8).

Materials and Methods

IFN-α8 (amino acid 1-166 of SEQ ID NO: 30, and hzACO-1 Fab (with the light chain sequence of SEQ ID NO:

TABLE 4

| | Expression analysis | | | | | |
|---|---|---|---|---|---|---|
| | Expression Yield (mg/L) | Standard deviation (Expression Yield) | Viable Cell Density (×10E5 cell/ml) | Standard deviation (Viable Cell Density) | Cell viability (%) | Standard deviation (Cell viability) |
| hzACO-1 | 41 | 0.9 | 19 | 0.2 | 65 | 2.1 |
| hzACO-1-Kabat CDRH2 | 22 | 0.7 | 18 | 0.5 | 65 | 3.2 |

32 and heavy chain sequence of residues 1-221 of SEQ ID NO: 31) were mixed, with a slight excess of IFN-α8, and the complex was purified on a gel-filtration column. The protein complex hzACO-1-Fab/IFN-α8 was put in a buffer of 25 mM HEPES buffer, pH 7.5, +25 mM NaCl and concentrated to 5 mg/ml. The complex was crystallized in 100 mM HEPES buffer, pH 7.5, 15% PEG 10,000 and 15% Ethylene glycol, the precipitant solution. Prior to diffraction data collection, the crystal was flash frozen in liquid $N_2$. The crystal was first transferred to a cryo solution which was a mix of 25% v/v 99% glycerol and 75% of the precipitant solution. Diffraction data were collected at beamline BLI911-3, MAX-Lab, Lund, Sweden. Diffraction data were indexed and integrated using the XDS program package (Kabsch, J. Appl. Crystallogr. 1993; 26:795-800).

The three-dimensional structure was determined using the Molecular Replacement (MR) method using the PHASER program (Read, 2001, Acta Crystallogr. Sect. D-Biol. Crystallogr. 57, 1373-1382) of the CCP4 package (Baily, 1994, Acta Crystallogr. Sect. D-Biol. Crystallogr. 50, 760-763). The crystal structure of the hzACO-1 Fab, un-complexed, was earlier been determined to 1.52 Å resolution (R- and R-free 0.18 and 0.21, respectively), data not shown. Those 3D coordinates were subsequently used in the MR calculations for the hzACO-1/IFN-α8 complex. The search models were divided into three parts: 1) the variable domain of hzACO-1 Fab), 2) the constant domain of the hzACO-1 Fab and 3) the PDB deposited IFNtau model, Protein Data Bank (Berman et al., 2000, Nucleic Acids Res. 28, 235-242) accession code 1B5L (RADHAKRISHNAN et al, 1999, J. MOL. BIOL. v. 286 pp. 151), mutated by the COOT program to obtain the sequence of IFN-α8, SEQ ID NO: 30. The final space group determination was made by the PHASER program. The highest scores were obtained for space group $P4_1$ with rotation function peaks, RZ's, of 10.7, 4.4 and 2.6 σ, respectively, translation peaks, TZ's, of 24.1, 26.4 and 8.0 σ, respectively, log-likelihood gains, LLG's, of 383, 918 and 1134, respectively, and with no overlaps to symmetry related molecules.

Molecular replacement was followed by some adjustments to the model in the COOT molecular graphics program after which torsional simulated annealing up to 2000 K was applied twice, without refinement of individual temperature factors. Original R- and R-free values were 0.416 and 0.439, respectively, and final values after simulated annealing were 0.314 and 0.427, respectively. The model was then subject to manual intervention in the COOT program followed refinements using the REFMAC5 program (Murshudov et al., 1997, Acta Crystallogr. Sect. D-Biol. Crystallogr. 53, 240-255) resulting in R- and R-free values of 0.216 and 0.348, respectively. The model comprised residues 1-21, while residues 22-23 were refined as Ala residues, 28-101 and 114-164 of IFN-α8, 1-215 of the hzACO-1 light chain and 1-219 of the hzACO-1 heavy chain.

The relatively large difference between R- and R-free seen in the refinement are due to the limited resolution of the data, 3.3 Å, and that there are substantial stretches of the IFN-α8 X-ray model that are completely missing in the interpretation of the electron density map. The electron density maps clearly define the residues in the stabilised interface of IFN-α8 to hzACO-1-Fab, while details of the IFN-α8 X-ray structure model away from the antibody site are less well defined and therefore less accurately determined.

Results

The contacts were identified by the CONTACT computer program of the CCP4 suite using a cut-off distance of 4.0 Å between the Fab and IFN-α8 molecules. The resulting epitope for human hzACO-1 was found to comprise the following residues of IFN-α8 (SEQ ID NO: 30): Ser 55, His 58, Glu 59, Gln 62, Gln 63, Asn 66, Glu 97, Leu 118, Arg 121, Lys 122, Phe 124, Gln 125, Arg 126, Thr 128, Leu 129, Thr 132). Residues of hzACO-1 involved in interactions with IFN-α8, the paratope, included Ser 32, Tyr 33, Tyr 35, Tyr 50, Ser 51, Trp 92, Ser 93, Tyr 95 and Phe 97 of the hzACO-1 light (L) chain, (Numbering according to SEQ ID NO: 32, not Kabat, and Thr 30, Asn 31, Tyr 32, Trp 33, His 35, Glu 50, Asn 52, Ser 54, His 55, Arg 57, Leu 101, Gly 102, Trp 105 of the heavy (H) chain, Table 9 (Numbering according to SEQ ID NO: 31, not Kabat).

```
>IFN_a8
                                                          SEQ ID NO: 30
CDLPQTHSLGNRRALILLAQMRRISPFSCLKDRHDFEFPQEEFDDKQFQKAQAISVLHEM
IQQTFNLFSTKDSSAALDETLLDEFYIELDQQLNDLESCVMQEVGVIESPLMYEDSILAV
RKYFQRITLYLTEKKYSSCAWEVVRAEIMRSFSLSINLQKRLKSKE hzACO-1 LC
                                                          SEQ ID NO: 32
  1   EIVLTQSPAT  LSLSPGERAT  LSCSAGSSVD  SSYLYWYQQK  PGQAPRLLIY
 51   STSNLASGIP  ARFSGSGSGT  DFTLTISSLE  PEDFAVYYCH  QWSSYPFTFG
101   QGTKLEIKRT  VAAPSVFIFP  PSDEQLKSGT  ASVVCLLNNF  YPREAKVQWK
151   VDNALQSGNS  QESVTEQDSK  DSTYSLSSTL  TLSKADYEKH  KVYACEVTHQ
201   GLSSPVTKSF  NRGEC hzACO-1 Fab HC
                                                          SEQ ID NO: 31
  1   QVQLVQSGAE  VKKPGASVKV  SCKASGYTFT  NYWMHWVRQA  PGQGLEWMGE
 51   INPSHGRTIY  AQKFQGRVTM  TRDTSTSTVY  MELSSLRSED  TAVYYCARGG
101   LGPAWFAYWG  QGTLVTVSSA  STKGPSVFPL  APCSRSTSES  TAALGCLVKD
151   YFPEPVTVSW  NSGALTSGVH  TFPAVLQSSG  LYSLSSVVTV  PSSSLGTKTY
201   TCNVDHKPSN  TKVDKRVESK
```

As can be seen in FIG. 9 the hzACO-1 interaction epitope on IFN-α8 overlaps, partly, the IFNAR1 binding epitope while the IFNAR2 binding epitope is distant from the hzCAO-1 binding epitope. That suggests that the neutralization of IFN-α by hzACO-1 occurs by neutralization of IFN-α binding to IFNAR1, but not IFNAR2. Accordingly, it may be envisioned that hzACO-1 binds the IFN-α/IFNAR2 complex but inhibits formation of the ternary receptor complex IFN-α/IFNAR1/IFNAR2 responsible for intracellular signaling.

TABLE 5

Parameters of the IFN-α8: hzACO-1-Fab complex crystal used for structure determination

| Space Group: | $P4_1$ | | |
|---|---|---|---|
| Cell Parameters [Å]: | a | b | c |
| | 112.74 | 112.74 | 60.55 |
| Molecular complexes/asymmetric unit: | 1 | | |

TABLE 6

X-ray data statistics from the program XSCALE of the XDS package

| RESOLU-TION [Å] | NUMBER OF REFLECTIONS | | | COMPLETE-NESS | R-FACTOR | | COM-PARED | I/SIGMA | R-Rmrgd-F | | S_norm/S_ano |
|---|---|---|---|---|---|---|---|---|---|---|---|
| | OBSERVED | UNIQUE | POSSIBLE | | observed | expected | | | R- | Rmrgd-F | |
| 10.00 | 984 | 353 | 453 | 77.9% | 4.4% | 4.9% | 984 | 18.84 | 5.4% | 4.1% | −1% |
| 6.00 | 4237 | 1461 | 1562 | 93.5% | 6.8% | 7.2% | 4237 | 12.45 | 8.2% | 7.8% | 1% |
| 5.00 | 3922 | 1343 | 1411 | 95.2% | 9.7% | 10.1% | 3922 | 9.83 | 11.7% | 11.1% | 3% |
| 4.00 | 8747 | 3063 | 3182 | 96.3% | 11.6% | 11.9% | 8747 | 8.59 | 14.0% | 13.7% | 8% |
| 3.50 | 8588 | 3106 | 3212 | 96.7% | 24.8% | 24.9% | 8588 | 4.43 | 30.3% | 31.3% | 9% |
| 3.45 | 1102 | 397 | 410 | 96.8% | 36.9% | 37.8% | 1102 | 3.17 | 45.0% | 44.4% | 7% |
| 3.40 | 1198 | 448 | 464 | 96.6% | 41.8% | 41.3% | 1198 | 2.82 | 52.3% | 48.7% | −12% |
| 3.35 | 1271 | 468 | 495 | 94.5% | 56.0% | 51.5% | 1271 | 2.33 | 69.9% | 66.9% | 1% |
| 3.30 | 1317 | 486 | 502 | 96.8% | 59.6% | 51.2% | 1317 | 2.14 | 74.9% | 67.4% | −8% |
| total | 31366 | 11125 | 11691 | 95.2% | 14.1% | 14.2% | 31366 | 7.44 | 17.2% | 20.2% | 6% |

TABLE 7

Statistics from the last refinement cycle of
IFN-α8: hzACO-1-Fab of the REFMAC program.

DATA USED IN REFINEMENT.

| | |
|---|---|
| RESOLUTION RANGE HIGH (ANGSTROMS) | 3.30 |
| RESOLUTION RANGE LOW (ANGSTROMS) | 20.23 |
| DATA CUTOFF (SIGMA(F)) | NONE |
| COMPLETENESS FOR RANGE (%) | 95.66 |
| NUMBER OF REFLECTIONS | 10571 |

FIT TO DATA USED IN REFINEMENT.

| | |
|---|---|
| CROSS-VALIDATION METHOD | THROUGHOUT |
| FREE R VALUE TEST SET SELECTION | RANDOM |
| R VALUE (WORKING + TEST SET) | 0.22272 |
| R VALUE (WORKING SET) | 0.21646 |
| FREE R VALUE | 0.34845 |
| FREE R VALUE TEST SET SIZE (%) | 5.0 |
| FREE R VALUE TEST SET COUNT | 552 |

FIT IN THE HIGHEST RESOLUTION BIN.

| | |
|---|---|
| TOTAL NUMBER OF BINS USED | 20 |
| BIN RESOLUTION RANGE HIGH | 3.300 |
| BIN RESOLUTION RANGE LOW | 3.384 |
| REFLECTION IN BIN (WORKING SET) | 761 |
| BIN COMPLETENESS (WORKING + TEST) (%) | 96.06 |
| BIN R VALUE (WORKING SET) | 0.290 |
| BIN FREE R VALUE SET COUNT | 44 |
| BIN FREE R VALUE | 0.446 |

B VALUES.

| | |
|---|---|
| FROM WILSON PLOT (A**2) | NULL |
| MEAN B VALUE (OVERALL, A**2) | 52.314 |

OVERALL ANISOTROPIC B VALUE.

| | |
|---|---|
| B11 (A**2) | −0.96 |
| B22 (A**2) | −0.96 |
| B33 (A**2) | 1.92 |
| B12 (A**2) | 0.00 |
| B13 (A**2) | 0.00 |
| B23 (A**2) | 0.00 |

ESTIMATED OVERALL COORDINATE ERROR.

| | |
|---|---|
| ESU BASED ON R VALUE (A) | NULL |
| ESU BASED ON FREE R VALUE (A) | 0.776 |
| ESU BASED ON MAXIMUM LIKELIHOOD (A) | 0.574 |
| ESU FOR B VALUES BASED ON MAXIMUM LIKELIHOOD (A**2) | 33.433 |

CORRELATION COEFFICIENTS.

| | |
|---|---|
| CORRELATION COEFFICIENT FO-FC | 0.901 |
| CORRELATION COEFFICIENT FO-FC FREE | 0.727 |

| RMS DEVIATIONS FROM IDEAL VALUES | COUNT | RMS | WEIGHT |
|---|---|---|---|
| BOND LENGTHS REFINED ATOMS (A) | 4628 | 0.014 | 0.022 |
| BOND ANGLES REFINED ATOMS (DEGREES) | 6285 | 1.738 | 1.953 |
| TORSION ANGLES, PERIOD 1 (DEGREES) | 577 | 8.885 | 5.000 |

TABLE 7-continued

Statistics from the last refinement cycle of
IFN-α8: hzACO-1-Fab of the REFMAC program.

| | | | |
|---|---|---|---|
| TORSION ANGLES, PERIOD 2 (DEGREES) | 195 | 40.409 | 24.205 |
| TORSION ANGLES, PERIOD 3 (DEGREES) | 770 | 23.636 | 15.000 |
| TORSION ANGLES, PERIOD 4 (DEGREES) | 22 | 18.930 | 15.000 |
| CHIRAL-CENTER RESTRAINTS (A**3) | 704 | 0.110 | 0.200 |
| GENERAL PLANES REFINED ATOMS (A) | 3478 | 0.007 | 0.021 |

TABLE 8

IFN-α8 - hzACO-1 Fab L chain interactions.

| IFN-α8 Atoms | | hzACO-1 Fab L Atoms | | Distance (Å) |
|---|---|---|---|---|
| Leu | 118I CB | Tyr | 95L CE2 | 3.78 |
| Leu | 118I CG | Tyr | 95L CE2 | 3.68 |
| | | Tyr | 95L CD2 | 3.90 |
| Leu | 118I CD1 | Tyr | 95L CG | 3.95 |
| | | Tyr | 95L CE2 | 3.53 |
| | | Tyr | 95L CD2 | 3.21 |
| | | Ser | 93L O | 3.70 |
| | | Tyr | 95L N | 3.96 |
| | | Phe | 97L CE1 | 3.62 |
| Leu | 118I CD2 | Trp | 92L O | 3.84 |
| Arg | 121I NH2 | Tyr | 95L OH | 3.93* |
| Lys | 122I CA | Tyr | 33L OH | 3.38 |
| Lys | 122I CB | Tyr | 33L OH | 3.12 |
| Lys | 122I CG | Tyr | 33L CE1 | 3.75 |
| | | Tyr | 33L CZ | 3.37 |
| | | Tyr | 33L OH | 2.93 |
| Lys | 122I CD | Tyr | 33L CZ | 3.74 |
| | | Tyr | 33L OH | 3.40 |
| Lys | 122I CE | Tyr | 33L OH | 3.33 |
| Lys | 122I C | Tyr | 33L OH | 3.70 |
| Lys | 122I O | Tyr | 33L OH | 3.41* |
| Gln | 125I CG | Trp | 92L CH2 | 3.18 |
| | | Tyr | 33L CE1 | 3.80 |
| | | Trp | 92L CZ2 | 3.63 |
| Gln | 125I CD | Trp | 92L CH2 | 3.70 |
| | | Tyr | 35L OH | 3.81 |
| | | Trp | 92L CZ2 | 3.58 |
| Gln | 125I OE1 | Tyr | 35L OH | 3.50* |
| Gln | 125I NE2 | Ser | 32L O | 3.24*** |
| | | Ser | 51L OG | 3.37* |
| | | Tyr | 33L CE1 | 3.94 |
| | | Tyr | 35L OH | 3.59* |
| | | Trp | 92L CZ2 | 3.67 |
| Arg | 126I CD | Tyr | 33L OH | 3.94 |
| Leu | 129I CD1 | Ser | 51L CB | 3.80 |
| | | Ser | 51L OG | 3.77 |
| | | Ser | 32L OG | 3.40 |
| Leu | 129I CD2 | Ser | 51L OG | 3.90 |
| Thr | 132I OG1 | Tyr | 50L OH | 3.90* |

A cut-off of 4.0 Å was used. The contacts were identified by the CONTACT computer program of the CCP4 suite. In the last column "***" indicates a strong possibility for a hydrogen bond at this contact (distance <3.3 Å) as calculated by CONTACT, "*" indicates a weak possibility (distance >3.3 Å). Blank indicates that the program considered there to be no possibility of a hydrogen bond.

TABLE 9

IFN-α8 - hzACO-1 Fab H chain interactions.

| IFN-α8 Atoms | | hzACO-1 Fab H Atoms | | Distance (Å) |
|---|---|---|---|---|
| Ser | 55I CB | Arg | 57H NH2 | 3.58 |
| Ser | 55I OG | Arg | 57H NE | 3.18*** |
| | | Arg | 57H CZ | 3.30 |
| | | Arg | 57H NH2 | 2.80*** |
| His | 58I CG | His | 55H CD2 | 3.73 |
| His | 58I CE1 | Asn | 52H ND2 | 3.94 |
| | | Ser | 54H CB | 3.90 |
| | | Ser | 54H OG | 3.79 |
| His | 58I NE2 | His | 55H CD2 | 3.53 |
| | | Ser | 54H CB | 3.60 |
| | | Ser | 54H OG | 3.20*** |
| His | 58I CD2 | His | 55H CD2 | 3.19 |
| Glu | 59I CD | Trp | 33H NE1 | 3.90 |
| Glu | 59I OE2 | Trp | 33H CD1 | 3.74 |
| | | Trp | 33H NE1 | 3.01*** |
| Gln | 62I CD | Asn | 52H OD1 | 3.44 |
| | | Thr | 30H O | 3.71 |
| Gln | 62I OE1 | Asn | 52H CG | 3.91 |
| | | Asn | 52H OD1 | 3.02*** |
| | | Ser | 54H CB | 3.67 |
| | | Thr | 30H C | 3.69 |
| | | Thr | 30H O | 2.55*** |
| | | Asn | 31H CA | 3.87 |
| Gln | 62I NE2 | Asn | 52H CG | 3.77 |
| | | Asn | 52H OD1 | 3.13*** |
| | | Asn | 52H ND2 | 3.95 * |
| Gln | 63I CD | Leu | 101H CD1 | 3.83 |
| Gln | 63I OE1 | Leu | 101H CG | 3.87 |
| | | Leu | 101H CD1 | 2.96 |
| Gln | 63I NE2 | Leu | 101H CD2 | 3.79 |
| Asn | 66I CG | Asn | 31H O | 3.94 |
| Asn | 66I OD1 | Tyr | 32H CE1 | 3.54 |
| | | Asn | 31H CB | 3.89 |
| | | Asn | 31H C | 3.86 |
| | | Asn | 31H O | 2.80*** |
| | | Tyr | 32H CZ | 3.82 |
| Asn | 66I ND2 | Asn | 31H OD1 | 3.79* |
| Glu | 97I CG | Ser | 54H OG | 3.85 |
| Glu | 97I CD | Ser | 54H O | 3.97 |
| | | Ser | 54H OG | 3.24 |
| Glu | 97I OE1 | Ser | 54H O | 3.54* |
| Glu | 97I OE2 | Ser | 54H CB | 3.88 |
| | | Ser | 54H OG | 2.56*** |
| Arg | 121I CZ | Glu | 50H CD | 3.73 |
| | | Glu | 50H OE1 | 3.31 |
| | | Glu | 50H OE2 | 3.30 |
| Arg | 121I NH1 | His | 35H CE1 | 3.89 |
| | | Glu | 50H CD | 3.78 |
| | | Glu | 50H OE1 | 3.06*** |
| | | Glu | 50H OE2 | 3.66* |
| | | Trp | 105H CZ3 | 3.82 |
| Arg | 121I NH2 | Glu | 50H CD | 3.08 |
| | | Glu | 50H OE1 | 2.80*** |
| | | Glu | 50H OE2 | 2.73*** |
| | | Trp | 33H CG | 3.66 |
| | | Trp | 33H CE2 | 3.33 |
| | | Trp | 33H CD2 | 3.51 |
| | | Trp | 33H CZ2 | 3.88 |
| | | Trp | 33H CD1 | 3.54 |
| | | Trp | 33H NE1 | 3.35* |
| Phe | 124I CB | Leu | 101H CD1 | 3.79 |
| Gln | 125I CD | Gly | 102H N | 3.69 |
| Gln | 125I OE1 | Leu | 101H CA | 3.76 |
| | | Leu | 101H CB | 3.38 |
| | | Leu | 101H C | 3.57 |
| | | Gly | 102H N | 2.55*** |
| | | Gly | 102H CA | 3.24 |
| Thr | 128I OG1 | Leu | 101H CB | 3.84 |

A cut-off of 4.0 Å was used. The contacts were identified by the CONTACT computer program of the CCP4 suite. In the last column "***" indicates a strong possibility for a hydrogen bond at this contact (distance <3.3 Å) as calculated by CONTACT, "*" indicates a weak possibility (distance >3.3 Å). Blank indicates that the program considered there to be no possibility of a hydrogen bond.

Example 7

Design of Structure Based Mutations for Affinity Maturation of hzACO-1

If the epitope and paratope of an antibody/antigen complex is not known, a large number of possible amino acid residues may be prone for mutations in order to improve the affinity of an antibody and moreover, they can be converted into any of the 20 remaining amino acid residues to identify the optimal residue at the particular position. The CDR region holds approximately 54 residues available for mutations. Thus, in order to improve the affinity of the interaction 54×20=1080 analogues may be generated only within the CDRs. In addition, mutations outside the CDRs may be made in order to improve affinity.

However, when the structure of the antibody/antigen is know, a more limited number of qualified mutations that improve affinity may be predicted and analysed, based on structural predictions. Accordingly, based on the crystal structure of IFN-α8 in complex with the Fab fragment of hzACO-1, as described in Example 6, three mutants that improve hzACO-1 binding to all IFN-α subtypes were identified. The 3 mutants are hzACO-1 HC T30R, hzACO-1 LC Y32E and the combined hzACO-1 Y32E, T30R (residue numbering according to Kabat). The identification of the mutants is described below.

LC Y32E: It can be seen that the electron density for residues Lys 122 of IFN-α8, which is part of the binding epitope to hzACO-1, indicates a rather high mobility. Moreover, the atom Oη of residue Tyr 32 (Kabat notation) of the hzACO-1 light chain is directed towards the Cβ and Cγ atoms of the Lys 122 side chain. That interaction is not any optimal residue-residue interaction. Mutating the light chain Tyr 32 to a negatively charged residue like Glu, or Asp, make the possibility of forming a strong ionic bond between the antibody light chain Tyr 32 residue and the positively charged Lys 122 residue of IFN-α8. For that reason Y was exchanged for E in order to improve the affinity of the hzACO-1 antibody.

HC T30R: For each hzACO-1 residue close to IFN-α8 in the X-ray structure, the following properties were calculated: number of core side chain atoms (core), number of periphery sidechain atoms (peri), number of charged interactions (char), number of hydrogen bonds (hybo) and number of hydrophobic interactions (hyph) and given in Table 10 below:

TABLE 10

Properties of amino acids of the hzACO-1 mAb

| Kabat | Res | core | peri | char | hybo | hyph |
|---|---|---|---|---|---|---|
| Light Chain ||||||||
| 29 | D | 1 | 2 | 1 | | |
| 31 | S | 2 | | | | 1 |
| 32 | Y | 5 | 3 | | | 6 |
| 34 | Y | 3 | | | | 2 |
| 49 | Y | 3 | 1 | | 1 | 2 |
| 50 | S | 2 | | | | 8 |
| 53 | N | 1 | 3 | | | 1 |
| 91 | W | 5 | 2 | | | 9 |
| 92 | S | | 1 | | | |
| 93 | S | | | | | 4 |
| 94 | Y | 6 | 2 | | | |
| 96 | F | 2 | 2 | | | |
| Heavy Chain ||||||||
| 28 | T | | 3 | | | |
| 30 | T | | 3 | | | |
| 31 | N | 4 | | | | 1 |
| 32 | Y | 6 | 2 | | | 1 |
| 33 | W | 10 | | | | 3 |
| 35 | H | 2 | 2 | | | |
| 50 | E | 4 | 1 | 1 | 1 | |
| 52 | N | 3 | 1 | | 1 | |
| 52A | P | | 1 | | | |
| 53 | S | 2 | | | 2 | |
| 54 | H | 4 | 2 | | | 6 |
| 56 | R | 5 | 2 | 1 | 1 | |
| 58 | I | 2 | 2 | | | 2 |
| 64 | Q | | 1 | | | |
| 71 | R | | 1 | 1 | | |
| 97 | L | 4 | | | | 3 |
| 98 | G | | | | 1 | |
| 99 | P | | 2 | | | |
| 100A | W | 2 | 3 | | | 1 |

The number of core and periphery atoms were calculated by overlaying the X-ray structure onto a 101×101×101 node grid and for each grid point calculating the number of atoms <2.5 Å ($N_{ex}$) and atoms <3.5 Å ($N_{in}$) from the node. Core nodes have $N_{ex}$>0 covering atoms from both hzACO-1 and IFN-8. Periphery nodes have $N_{ex}$=0 and $N_{in}$>0 covering atoms from both hzACO-1 and IFN-α8. Core sidechain atoms are now atoms <2.5 Å from any node. Periphery sidechain atoms are now atoms 2.5 Å & <3.5 Å from any node.

Finally periphery residues are defined as residues with only periphery atoms and no interactions, so they can be modified to create binding. LC S92, HC T28, HC T30, HC P52, HC Q64 and HC P99 have be identified. Focusing on heavy chain non-prolines, it is seen by visual inspection that the mutation HC T28R would have a possible interaction with D90, HC T30R would have a possible interaction with both D90 and E97 and Q64R would have a possible interaction with E114, but other similar mutations can also be applied. Since only E97 is conserved across all interferon alphas, HC T30R is expected to give the best binding with a similar profile as hzACO-1.

The specific mutation HC T30R was designed to establish a charge-charge interaction in the periphery of the binding site to improve the affinity of hzACO-1.

Furthermore, a double mutant containing both the LC Y32E and the HC T30R mutations, termed hzACO-1 Y32E, T30R was generated and analyzed to determine if the two mutations would have additive effects.

Example 8

Determination of the Kinetic Parameters for the Interaction Between hzACO-1, hzACO-1 Variants and Recombinant Human IFN-α Subtypes Protein interactions can be monitored in real-time using surface plasmon resonance (SPR) analysis. In this study, SPR analysis was performed on Biacore® 3000 and Biacore® T100 instruments in order to characterize the anti-IFNα monoclonal antibody hzACO-1 and variants thereof, with respect to affinity towards various subtypes of recombinant human Interferon alpha (IFN-α).

Affinity studies were performed using a direct binding procedure, with the respective monoclonal antibody covalently coupled via free amine groups to the carboxymethylated dextrane membrane (CM5) on the sensor chip surface. Recombinant IFN-α subtypes (PBL Biomedical Laboratories, NJ, USA) were injected in various concentrations, followed by a dissociation period with constant buffer flow over the sensor chip surface. Using this experimental design, the binding of IFN-α to the immobilized monoclonal antibody can be regarded as a 1:1 binding, with one IFN-α molecule binding to one antibody binding site. The kinetic parameters for the interaction can be calculated using a 1:1 interaction langmuir fitting model.

The purified monoclonal antibodies were immobilized in individual flow cells on a CM5 type sensor chip. Immobilizations were performed using a standard amine coupling procedure, aiming for an immobilization level of 1000 Resonance Units (RU).

HBS-EP pH 7.4 (10 mM HEPES, 150 mM NaCl, 3 mM EDTA and 0.005% Polysorbat P20) was used as running buffer, and diluent for the recombinant IFN-α's. Association (injection) was 4 min., followed by a 12 to 30 min. dissociation period. Flow rate was 50 ul/min. Experiments were performed at 25° C. Detection in all flow cells simultaneously. Flow cell #1 contained no immobilized antibody, and was used for subtraction of background and bulk.

The kinetic parameters were calculated by global fitting of the data for a given antibody-antigen combination using a 1:1 langmuir binding model. Data was inspected for mass-transport limitations prior to calculation of the kinetic parameters.

Experiments were performed on Biacore® 3000 and T100 instruments. Data was evaluated using Biaeval™ 4.1 and Biacore® T100 evaluation software.

The kinetic parameters obtained are valid only in the buffer used, and with the recombinant form of the antigen.

Results

In order to generate a humanized ACO-1 antibody with retained affinity a number of humanized variants were generated as described in example 2, 3 and 7, using different strategies. The kinetic parameters for the interaction between recombinant human IFN-α subtypes and variants of hzACO-1 was obtained by SPR analysis. As seen in Table 11 even-though hzACO-1, generated as described in example 2 contains a truncated CDR H2 and no backmutations, the affinity of the hzACO-1 has been retained as compared to the murine ACO-1, as shown by the KD of the hzACO-1 being within two-fold of the mouse antibody. Accordingly, no further backmutations from human to mouse ACO-1 in the framework regions were required for humanization, as identified and described in example 2. In addition, the IFN-α subtype profile of the hzACO-1 antibody had been retained, as shown in Table 2.

The kinetic parameters for the interaction of hzACO-1 as compared to a humanized ACO-1 molecule generated by traditional CDR grafting and accordingly contains a large murine CDR H2 (designated hzACO-1-kabat CDRH2), with recombinant human IFN-αA are listed in Table 12. As shown, the affinity of the hzACO-1 molecule, humanized as described in example 2 and containing a shorter CDR H2 than the hzACO-1-kabat CDRH2 molecule, were equal, showing that the humanization process described in example 2 generates a humanized variant as good as that generated by simple CDR grafting, while having a more human sequence.

TABLE 12

Kinetic parameters for the interaction of recombinant IFN-αA with hzACO-1 and hzACO-1-kabat CDRH2.

| mAb | KD (M) | ka (1/Ms) | kd (1/s) | KD mAb/ KD hzACO-1 |
|---|---|---|---|---|
| hzACO-1 | 1.9E+09 | 2.22E+05 | 4.15E−04 | 1 |
| hzACO-1-kabat CDRH2 | 1.7E+09 | 2.05E+05 | 3.41E−04 | 0.9 |

KD is the equilibrium dissociation constant, ka is the association rate constant and kd is the dissociation rate constant.

Furthermore, in order to investigate if the hzACO-1 and the hzACO-1-kabat CDRH2 had comparable kinetic parameters of the binding to various subtypes of human IFN-α, a dissociation comparison experiment was performed on selected human IFN-α subtypes (Table 13). This shows that the affinity of the hzACO-1 appears to be retained as compared to hzACO-1-kabat CDRH2 to all tested subtypes despite having a shorter mouse CDR H2 sequence.

TABLE 13

Comparison of dissociation rate constants (kd) of the interaction between various subtypes of recombinant human IFN-αA with hzACO-1 and hzACO-1-kabat CRH2 respectively.

| | mAb | | |
|---|---|---|---|
| Subtype | hzACO-1 kd (1/s) | hzACO-1-kabat CDRH2 kd (1/s) | hzACO-1/hzACO-1-kabat CDRH2 Ratio |
| IFN-αH2 | 4.13E−04 | 3.28E−04 | 1.26 |
| IFN-αK | 2.89E−04 | 3.41E−04 | 0.85 |
| IFN-α4b | 2.17E−04 | 1.55E−04 | 1.40 |
| IFN-αWA | 2.91E−04 | 3.66E−04 | 0.80 |

TABLE 11

Kinetic parameters for the interaction of recombinant IFN-αA with ACO-1 and hzACO-1 variants.

| Anti-IFN-α mAb | KD (M) | ka (1/Ms) | kd (1/s) | KD mAb/KD hzACO-1 |
|---|---|---|---|---|
| ACO-1 | 3.09E−09 | 1.24E+05 | 3.75E−04 | 0.60 |
| hzACO-1 | 4.46E−09 | 1.24E+05 | 5.56E−04 | 1 |
| hzACO-1-L33F | 4.86E−09 | 1.89E+05 | 9.18E−04 | 1.17 |
| hzACO-1-S50G | 4.94E−09 | 1.98E+05 | 9.78E−04 | 1.19 |
| hzACO-1-T28S | 2.97E−09 | 1.58E+05 | 4.68E−04 | 0.63 |
| hzACO-1-N31S | 2.20E−09 | 1.16E+05 | 2.55E−04 | 0.61 |
| hzACO-1-I58S | 1.93E−08 | 1.93E+05 | 3.74E−03 | 4.09 |
| hzACO-1-S76N | 5.07E−09 | 1.16E+05 | 5.88E−04 | 1.09 |
| hzACO-1-T77I | 6.79E−09 | 9.80E+04 | 6.65E−04 | 1.46 |
| hzACO-1-A93V | 2.16E−09 | 1.08E+05 | 2.34E−04 | 0.60 |
| hzACO-1-T28S, N31S | 2.22E−09 | 1.56E+05 | 3.45E−04 | 0.77 |
| hzACO-1-N31S, A93V | 1.51E−09 | 1.59E+05 | 2.40E−04 | 0.52 |
| hzACO-1-T28S, A93V | 1.66E−09 | 1.61E+05 | 2.68E−04 | 0.69 |
| hzACO-1-T28S, N31S, A93V | 1.57E−09 | 1.85E+05 | 2.91E−04 | 0.65 |

KD is the equilibrium dissociation constant, ka is the association rate constant and kd is the dissociation rate constant.

In order to try to improve the affinity of hzACO-1 beyond that of the mouse ACO-1 antibody, the kinetic of the parameters between IFN-αA and different hzACO-1 variants containing mutations based on the ACO-2 sequence were measured (Table 11). In order to correlate the parameters obtained in the separate experiments performed, the KD value of each individual antibody was normalized against that of hzACO-1 in the same experiment, and the relation of the KD value of the individual mAb to the KD of hzACO-1 in the same experiment is shown in the column "KD mAb vs. KD hzACO-1".

The affinity determination further demonstrated KD values of all ACO2 derived hzACO-1 antibody variants (except hzACO-1-I58S) in the lower nM range. The minor variations in the KD values are predominantly related to differences in the kd. Introduction of the single amino acid substitutions N31S, A93V, or T28S, and combinations thereof, in the hzACO-1 slightly increased the affinity to a level similar to that of ACO-1. The hzACO-1-I58S mutation has a pronounced negative effect on the kd value, demonstrating the importance of this particular amino acid for the stability of the hzACO-1/IFNα-A complex.

Based on the hzACO-1 Fab/IFN-α8 crystal structure, a number of amino acid substitutions were introduced in hzACO-1 in order to increase the affinity even further (see example 7). Of these, two single substitutions, Y32E of the light chain and T30R of the heavy chain, had significant positive effects on the affinity (Table 14) increasing the affinity approximately 2 and 6 fold respectively, against IFN-αA. Remarkably, by combining the two mutations the hzACO-1 construct containing both the Y32E and T30R an approximately 10 fold increase in affinity was observed against IFN-αA (Table 15).

TABLE 14

Kinetic parameters for the interaction of recombinant IFN-αA with hzACO-1 and hzACO-1 variants respectively.

| mAb | KD (M) | ka (1/Ms) | kd (1/s) | KD mAb/ KD hzACO-1 |
|---|---|---|---|---|
| hzACO-1 | 3.20E−09 | 1.39E+05 | 4.43E−04 | 1 |
| hzACO-1 LC Y32E | 1.54E−09 | 2.47E+05 | 3.81E−04 | 0.5 |
| hzACO-1 HC T30R | 5.40E−10 | 1.31E+05 | 7.08E−05 | 0.16 |

KD is the equilibrium dissociation constant, ka is the association rate constant and kd is the dissociation rate constant.

TABLE 15

Kinetic parameters for the interaction of recombinant IFN-αA with hzACO-1 and hzACO-1 Y32E, T30R respectively.

| mAb | KD (M) | ka (1/Ms) | kd (1/s) | KD mAb/ KD hzACO-1 |
|---|---|---|---|---|
| hzACO-1 | 2.72E−09 | 1.78E+05 | 4.85E−04 | 1 |
| hzACO-1 Y32E, T30R | 2.97E−10 | 1.49E+05 | 4.43E−05 | 0.1 |

KD is the equilibrium dissociation constant, ka is the association rate constant and kd is the dissociation rate constant.

The kinetic data in Table 16 illustrate, that a hzACO-1 Y32E, T30R construct generated based on a rational design approach, had retained its IFN-α subtype profile as it does not bind to IFN-α1 but does bind to the remaining subtypes tested. In order to validate that the effect on the kinetic parameters caused by the Y32E, T30R mutations were reflected in the binding to various subtypes of human IFN-α, a dissociation comparison experiment was performed on selected human IFN-α subtypes (Table 16). Although the suggested mutations of the double mutant hzACO-1 construct were based on the structure of the IFN-α8, unpredictably the improved off-rates were observed for all tested human IFN-α subtypes varying between 6-64 fold.

TABLE 16

Comparison of dissociation rate constants (kd) of the interaction between various subtypes of recombinant human IFN-α with hzACO-1 and hzACO-1 Y32E, T30R respectively.

| | mAb | | |
|---|---|---|---|
| Subtype | hzACO-1 kd (1/s) | hzACO-1 Y32E, T30R kd (1/s) | hzACo-1/hzACO-1 Y32E, T30R Ratio |
| IFN-αA | 6.24E−04 | 6.85E−05 | 9.1 |
| IFN-α1 | No binding | No binding | — |
| IFN-α4b | 1.12E−03 | 1.74E−05 | 64.4 |
| IFN-αI | 1.55E−03 | 3.15E−05 | 49.2 |
| IFN-αJ1 | 4.54E−03 | 1.95E−04 | 23.3 |
| IFN-αWA | 2.47E−03 | 4.05E−04 | 6.1 |

Example 9

Analysis of hzACO-1 Constructs in a CPE-Assay

This example shows that hzACO-1 was able to inhibit the protective effect of all IFN-α subtypes tested, except for those of IFN-α1 and IFN-αD, which were unaffected by hzACO-1.

Materials & Methods

This anti-IFN-α neutralization assay used is based upon the lytic effect of EMC virus on A549 cells. All IFN-α subtypes can inhibit the EMC virus replication in A549 cells, resulting in cell survival, which can be measured as cellular DNA staining. The neutralizing effect of an anti-IFN-α antibody on different IFN-α subtypes can be measured by diminished cellular DNA staining, corresponding to increased cell lysis.

The assay was performed in plates with 96 wells (Nunc, Cat. No. 167008), where each well contained a final volume of 200 μL. All IFN-α preparations were from PBL Biomedical Laboratories, NJ, USA.

To each well, four solutions were added (IFN-α, hzACO-1, cells and virus) at a volume of 50 μL each. All solutions were prepared in F12Kaighn's medium (Gibco, Cat. no. 21127) with 10% FCS. The specific concentration of each IFN-α subtype (listed in Table 17 below) was derived from previous studies. The antibody concentrations used in the assay were selected based on existing data obtained from use of, e.g., murine antibodies ACO-1.5.2 and ACO-2.2.

Each IFN-α subtype was pre-incubated with hzACO-1 for 2 hours at 37° C., 5% $CO_2$. The anti-interferon antibody was diluted as shown in Table 17 below. After pre-incubation of antibody with IFN-α, 50 μL of cell-solution (300000 cells/mL) were added to obtain 15000 cells/well. After 4.5 hours incubation at 37° C., 5% $CO_2$, 50 μL EMC virus at a concentration of 10^3.5 $TCID_{50}$ were added, followed by incubation for 48 hours at 37° C., 5% $CO_2$.

The supernatant was subsequently carefully removed, and 50 μL crystal violet solution (0.5% crystal violet, 25% methanol) were added. After 15 min of incubation at room temperature, the wells were washed in water and dried overnight.

To the dried plates were then added 200 μL/well of pure methanol for 15 min to extract the crystal violet from the cells. After extraction, 100 μL of the supernatant were carefully transferred to a new 96-well plate (Nunc™, Cat. No. 256510), and 100 μL Milli-Q® water added to each well. The plate was then measured in an ELISA reader at 590 nm.

The raw data retrieved from the ELISA reader was corrected for methanol and plate background prior to analysis.

TABLE 17

CPE assay parameters.

| IFNα Subtype | [IFNα] (pg/μL)* | [hzACO-1] (ng/mL) |
|---|---|---|
| IFN-αA | $1.25 \times 10-1$ | 2.500->0 |
| IFN-α2 | $3.125 \times 10-2$ | 2.500->0 |
| IFN-αF | $6.25 \times 10-2$ | 2.500->0 |
| IFN-αK | $6.25 \times 10-2$ | 2.500->0 |
| IFN-αWA | $6.25 \times 10-2$ | 2.500->0 |
| IFN-αB2 | $2.5 \times 10-2$ | 2.500->0 |
| IFN-αH2 | $1.25 \times 10-1$ | 2.500->0 |
| IFN-αI | $5.0 \times 10-2$ | 2.500->0 |
| IFN-αJ1 | $1.0 \times 10-1$ | 2.500->0 |
| IFN-α4a | $2.5 \times 10-1$ | 250->0 |
| IFN-αC | $2.5 \times 10-2$ | 250->0 |
| IFN-αG | $2.5 \times 10-1$ | 250->0 |
| IFN-α4b | $1.25 \times 10-1$ | 250->0 |
| IFN-αD | 3.75 | 50.000->0 |
| IFN-α1 | 1.0 | 50.000->0 |

Results and Discussion

Six different controls were used on all plates in the study (cells, cells+antibody, cells+IFN-α, cells+antibody+IFN-α, cells+virus, and cells+IFN-α+virus) to ensure that the cytopathic effect observed in the assay was not caused by cytotoxicity of the antibody and/or IFN-α, nor that any lack of IFN-α-protection of the cells against the virus was causing the cytopathic effect. No significant cytotoxic effect was observed in the assays, and at no level of interferon was there a sign of a cytopathic effect in the controls.

As shown in FIG. 4, this CPE-assay showed that the protective effect of almost all interferon subtypes could be inhibited by hzACO-1. However, the protective effects of IFN-αD and IFN-α1 were not inhibited by hzACO-1, even at antibody concentrations of 50000 ng/mL. Accordingly, the specificity of the mouse ACO-1 was retained in the hzACO-1 construct.

Example 10

Analysis of ACO-Derived Antibodies in a Reporter Gene (RG) Bioassay

A luciferase-based reporter gene assay was utilized to evaluate the ability of hzACO-1 antibody variants to neutralize the biological activity of recombinant IFNα subtypes.

Materials

Dulbecco's Modified Eagle's Medium "complete": DMEM incl. phenol red+10% FCS+2 mM L-glutamine+penicilin+streptomycin+2-me., Nunc™ 96-well optical bottom plate, black tissue culture treated, PBS including 1 mM $Ca^{2+}$ and 1 mM $Mg^{2+}$, Steady-Glo® Luciferase assay system (Promega®).

The 93D7 cell line was derived by stable transfection of the A549 cell line (CLL-185, ATCC) with an IFN-inducible construct, harboring the Mx promotor driving a luciferase reporter gene. The Mx promotor consist of 1.6 kb BamHI fragment containing the murine MxA promotor and IFN response elements excised from pSP64-Mxp(PstI-PvuII)-rβ-glo (Lleonart et al. (1990) Biotechnology 8: 1263-1267).

Figure 5:
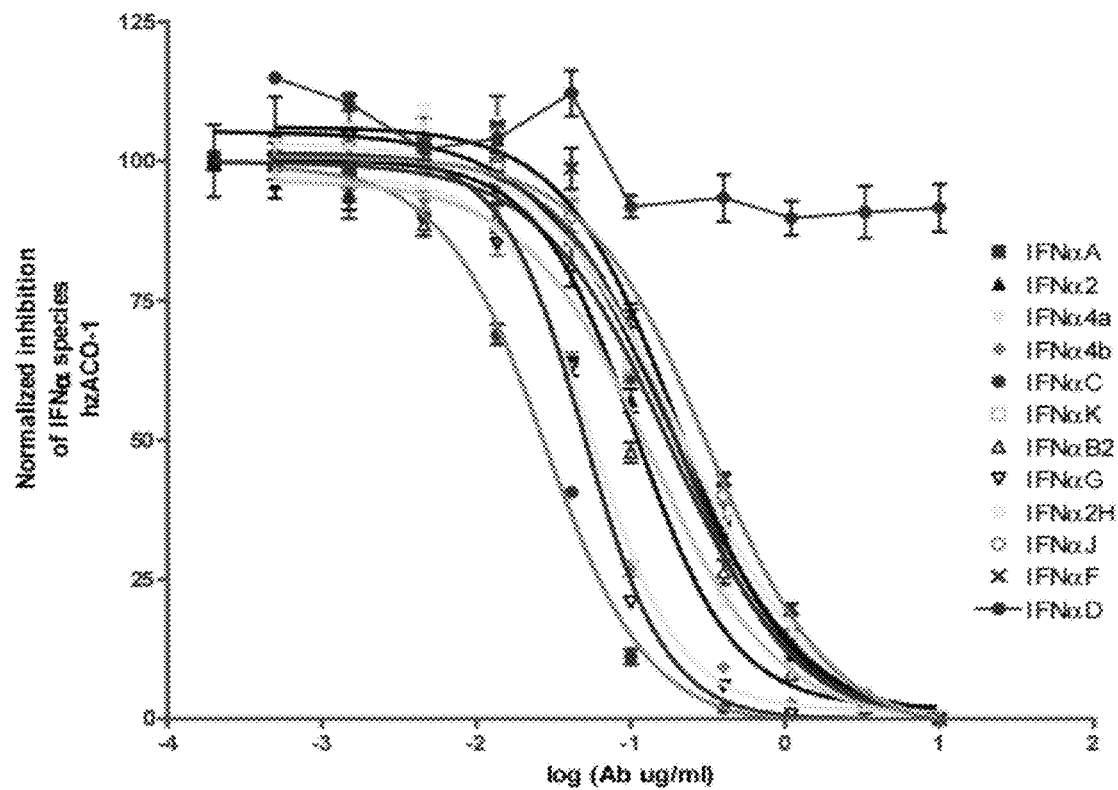
FIG. 5 shows hzACO-1 inhibition of 12 IFN-α species by a reporter gene (RG) assay. Values for each antibody concentration were normalized and the average of four repetitions were calculated. Data are shown as average +/− standard errors. Best fit sigmoidal response curves were calculated using Prism software. R2 values were for all dataset above 0.98 (except for IFN-αD for which no curve fitting was made).

The IFN-α subtypes (all from PBL Biomedical Laboratories, NJ, USA) used are listed in FIG. 5.

Methods

RG assays were performed in quadruplicate wells in opaque Nunc 96-well optical bottom plates. For every assay, a positive control IFNα was included as well as negative control wells containing non-stimulated cells and cells treated with antibody in the absence of IFNα stimulation.

Specifically, adherent 93D7 cells were harvested from flasks by removing the culture media, washing once with PBS, and trypsinizing. Trypsinization was stopped using DMEM complete. Cells were counted and adjusted to 600,000/ml in complete DMEM.

Purified anti-IFN-α mAbs were pre-incubated with recombinant IFN subtypes for 1 h in a total volume of 100 μl DMEM complete at 37° C.+5% CO2. Following antibody-IFN incubation, 50 μl 93D7 cells were added and incubated for 5 h at 37° C.+5% CO2.

To assay for MxA-driven luciferase induction by recombinant IFN subspecies, the concentration of IFN was adjusted to contain the amount to be placed in each well in 100 μl. 100 μl of IFN was placed in quadruplicate wells, incubated for 1 h at 37° C.+5% $CO_2$. Subsequently, 50 μl cells were added and incubation continued for additionally 5 h.

To assay for inhibition of MxA-driven luciferase induction by recombinant IFN subspecies using purified mAbs, 50 μl of a desired dilution of recombinant IFN was added per well. 50 μl of antibody diluted in DMEM complete was then added to the wells and incubated for 1 h at 37° C.+5% $CO_2$. After this incubation, cells were added and incubation continued for additionally 5 h.

After the 5 h incubations, medium was carefully removed from the cells using a multichannel pipet. Next, an adhesive black blocker was affixed to the bottom of the 96 well plate. 100 μl PBS with $Ca^{2+}$ and $Mg^{2+}$ ions was added to each well. 100 μl reconstituted Steady-Glo® reagent was added to each well, making sure that contents in each well were mixed thoroughly. The plates were sealed with a clear adhesive strip. Following 5 min. incubation at room temperature in the dark, luminescence was read in a Topcount® luminescence counter (Perkin Elmer®).

For calculation of the degree of inhibition exerted by the antibody to IFN induced (M×A driven) luciferase activity, counts were when comparing Ab inhibition of various IFN-α subtypes normalized to activity levels in the absence of antibody and this value was set to 100%. For comparing variant form of antibody inhibition of single IFN-αs data are shown as raw luciferase counts. IFNs were initially titrated in the absence of antibody to determine the EC50 and the IFN concentration at which plateau in the assay was reached. When testing for antibody inhibition, IFN was generally used at 80% of maximum stimulation levels to ensure both a solid induction of luciferase as well as operating at a level below saturation in the assay. Prism (GraphPad Software, Inc., San Diego) software was used for calculations and data display.

Results and Discussion

Humanized ACO-1 constructs were evaluated for their ability to inhibit various human IFN-α subtypes in the reporter gene assay. FIG. 5 shows normalized data for the inhibition of 12 IFN-α subtypes by the hzACO-1 antibody. IFN-α stimulation in the absence of antibody was set to 100% whereas mock treated cells (receiving medium only) was set to 0%. Data points are shown with standard error. Curves were calculated as best fit sigmoidal response curves using the Prism software. hzACO-1 was capable of inhibiting all tested subspecies of IFN-αs except for IFN-αD, and accordingly the specificity of the parent mouse ACO-1 antibody was retained during humanization in the hzACO-1 antibody. Inhibition was complete in that, at high antibody concentrations, IFN-α activity was reduced to background levels. IC50 for the inhibition of the various IFN-α subtypes ranged in this study from 28 ng/ml to 314 ng/ml. IFN-αD could not be inhibited even at higher hzACO-1 concentrations.

FIG. 10 shows a comparison of the mouse ACO-1 Ab to the humanized ACO-1 (hzACO-1) as well as two variants hereof in the RG assay. One variant is a humanized ACO-1 harboring a the entire CDRH2 (designated hzACO-1-kabat CDRH2) whereas the hzACO-1 was constructed with a shorter CDRH2 as described in example 2. In addition the figure shows another mutated hzACO-1 which has been optimized for interaction with IFN-αs (designated hzACO-1 Y32E, T30R) through rational design, as described in example 7. These four recombinant mAb variants were compared with respect to inhibition of five different representative IFN-α subtypes in the RG assay.

hzACO-1 displayed for all five IFN subtypes almost comparable IC50 values as mouse ACO-1, quantitatively the IC50s being less than twofold (see Table 18 for relative IC50 values) in accordance with the observed KDs reported in example 8. The humanization was thus accomplished with an affinity loss less than twofold of the parent ACO-1 antibody for functional inhibition. In conclusion, the mAb humanization of ACO-1 has produced an antibody that has retained the affinity for IFN-αs. Accordingly, both the affinity and the potency was considered retained in of the hzACO-1 antibody as compared to the original mouse ACO-1, and no further backmutations were required.

As described in example 2, the humanization method of ACO-1 resulted in an antibody with relatively more human amino acids in the CDR H2 as compared to commonly humanization by simple CDR grafting. Whereas this could be expected to lead to reduced potency in the humanized ACO-1 for neutralization of IFN-α subtypes, as shown in FIG. 10 and Table 18, suprisingly this is not the case, as the hzACO-1 and hzACO-1-kabat CDRH2 are equipotent for all the IFN-α subtypes tested. This is in agreement with the affinities reported for the two ACO-1 variants as described in example 8.

TABLE 18

IC50 values for IFN-α subtypes inhibition by hzACO-1 variants.

| mAb Variant | IC50 values relative to hzACO-1 | | | | |
|---|---|---|---|---|---|
| | IFN-αA | IFN-αB2 | IFN-αF | IFN-αG | IFN-αJ1 |
| hzACO-1 | 1.00 | 1.00 | 1.00 | 1.00 | 1.00 |
| ACO-1 | 0.60 | 0.47 | 0.82 | 0.56 | 0.58 |
| hzACO-1 Y32E, T30R | 0.03 | 0.02 | 0.05 | 0.06 | 0.02 |
| hzACO-1-kabat CDRH2 | 0.95 | 0.88 | 0.95 | 0.78 | 1.15 |

Normalized data. IC50 values in were for each IFN-α species normalized to that of hzACO-1. A value less than one therefore indicates a more potent antibody than hzACO-1 inhibition of IFN-α activity, whereas conversely values higher than one indicates inhibition with lesser potency.

To determine the potency of ACO-2 derived hzACO-1 variants, as described in example 3, these were compared to hzACO-1 using the RG assay. Comparisons were made using two IFN-α subspecies (IFN-αF and IFN-αA). Four different single amino acid substitutions were tested: T28S (i.e., at position 28, (according to Kabat) threonine was substituted with serine), I58S, N31S, and A93V.

Whereas the I58S variant inhibited the IFN-action with reduced potency, and possibly also with reduced efficacy (IFN-αA), the T28S and N31S variants both displayed potencies similar to that of hzACO-1. The A93V substituted variant, however, showed increased potency for inhibition of IFN-effects as measured in the RG assay (FIG. 6). Although differences in the effects of the substitutions could be detected between different IFN-α subtypes, the trend was the same for the two forms in all four cases.

Through rational design using the crystal structure in Example 6, a mutant was constructed having two amino acids changed, HC T30R, LC Y32E of hzACO-1 (designated ACO-1 Y32E, T30R), as described in example 7, to improve binding to IFN-α. Even though the mutations were based on the structure of IFN-α8, as seen from FIG. 10 (A-E) surprisingly this mutant had increased potency for inhibition of all the tested IFN-αs. Furthermore, Table 18 shows that whereas the increment in potency is dependent on the specific subtype it is in the order of 16 fold and up till 50 fold improvement of potency.

It follows that the epitope information obtained from the crystal structure in Example 6 can be used to design other antibody variants with improved binding affinity to this epitope. It also follows that such humanized antibody variants according to the present invention are embraced by the scope of the present invention.

Example 11

Protein Characterization of Humanized ACO-Derived Antibodies

This Example concerns the thermal stability of hzACO-1 and different variants.
Materials
  Antibodies
    hzACO-1 expressed as with human IgG1, IgG2 and IgG4 isotypes
    hzACO-1-T28S
    hzACO-1-N31S
    hzACO-1-A93V
    hzACO-1-T28S-N31S
  The following is a list of the buffers (100 mM) and their pH values used in the study: citric acid/sodium citrate, pH 3.0, 3.5; sodium acetate, pH 4.0, 4.5, and 5.0; histidine, pH 6.0, 6.5; imidazole, pH 7.0; glycine-glycine pH 8.0, 9.0, 10.0.
  The following is a list of additives and their concentrations used in the study: NaCl, 100 mM; sucrose 0.25 M, 0.50 M; phenol, 0.5%; Tween 80, 0.01%; glycerol 10%.
Thermofluor Stability Measurements
  Solutions of 10 µl 400×SYPRO® Orange protein gel stain 5000× Concentrate in DMSO (Invitrogen® Molecular Probes), 25 µl buffer and 10 µl protein (10 µM) were added to wells of a 96-well PCR-plate (Bio-Rad®). The plates were sealed with Microseal B Adhesive sealer MSB-1001 (Bio-Rad®) and heated in a MyiQ Single-Color. Real-Time PCR Detection system (Bio-Rad®) from 25 to 95° C. in increments of 0.5° C. Fluorescence changes in the wells of the plate were monitored simultaneously with a charge-coupled device (CCD) camera. The wavelengths for excitation and emission were 490 and 575 nm, respectively. The midpoint temperature for protein unfolding transition was determined as the first derivative maximum of the fluorescence intensity as a function of temperature,
  The thermofluor graphs for hzACO-1 and variants showed the two expected temperature transitions for IgG proteins, reflecting the two main domains, Fc and Fab. The proteins showed a lower Tm at lower pH. Above pH 5.5 the transition midpoint was rather constant.

The effect of additives was the same for the different antibodies. Generally, sucrose at 0.5M had the most stabilizing effect, while addition of NaCl, phenol and Tween 80 seemed to have a destabilizing effect.

At lower pH (pH 3.5), a difference in stability between hzACO-1 and the different variants was observed (FIG. 7A). The double mutant hzACO-1-T28S-N31S and single mutant hzACO-1-A93V showed the highest stability at this pH. This could be important in a purification process for a therapeutic antibody product, as virus inactivation steps often are carried out at pH 3.5-4.0. At higher pH (pH 4.5, 5.5; FIGS. 7B and 7C, respectively) this difference in stability decreased.

Solution Stability Study

Solutions of hzACO-1-IgG4, hzACO-1-IgG1 and hzACO-1-IgG2 in 15 mM histidine pH 6.5, sucrose 20 mg/ml and Tween® 80 0.01% was incubated at 40° C. and samples were withdrawn for analysis at initial and after 5 weeks. Distribution of intact protein, soluble aggregate and/or fragments of hzACO-1 was, determined using size exclusion chromatography (SEC-HPLC). A high-performance liquid chromatography (HPLC) system model 1100 or 1200 liquid chromatography system (Agilent Technologies®, Palo Alto, Calif.) was used with a BIOSEP® SEC 3000 (Phenomenex®) column at a flow rate of 0.8 mL/min using pH 7.2 and with phosphate-buffered saline (PBS) as the mobile phase. Protein was detected by monitoring the OD at 215 nm. The percentage of each peak in total protein area was calculated.

Figure 11:
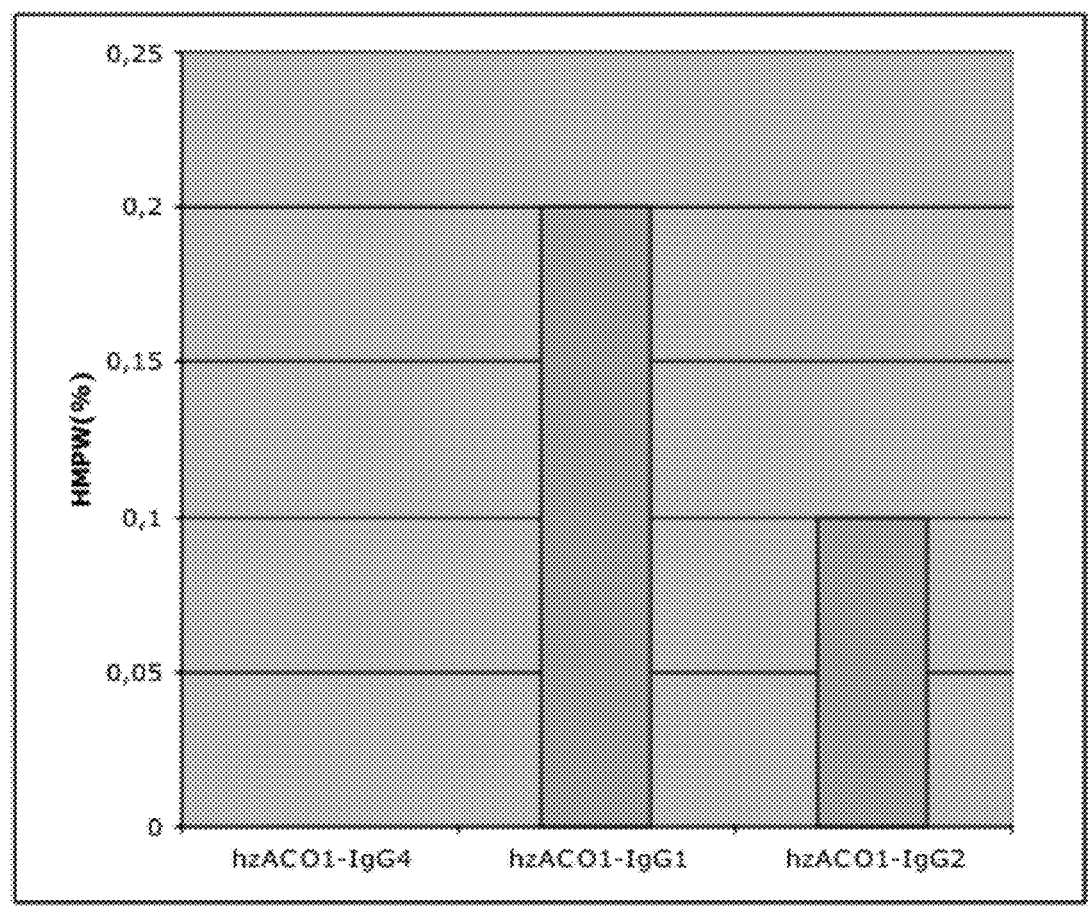
FIG. 11 shows a protein stability study of hzACO-1 expressed with human IgG1, IgG2 and IgG4 isotypes. Aggregation was determined by HPLC after incubation in histidine buffer for 5 weeks.

The amount of formed high molecular weight forms of the hzACO-1-isotypes is shown in FIG. 11 and shows clearly that the IgG4 construct showed no aggregate formation during the incubation while both the IgG1 and IgG2 isotypes formed high molecular weight variants.

Furthermore, the hzACO-1-IgG1 variant showed a low molecular weight fragment after incubation. The amount of the fragment was 1.3%.

Accordingly, from a stability point of view the hzACO-1 IgG4 is a more attractive therapeutic molecule than the corresponding IgG2 and IgG1 antibodies.

Examples 12

ADCC Analysis

As described in example 6 the ACO-1 mAb and humanized versions hereof may block the activity of IFN-α by inhibiting binding of IFN-α to the type I interferon alpha receptor subunit 1 (IFNAR1). Accordingly, a humanized therapeutic ACO-1 mAb may bind to the cell surface making a complex consisting of the antibody, IFN-α and IFNAR2. This raises the risk of ACO-1 inducing antibody dependent cellular cytotoxicity (ADCC).

To this end a ADCC experiment was performed to assess the ability of the hzACO-1 antibody expressed as an IgG4 subtype in the presence of IFN-α2A.

Materials and Methods.

Raji cells (human B cell line (ATCC #CCL-86)) were used as target cells. Raji cells were cultured in RPMI1640 supplemented with 10% fetal calf serum, 10 mM HEPES, 1 mM sodium pyrovate, 1 mM glutamine, 2.5 g/l glucose and 1% penicillin/streptamycin. Highly purified interferon-α2A was used for the assay. The protein was tested in a reporter gene assay for biological activity prior to use. Rituxan® (Nomeco A/S, Denmark) was used as a positive control for ADCC, when using Raji cells, which is a B cell line that expresses the B cell surface antigen CD-20.

Target cells were harvested and counted in a hemocytometer. $1.5*10^6$ cells were transferred to a 15 mL tube and centrifuged. The supernatant was completely removed and the cell pellet was resuspended in 100 µCi $^{51}$Cr (Chromium-51) per $10^6$ cells (volume were adjusted according to decay table). During a 1 hour incubation period at 37° C. with IFN-α the vial was tapped every 15 minutes. Subsequently the cells were washed twice in medium (RPMI1640, 10% FCS), and resuspended in 2 mL medium of assay medium. 5000 $^{51}$Cr labelled cells were plated in a volume of 50 µL in 96 well plates (flat bottom). All samples were analyzed in triplicate Maximum—and minimum releases were determined in wells without effector cells. Maximum release: 5000 target cells/well+1% Triton X-100. Minimum release: 5000 target cells/well. The effector cells were purified from 'buffy coats' by Ficoll density centrifugation using standard techniques. Graded numbers of freshly isolated human PBMCs were added to each well. The following effector to target (E:T) cell ratios were used: 10, 20, 40 and 80. In all experiments hzACO-1 was tested at saturating concentration of 10 µg/mL (66 nM). IFN-α2A was tested at 0.5, 2.5, 5, and 10 nM. The final assay volume was 200 µL. After 4 hours of incubation at 37° C. 30 µL of the supernatant was transferred to a Luma-Plate™ and let to air dry over night. The radioactivity was determined in TopCount NXT (PerkinElmer, USA). Data were entered into the GraphPrism® program and the average counts per minute of triplicates and the corresponding standard deviation were calculated.

Results.

Figure 12:
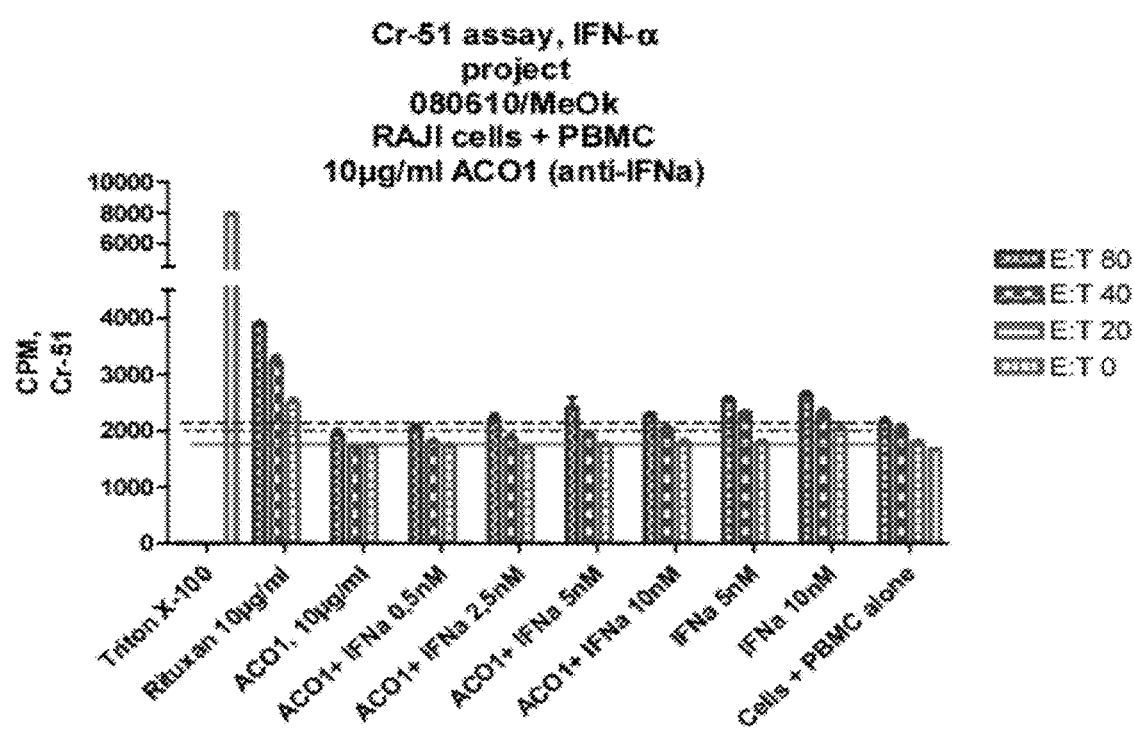
FIG. 12 shows a $^{51}$Cr release assay illustrating lack of ADCC by hzACO-1 IgG4, IFN-α and different combinations hereof, at different effector:target cell ratios (E:T). Cells+ PBMCs alone without IFN-α pr hzACO-1 determines background lysis and Triton-X 100 illustrates maximal lysis. Rituxan was included as a positive control and induces detectable cell lysis at all E:T ratios.

As seen in FIG. 12, no induction of ADCC above background (cells or cells with IFN-α) could be observed for the hzACO-1 molecule, expressed as an IgG4 in the presence or absence of IFN-α. In contrast, Rituxumab, which was used as a positive control did induce cell lysis at different ratios of effector and target cell ratios (E:T)

Example 13

Complement Binding ELISA Assay

As described in example 6 the ACO-1 mAb and humanized versions hereof may block the activity of IFN-α by inhibiting binding of IFN-α to the type I interferon alpha receptor subunit 1 (IFNAR1). Accordingly, a humanized therapeutic ACO-1 mAb may bind to the cell surface making a complex consisting the antibody, IFN-α and IFNAR2. This raises the risk for activating the complement system and inducing complement dependent cytotoxicity (CDC).

The purpose of the present complement binding study was to test whether the classical complement pathway is activated when hzACO-1 expressed as a human IgG4 isotype binds to and forms a complex with a corresponding epitope on hIFN-α. This is accomplished by using an ELISA, which measures the binding of antibodies to C4. Binding of C4 indicates that the C1s is changed and the complement cascade has started. Once the C4 has bound, the other complement components from the plasma will in turn be activated, bind, and enzymatically cleave the next components of the cascade.

Materials and Methods.

Streptavidin-coated microtiter plates (236001, Nunc®) were used as ELISA plates. Biotinylated hIFN-α2A was used as antigen source and the plates were coated in 100 µl/well by 0.25 pg/ml protein diluted in washing buffer (10 mM Na3PO4+145 mM NaCl+0.05% Tween® 20). This hIFN-α concentration was shown to be the optimal coating concentration in an ELISA. The plates were incubated for 60 min. at RT and gentle shaking and then washed five times in washing buffer, leaving the buffer from the last wash in the plates for 30 min. to block possible residual binding sites on the plates.

The buffer was discarded from the plates and 100 μl hzACO-1 mAb diluted in washing buffer were added to the plates at 1 μg/ml. The plates were incubated for 60 min. at RT and gentle shaking. The plates were washed five times in washing buffer. A polyclonal anti-IgG4 pAb was used as a positive control by crosslinking of the hzACO-1 IgG4 mAb. The anti-IgG4 pAb mAb was diluted in washing buffer and added to the plates in serial dilutions from 32 μg/ml to 32 ng/ml in 100 μl/well. Two different purifications of the anti-IgG4 pAb were used, one affinity purified antibody and one protein A purified antibody. The plates were incubated for 60 min. at RT and gentle shaking. The plates were washed five times in washing buffer. Human plasma diluted 1:200 in plasma buffer (PBS w/0.3 mM $Ca^{2+}$, 1 mM $Mg^{2+}$) was added at 100 μl/well. The plates were incubated for 60 min. at 37° C. with gentle shaking. The plates were washed five times and mouse anti-human C4 (HYB162-02+HYB162-04, SSI), each diluted 1:2000 in washing buffer, was added to the plates at 100 μl/well. The plates were incubated for 60 min at RT with gentle shaking. The plates were washed five times in washing buffer before addition of 100 μl/well of HRP-rabbit anti-mouse IgG (Dako® P0260), diluted 1:1000 in washing buffer. The plates were washed five times and all wells added 100 μl of TMB substrate. After about 6 min. of incubation, 100 μl of 4M $H_3PO_4$ was added to all wells to stop the enzyme reaction. The colour was measured spectrophotometrically by a Victor™ plate reader (Wallac™).

Figure 13:
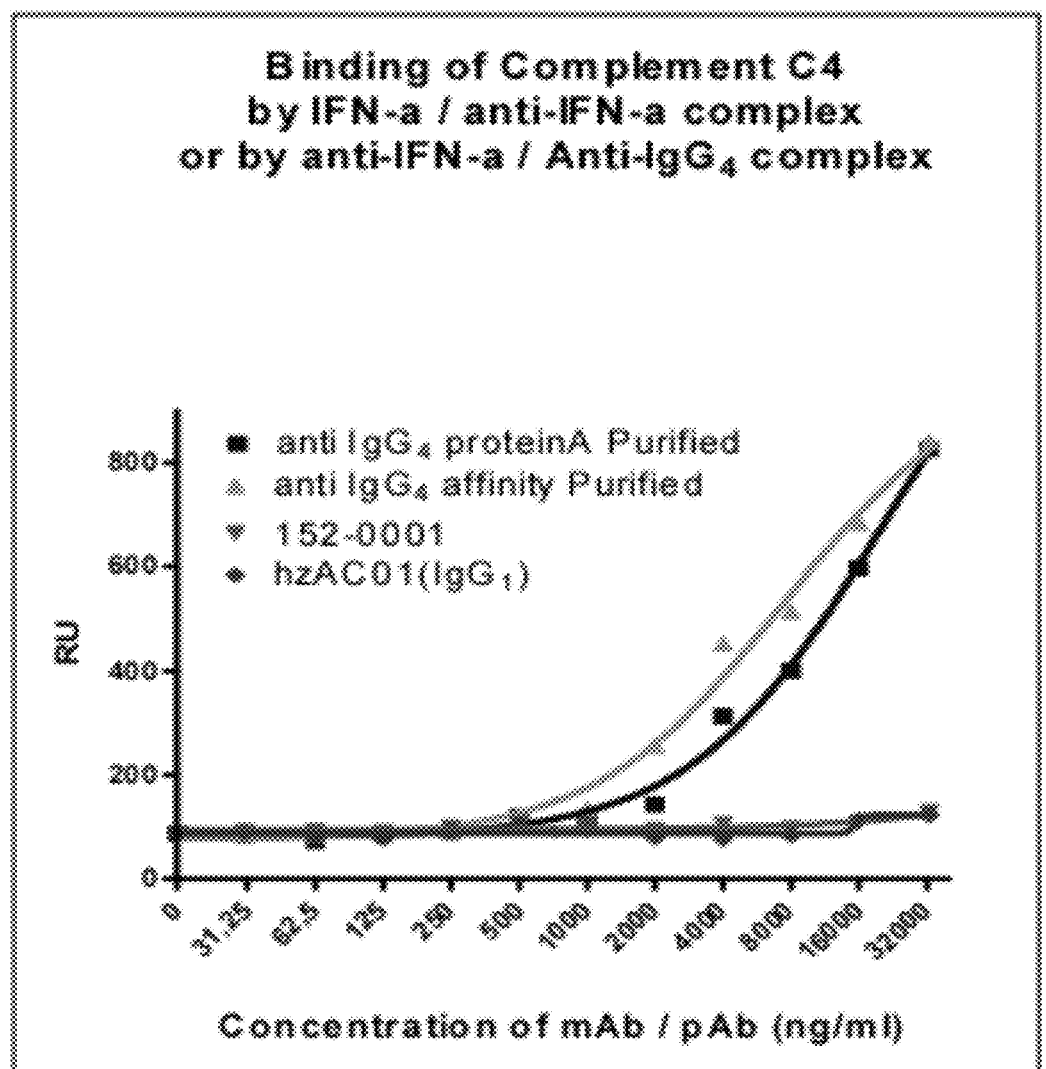
FIG. 13 shows a complement binding study by Elisa. The hzACO-1 expressed as an IgG4 was unable to fix complement when bound to IFN-α. As a positive control the hzACO-1 was cross bound with an anti-IgG4 pAb, and a clear dose dependent binding of C4 to the anti-IgG4 was detected.

Results.

hzACO-1 expressed as a human IgG4 isotype, was tested for the ability to bind complement components by ELISA using plates coated with IFN-α. This was visualised by detecting binding to C4 which is one of the components in the classical complement cascade. As shown in FIG. 13, hzACO-1 IgG4 was unable to fix complement. As a positive control a polyclonal anti-IgG4 pAb was used to induce binding by cross-linking of the hzACO-1 IgG4 antibody. If the hzACO-1 was cross bound with an anti-IgG4 pAb, a clear dose dependent binding of C4 to the anti IgG4 was detected.

Example 14

Selection of Antibody Isotype

When expressing a humanized monoclonal antibody, a human antibody isotype needs to be selected for expression of the full length human antibody. For the development of a neutralizing anti-IFN-α antibody, no Fc-mediated effector functions are required.

Furthermore, although the ACO-1 derived antibodies are capable of neutralizing IFN-αactivity (example 9 and example 10), the binding epitope of the ACO-1 antibody variants, as described in example 6, is compatible with simultaneous binding of the IFNAR2 receptor subunit and IFN-α. Accordingly, although the therapeutic hzACO-1 mAb binds to the soluble IFN-α cytokine, the mAb may in fact be able to bind to cell surfaces through the IFN-α/IFNAR2 complex hand cause cytotoxicity by recruitment of Fc mediated effector functions. In addition to this, for antibodies against Type I IFNs (IFN-α and IFN-β) the selection of the antibody isotype is of particular importance, as it has been described that the Fc part of anti-IFN mAbs may in fact cause undesired biological effects resulting in potentiation instead of neutralization of IFN in certain cell types as described below (Moll H P. et al J Immunol 180, 1594-604, 2008).

In the presence of Type I IFNs, antibodies against human IFN-α or IFN-β that normally neutralize IFN activity in other cell types, instead induce IFN activity in human endothelial cells and PMBCs in the presence of IFN-α or IFN-β. The antibodies used in these studies are of the mouse IgG1 isotype, which are known to cross bind to human Fc receptors. The induction of IFN activity is only seen for intact antibodies and not Fab or Fab2 fragments of the same anti-bodies and appears to be inhibited by blockade of Fc receptors with an antibody isotype control mAb. Accordingly, although the molecular mechanism of this phenomenon is not known, it appears to require that these mAbs bind to cell surface receptors through the Fc part. Furthermore, this phenomenon appears to be specific to Type I IFNs as antibodies against Type II IFN, IFN-γ, and a similar phenomenon is not observed for antibodies against the Type I IFN receptor, IFNAR (Moll H P. et al J Immunol 180, 1594-604, 2008).

In summary, for the development of a therapeutic anti-IFN mAb for neutralization of IFN-α Fc mediated effector function are not required and may in fact cause undesired biological effects by causing cytotoxicity or potentiating IFN activity in certain cell types in patients treated with an anti-IFN-α mAb. Consequently, generation of a humanized mAb that is unable to induce effector functions may be crucial.

Four different human antibody isotypes exists i.e. IgG1, IgG2 IgG3 and IgG4. Of these IgG1 and IgG3 are the most efficient in binding to Fc receptors and complement and consequently cause activation of Fc mediated effector functions such as-dependent cellular cytotoxicity (ADCC) and complement-dependent cytotoxicity (CDC) (Salfeld J G. Biotechnol 25, 1369-1372, 2007). Mutations that abrogate binding of various Fc receptors and C1q have been described in the literature (Hezareh M. et al J Virol 75, 12161-12168, 2001. Idusogie E E. Et al. J Immunol 164, 4178-4184, 2000. Lund J. et al J Immunol.; 147:2657-6, 1991. & Chappel et al 1991, Canfield M S et al J Exp Med. 173:1483-91, 1991). However selection of e.g. an IgG1 isotype and inclusion of several mutations will potentially be able to result in immunogenicity and cause an immune response against the Fc part in humans, as such a modified Fc region not will be naturally occurring in humans.

For that reason the hzACO-1 anti-IFN-α mAb was expressed both with IgG2 and IgG4 isotypes, which are both used in number of therapeutic antibodies (Salfeld J G. Biotechnol 25, 1369-1372, 2007). Unexpectedly, the expression levels of the IgG4 construct was significantly higher than of the IgG2 hzACO-1 variant (example 5) which will improve the production yield considerably. Furthermore, the IgG2 hzACO-1 molecule but not the IgG4 variant was prone to aggregation (example 11). This is considered a serious problem in drug development, as aggregation may lower yield during production, limit shelf-life and result in reduced potency in patients due to increased immunogenicity.

Accordingly, the hzACO-1 IgG4 construct was selected for further characterization in an ADCC assay in the presence of IFN-α, as well as a complement fixation ELISA assay, as described in example 12 and 13, respectively. These data confirm that the hzACO-1 IgG4 molecule is indeed unable to cause undesired cytotoxicity. The expected lack of potentiation of IFN-αactivity may also be confirmed in PBMCs and ECs, as described in Moll et al 2008.

In summary, the hzACO-1 IgG4 molecule appears to be a particular suitable therapeutic molecule as it is capable of neutralizing IFN-α without induction of undesired side-effects caused by Fc-mediated effector functions including cytotoxicity and potentiation of IFN activity, and as it is a stable and well expressed molecule making it suitable for manufacturing and administration to patients.

Example 15

Analysis of t-Cell Epitopes

Based on standard technologies for immunogenicity predictions (De Groot, A. S, and Moise, L. Curr. Opin. Drug Discov. Devel. 10, 332-340, 2007) the pocket profile method (Sturniolo, T. et al. Nat. Biotechnol. 17, 555-561, 1999) as extended by ProPred (Singh, H. & Raghava, G. P. ProPred. BioIFNormatics. 17, 1236-1237, 2001) was used to predict linear T-Cell epitopes among 51 HLA-DRB alleles. The method calculates the number of alleles a given 9 residue long peptide within the protein under evaluation can bind. If a given peptide that binds many alleles is of non-human origin, this can be used as an indirect measure of immunogenicity. If the peptide is of human origin, no immune response is expected due to the early negative selection of corresponding T-Cells.

It is the purpose of this example to compare the predicted immunogenicity of a humanization procedure using the full length hzACO-1-kabat CDRH2 to the actual humanization procedure applied for hzACO-1.

As input sequences to the ProPred algorithm, full length ACO-1 CDR_H2 with 10+10 residues added around hzACO-1-kabat CDRH2 is used: APGQGLEWMG/EINPSH-GRTIYNENFKS/RVTMTRDTST (CDR_H2_Full), together with the comparable hzACO-1 sequence APGQ-GLEWMG/EINPSHGRTIYAQKFQG/RVTMTRDTST (CDR_H2_Human) in the same area.

Running CDR_H2_Full through the T-Cell epitope predictor gives the following 3 epitopes: WMGEINPSH (binding to 4% of HLA-DRB alleles), INPSHGRTI (6%) and FKSRVT-MTR (24%). For CDR_H2_Human the first two minor epitopes are identical, whereas the last major epitope is converted to FQGRVTMTR (27%). Even though it is still a T-cell epitope, it is now a fully human sequence and from the assumption, that self reactive T-Cells are deleted by negative selection in the Thymus, this potential major epitope in CDR_H2_Full has been removed by the CDR_H2_Human sequence.

Accordingly hzACO-1 is expected to be less immunogenic, than a traditional CDR grafted humanized ACO-1.

Example 16

CDR Truncation

As described in example 2 the mouse ACO-1 antibody was humanized by an untraditional method. This constitutes the designing of a mask of residues predicted to comprise the paratope, based on a 3D model of hzACO-1 and IFN-αA. The application of this humanization method resulted in a hzACO-1 antibody with fewer murine residues than an antibody humanized by simple CDR grafting, since the peptide comprising the 5 C-terminal amino acids of the optimized hzACO-1 CDR H2 sequence was identical to the corresponding human framework sequence. In contrast, the corresponding peptide sequence in a traditionally CDR grafted humanized antibody (the hzACO-1-kabat CDRH2) was of murine origin. Accordingly, this humanization procedure resulted in a humanized antibody with a more human sequence, less likely to cause immunogenicity in patients. Analysis of the sequences of the CDR H2 revealed that by reducing the mouse amino acid residues in the hzACO-1, an MHC class II T cell epitope containing the mouse amino acids is removed and replaced with a fully human, which patients would be expected to be tolerant to. Accordingly, this confirmed that hzACO-1 is expected to be less immunogenic, than a traditional CDR grafted humanized ACO-1 antibody.

The affinity of the hzACO-1 antibody was retained, within two-fold of the mouse ACO-1 antibody, as shown in example 8. Accordingly, no further mouse backmutations were required. Furthermore, the IFN-α subtype profile of the antibody, binding and neutralizing all IFN-α subtypes except the IFN-α1/D had been retained, as described in example 8, 9 and 10. Despite containing fewer mouse amino acids in the CDR H2, the affinity of the hzACO-1 was identical to the affinity and the potency of the hzACO-1-kabat CDRH2 antibody, containing the full length mouse CDR H2 from the mouse ACO-1 antibody (Example 8 and 9, respectively).

Furthermore, the replacement of the sequence AQK instead of NEN in position 60-62 in heavy chain by use of the described humanization method has the advantage of avoiding two asparagine that may be prone to deamidation. Deamidation change the net charge of proteins which may effect stability and/or specificity. By keeping the sequence AQK the homogeneity of hzACO-1 will be better preserved. Comparison of the hzACO-1 to the traditionally CDR grafted hzACO-1-kabat CDRH2 version, revealed that the hzACO-1 is a highly stable protein, whereas the hzACO-1-kabat CDRH2 antibody unexpectedly had a tendency to aggregate (example 11). Aggregation is considered a serious problem in drug development, as aggregation may result in lower yield during production, limited shelf-life and reduced potency in patients due to increased immunogenicity. In addition, the expression levels of the hzACO-1 construct was unexpectedly twice that of the hzACO-1-kabat CDRH2 variant (example 5).

In summary, the hzACO-1 IgG4 antibody was humanized by a novel approach resulting in a therapeutic antibody with less mouse amino acids which is less likely to cause immunogenicity in patients. Despite containing fewer amino acids from the original mouse mAb, this humanized antibody had a comparable affinity, potency and IFN-α subtype profile as the mouse antibody and a humanized version generated by traditional CDR grafting. Furthermore, the hzACO-1 antibody is less prone to deamidation and has a higher expression level. Thus, the hzACO-1 antibody it is a stable and well expressed molecule suitable for manufacturing and administration to patients.

The invention claimed is:

1. An isolated IgG4 isotype antibody that binds human interferon-α and comprises a VH domain comprising SEQ ID NO:3 and a VL domain comprising SEQ ID NO:6.

2. An isolated antibody comprising at least one light chain that comprises the CDRs:
VL1 having the amino acid sequence of SEQ ID NO: 18;
VL2 having the amino acid sequence of SEQ ID NO: 179; and
VL3, having the amino acid sequence of SEQ ID NO:20, and
at least one heavy chain that comprises the CDRs:
VH1 having the amino acid sequence of SEQ ID NO: 15;
VH2 having the amino acid sequence of SEQ ID NO:21; and
VH3 having the amino acid sequence of SEQ ID NO:17.

* * * * *

UNITED STATES PATENT AND TRADEMARK OFFICE
CERTIFICATE OF CORRECTION

PATENT NO. : 8,163,885 B2
APPLICATION NO. : 12/597357
DATED : April 24, 2012
INVENTOR(S) : Svensson et al.

It is certified that error appears in the above-identified patent and that said Letters Patent is hereby corrected as shown below:

Column 75, line 65: "haying" should be --having-- and "179" should be --19--.

Column 76, line 58: the "," following "VL3" should be omitted.

Column 76, line 64: "SEQ ID NO:I 7" should be --SEQ ID NO:17--.

Signed and Sealed this
Ninth Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,163,885 B2  Page 1 of 1
APPLICATION NO. : 12/597357
DATED : April 24, 2012
INVENTOR(S) : Svensson et al.

It is certified that error appears in the above-identified patent and that said Letters Patent is hereby corrected as shown below:

On the Title Page

Item (75) Inventors, should read:

--(75) Inventors: Lars Anders Svensson, Malmö (SE); Soren Padkjaer, Værløse (DK); Birgitte Friedrichsen, Gentofte (DK); Berit Olsen Krogh, Rødovre (DK); Inger Lund Pedersen, Vanløse (DK); Jan Fleckner, Værløse (DK)--.

Signed and Sealed this
Twenty-third Day of May, 2017

Michelle K. Lee
*Director of the United States Patent and Trademark Office*